(12) United States Patent
Harty et al.

(10) Patent No.: US 10,160,756 B2
(45) Date of Patent: Dec. 25, 2018

(54) ANTIVIRAL COMPOUNDS AND METHODS USING SAME

(71) Applicant: THE TRUSTEES OF THE UNIVERSITY OF PENNSYLVANIA, Philadelphia, PA (US)

(72) Inventors: Ronald N. Harty, Bensalem, PA (US); Bruce D. Freedman, Merion Station, PA (US); Jay E. Wrobel, Lawrenceville, NJ (US); Allen B. Reitz, Lansdale, PA (US); H. Marie Loughran, Perkasie, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 15/128,471

(22) PCT Filed: Mar. 31, 2015

(86) PCT No.: PCT/US2015/023502
§ 371 (c)(1),
(2) Date: Sep. 23, 2016

(87) PCT Pub. No.: WO2015/153554
PCT Pub. Date: Oct. 8, 2015

(65) Prior Publication Data
US 2017/0174678 A1 Jun. 22, 2017

Related U.S. Application Data

(60) Provisional application No. 61/972,842, filed on Mar. 31, 2014.

(51) Int. Cl.
| | | |
|---|---|---|
| C07D 471/04 | (2006.01) | |
| C07D 513/04 | (2006.01) | |
| A61K 31/498 | (2006.01) | |
| A61K 31/428 | (2006.01) | |
| A61K 45/06 | (2006.01) | |
| A61K 31/454 | (2006.01) | |
| C07D 403/12 | (2006.01) | |
| C07D 241/44 | (2006.01) | |
| C07D 417/14 | (2006.01) | |

(52) U.S. Cl.
CPC .......... *C07D 471/04* (2013.01); *A61K 31/428* (2013.01); *A61K 31/454* (2013.01); *A61K 31/498* (2013.01); *A61K 45/06* (2013.01); *C07D 241/44* (2013.01); *C07D 403/12* (2013.01); *C07D 417/14* (2013.01); *C07D 513/04* (2013.01)

(58) Field of Classification Search
None
See application file for complete search history.

(56) References Cited

U.S. PATENT DOCUMENTS

| 9,469,615 B2 * | 10/2016 | Boyce ................. C07D 241/42 |
| 2011/0269742 A1 | 11/2011 | Cogan et al. |
| 2013/0303517 A1 | 11/2013 | Boyce et al. |

FOREIGN PATENT DOCUMENTS

| WO | 03015714 A2 | 2/2003 |
| WO | 03051835 A2 | 6/2003 |
| WO | 2009073719 A1 | 6/2009 |

OTHER PUBLICATIONS

PubChem Compound Summary for CID 55486576, AKOS006693688, Create date: Jan. 25, 2012, retrieved from the internet on May 6, 2015 <URL:https://pubchem.ncbi.nim.nih.gov/compound/CID55486576>.
PubChem, Compound Summary for CID 24629621, AGN-PC-04O2DA, Create Date Feb. 29, 2008, retrieved from the internet on May 6, 2015 at <URL: https://pubchem.ncbi.nlm.nih.gov/compound/CID24629621>.
PubChem, Compound Summary for CID 36470979, MolPort-028-757-32, Create Date: May 29, 2009. Retrieved on May 7, 2015 from the internet at <URL: https://pubchem.ncbi.nlm.nih.gov/compound/CID36470979>.
International Search Report and Written Opinion dated Aug. 21, 2015—PCT/US2015/023502.
Selected Chemical Abstract Registry Numbers, Retrieved Mar. 30, 2014 (Part 1).
Selected Chemical Abstract Registry Numbers, Retrieved Mar. 30, 2014 (Part 2).
Supplementary Partial European Search Report for European Patent Application No. 15772484.0 dated Jul. 25, 2017.

* cited by examiner

*Primary Examiner* — Kamal A Saeed
(74) *Attorney, Agent, or Firm* — Saul Ewing Arnstein & Lehr LLP; Kathryn Doyle; Domingos J. Silva

(57) ABSTRACT

The present invention includes compounds that are useful in preventing or treating viral infections, such as viral infections caused by a filovirus, arenavirus, rhabdovirus, paramyxovirus, and/or retrovirus. The present invention further includes compositions comprising such compounds, and methods of treating a viral infection in a subject using such compounds.

8 Claims, 17 Drawing Sheets

Fig. 2A

Compound 2

Compound 3

Compound 6

Fig. 6A

|  | Z-WT | Z-ΔPPPY |
|---|---|---|
| Cells | ▬ | ▬ | - LFV-Z
| VLPs | ▬ |  | - LFV-Z

Fig. 6B

Compound 4 (µM)    0    0.1    0.5    1.0

Cells — LFV-Z
       — actin

VLPs — LFV-Z

Fig. 6C

Compound 5 (µM)    0    0.1    0.5    1.0

Cells — LFV-Z
       — actin

VLPs — LFV-Z

| | R |
|---|---|
| 3f | -C(=O)NHCH$_2$CH$_3$ |
| 3g | -C(=O)NH-cyclopropyl |
| 5 | -C(=O)NH-Ph |
| 3i | -C(=O)NH-CH$_2$-2-thiophenyl |
| 3j | 3-methyl-1,2,4-oxadiazol-5-yl |
| 3k | 3,5-dimethyl-1H-pyrazol-4-yl |
| 3l | 1,3,5-trimethyl-1H-pyrazol-4-yl |

Budding, BIMC, VSV Assays, and MW, LogP and TPSA properties for selected analogs

| | | | | M VP40 budding | | | | | E VP40 budding | | | BIMC MVP40 | | | BIMC EVP40 | | | VSV-WT | | | |
|---|---|---|---|---|---|---|---|---|---|---|---|---|---|---|---|---|---|---|---|---|---|
| | | | | (% reduction, µM) | | | | | | | | | | | | | | | | | |
| # | MW | LogP | TPSA | 20 µM | 10 µM | 1 µM | 0.5 µM | 0.1 µM | 40 µM | 20 µM | 10 µM | 10 µM | 1 µM | 0.5 µM | 40 µM | 20 µM | 20 µM | 10 mM | 1 µM | 0.5 µM | 0.1 µM |
| 1 | 400.4 | 2.38 | 74 | 70 | 41 | | | | | | | | | | | | | | | | |
| 2a | 369.5 | 2.43 | 74 | 97 | | | | | | | | | | | | | | | | | |
| 2e | 395.5 | 3.42 | 54 | | 100 | 0 | | 0 | 97 | 60 | 70 | 50 | 89 | | 89 | 50 | 96 | 74 | | | |
| 2f | 445.6 | 4.21 | 63 | | | | | | | | | 78 | | 73 | | 78 | | 77 | 50 | | |
| 3a | 358.3 | 1.85 | 84 | | 100 | 88 | 91 | 91 | 94 | 78 | | 78 | 60 | | | | | 97 | | 95 | 50 |
| 3h | 352.4 | 2.91 | 84 | | 100 | 100 | 100 | | | | | | | | | | | | | | |
| 3i | 372.5 | 2.53 | 84 | | | 97 | 77 | 9 | | | | | | | | | | | | | |

M VP40 = Marburg VP40; E VP40 = Ebola VP40; VSV-WT = Vesicular stomatitis virus: wild type

Fig. 11

ANTIVIRAL COMPOUNDS AND METHODS USING SAME

CROSS-REFERENCE TO RELATED APPLICATIONS

The present application is a 35 U.S.C. § 371 national phase application from, and claims priority to, International Application No. PCT/US2015/023502, filed Mar. 31, 2015, and published under PCT Article 21(2) in English, which claims priority under 35 U.S.C. § 119(e) to U.S. Provisional Application No. 61/972,842, filed Mar. 31, 2014 all of which applications are incorporated herein by reference in their entireties.

STATEMENT REGARDING FEDERALLY SPONSORED RESEARCH OR DEVELOPMENT

This invention was made with government support under grant numbers AI102104, U54 AI057168, R41 AI113952, R44 AI125005, and R44 AI115759 awarded by the National Institutes of Health. The government has certain rights in the invention.

BACKGROUND OF THE INVENTION

Filoviruses, such as Ebola (EBOV) and Marburg (MARV), arenaviruses, such as Lassa fever (LFV) and Junin (JUNV), and rhabdoviruses, such as vesicular stomatitis virus (VSV) and rabies virus (RABV), are enveloped RNA viruses that can cause severe disease in humans and animals. For example, Filovirus and arenavirus infections can result in hemorrhagic syndromes with high mortality rates in humans, and as such, these viruses are classified as NIAID Category A priority pathogens (Feldmann et al., 1996. Filoviruses. In Baron S (ed.), Medical Microbiology, 4$^{th}$ Ed, Galveston (Tex.); Feldmann et al., 1996, Adv. Virus Res. 47:1-52; Grant et al., 2012, Viruses 4:2317-2339; Peters et al., 1989, Rev. Infect. Dis. 11 Suppl 4:S743-749). There are currently no FDA-approved vaccines or therapeutics to control infection and transmission of EBOV, MARV and JUNV, and the FDA-approved drug to treat LVF (ribavirin) has low efficacy in treating the disease.

The matrix proteins of filoviruses (VP40), arenaviruses (Z), and rhabdoviruses (M) are highly abundant and play key roles in promoting virus assembly and egress (Hartlieb et al., 2006, Virol. 344:64-70; Jasenosky et al., 2004, Virus Res. 106:181-188; Liu et al., 2010, Future Virol. 5:481-491). For example, independent expression of EBOV or MARV VP40 leads to the production of virus-like particles (VLPs) that accurately mimic the morphology and budding characteristics of live infectious virus (Hartlieb et al., 2006, Virol. 344:64-70; Jasenosky et al., 2004, Virus Res. 106:181-188; Liu et al., 2010, Future Virol. 5:481-491). A common feature of these various viral matrix proteins is the presence of one or more motifs referred to as Late (L) budding domains. The conservation of L-domains within the matrix proteins of filoviruses, arenaviruses, rhabdoviruses, paramyxoviruses, and retroviruses suggests that they are generally important and required for efficient RNA virus budding (8). Viral L-domains recruit host ESCRT (endosomal sorting complex required for transport) complexes to mediate efficient virus-cell separation (or "pinching-off"), and consist of core consensus amino acid motifs such as PPxY, P(T/S)AP (PTAP), YxxL, or FPIV (x is any amino acid).

Viral L-domain/host interactions are important for efficient virus egress and spread. For example, the PPxY motif mediates interactions with WW-domains within mammalian E3 ubiquitin ligase neural precursor cell expressed developmentally down-regulated protein 4 ("Nedd4") to facilitate virus egress. Nedd4 is associated with the ESCRT machinery and mono-ubiquitinates ESCRT proteins as well as viral matrix proteins (Liu et al., 2010, Future Virol. 5:481-491). A functional PPxY motif is present in the matrix proteins of EBOV, MARV, VSV, RABV, LFV, and others. Thus, recruitment of host proteins such as Nedd4 by viral L-domains represents a broad-spectrum target for the identification and advancement of antiviral drugs hypothesized to dampen virus egress from infected cells, thereby reducing virus dissemination and disease progression.

There is an unmet need for the identification and development of potent, broad-spectrum antiviral agents, particularly those that can target high priority pathogens for which no current treatments are available. In particular, there is an unmet need for the development of safe and effective therapeutics against biodefense and high priority viral pathogens, including filoviruses (e.g., Ebola and Marburg) and arenaviruses (e.g., Lassa fever and Junin), which cause severe hemorrhagic fever syndromes with high mortality rates. The present invention addresses and meets these needs.

BRIEF SUMMARY OF THE INVENTION

The invention provides compounds, or salts or solvates thereof. The invention further provides pharmaceutical compositions comprising at least one pharmaceutically acceptable carrier and at least one compound of the invention. The invention further provides methods of treating or preventing a viral infection in a subject in need thereof. The invention further provides a kit comprising at least one compound of the invention and instructional material comprising instructions for using the at least one compound to treat or prevent a viral infection in a subject.

In certain embodiments, the at least one compound is selected from the group consisting of:
a compound of formula (I):

$$\underset{Q}{\overset{a \quad b}{\bigcirc}}\!\!-\!\!\overset{N}{\underset{}{\diagdown}}\!\!\overset{R}{\underset{(CH_2)_m-N}{\overset{|}{-}}}\!\!\overset{(CH_2)_m}{\underset{Z-R^1,}{|}} \quad (I)$$

wherein in (I):
ring a is fused with ring b to form bicyclic core ab, wherein ring a is selected from the group consisting of benzene, pyridine, pyrimidine, pyrazine and triazine, wherein a is optionally substituted with one or more substituents independently selected from the group consisting of $C_1$-$C_4$ alkyl optionally substituted with one or more fluoro atoms, $C_3$-$C_6$ cycloalkyl optionally substituted with one or more fluoro atoms, nitro, cyano, halogen, hydroxy, $C_1$-$C_4$ alkoxy optionally substituted with one or more fluoro atoms, $C_1$-$C_4$ thioalkoxy optionally substituted with one or more fluoro atoms, —SO$_2$($C_1$-$C_4$ alkyl), —C(=O)OR, —NRR, and —C(=O)NRR;

Q is selected from the group consisting of S, S(=O), S(=O)$_2$, O and NR;

Z is selected from the group consisting of —CH$_2$—, —C(=O)—, and —C(R)(R$^4$)—C(=O)N (R$^5$)—*, wherein—* is the covalent bond that links Z and R$^1$;

m is 0, 1 or 2;

n is 1, 2, or 3; with the proviso that if m is 0, then n is 2 or 3;

each occurrence of R, R$^4$ and R$^5$ is independently H or C$_1$-C$_4$ alkyl; or R$^4$ and R$^5$ are joined as to form an optionally substituted —(CH$_2$)$_{1-4}$-alkanediyl group;

R$^1$ is selected from the group consisting of

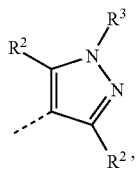

—CH$_2$CH$_2$O-(aryl or substituted aryl), —CH$_2$CH$_2$O-(hereoaryl or substituted heteroaryl), and —C(=O)—N(R)CH$_2$CF$_3$;

each occurrence of R$^2$ is independently selected from the group consisting of H, halo, —OR, C$_1$-C$_4$ alkyl optionally substituted with one or more fluoro atoms, C$_3$-C$_6$ cycloalkyl optionally substituted with one or more fluoro atoms, aryl, substituted aryl, heteroaryl, substituted heteroaryl, arylalkyl, substituted arylalkyl, heteroarylalkyl, substituted heteroarylalkyl, heteroalkyl, substituted heteroalkyl, —C(=O)OR, and —C(=O)NRR; and, R$^3$ is selected from the group consisting of H, C$_1$-C$_4$ alkyl optionally substituted with one or more fluoro atoms, C$_3$-C$_6$ cycloalkyl optionally substituted with one or more fluoro atoms, aryl, substituted aryl, heterocycle, substituted heterocycle, arylalkyl, substituted arylalkyl, heteroarylalkyl, substituted heteroarylalkyl, heteroalkyl, substituted heteroalkyl, —CH$_2$C(=O)OR, and —CH$_2$C(=O)NRR; and, a compound of formula (II):

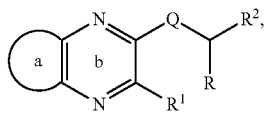

(II)

wherein in (II):

ring a is fused with ring b to form bicyclic core ab, wherein ring a is selected from the group consisting of benzene, pyridine, pyrimidine, pyrazine and triazine, wherein a is optionally substituted with one or more substituents independently selected from the group consisting of C$_1$-C$_4$ alkyl optionally substituted with one or more fluoro atoms, C$_3$-C$_6$ cycloalkyl optionally substituted with one or more fluoro atoms, nitro, cyano, halogen, hydroxy, C$_1$-C$_4$ alkoxy optionally substituted with one or more fluoro atoms, C$_1$-C$_4$ thioalkoxy optionally substituted with one or more fluoro atoms, —SO$_2$(C$_1$-C$_4$ alkyl), —C(=O)OR, —NRR, and —C(=O)NRR;

Q is S, S(=O), S(=O)$_2$, O or NR;

each occurrence of R is independently H or C$_1$-C$_4$ alkyl;

R$^1$ is selected from the group consisting of H, C$_1$-C$_4$ alkyl optionally substituted with one or more fluoro atoms, C$_3$-C$_6$ cycloalkyl optionally substituted with one or more fluoro atoms, aryl, substituted aryl, heteroaryl, substituted heteroaryl, arylalkyl, substituted arylalkyl, heteroarylalkyl, substituted heteroarylalkyl, heteroalkyl, substituted heteroalkyl, —C(=O)OR, and —C(=O)NRR;

R$^2$ is selected from the group consisting of —C(=O)N(R)C(=O)NR$^3$R$^4$, —C(=O)N(R)C(=O)OR$^3$ and

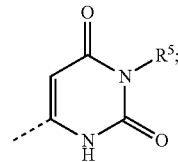

R$^3$ is selected from the group consisting of H, C$_1$-C$_4$ alkyl optionally substituted with one or more fluoro atoms, C$_3$-C$_6$ cycloalkyl optionally substituted with one or more fluoro atoms, aryl, substituted aryl, heteroaryl, substituted heteroaryl, arylalkyl, substituted arylalkyl, heteroarylalkyl, substituted heteroarylalkyl, heteroalkyl, substituted heteroalkyl, —C(=O)OR and —C(=O)NRR;

R$^4$ is H or C$_1$-C$_4$ alkyl, or R$^3$ and R$^4$ are taken together with the N atom to which both groups are bound to form a four- to seven-membered optionally substituted heterocyclic or heteroaromatic ring; and, R$^5$ is selected from the group consisting of H and C$_1$-C$_4$ alkyl optionally substituted with at least one substituent selected from the group consisting of halo, hydroxy, C$_1$-C$_4$ alkoxy, C$_1$-C$_4$ thioalkoxy, —SO$_2$(C$_1$-C$_4$ alkyl), —C(=O)OR, —NRR and —C(=O)NRR.

In certain embodiments, the compound of formula (I) is the compound of formula (Ia), or a salt or solvate thereof:

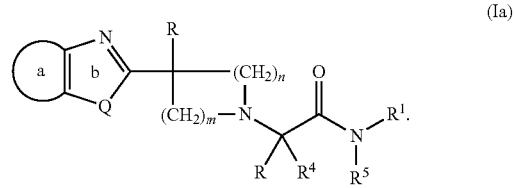

(Ia)

In certain embodiments, in (I) the bicyclic ring system ab is selected from the group consisting of:

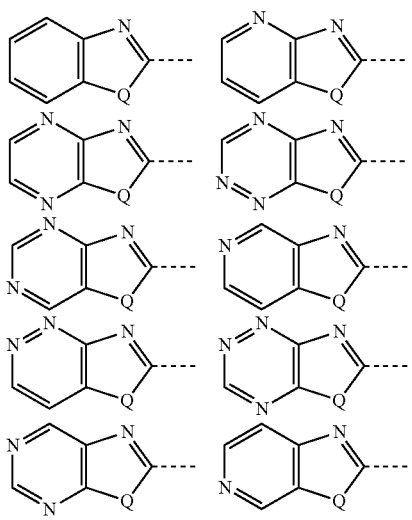

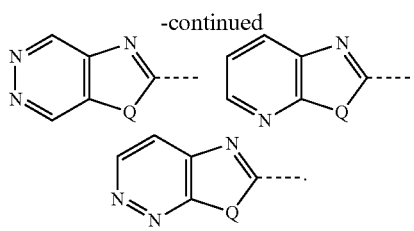

In certain embodiments, in (II) the bicyclic ring system ab is selected from the group consisting of:

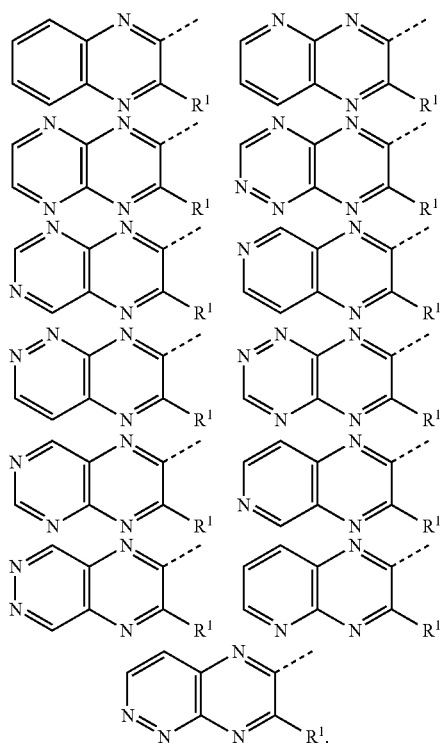

In certain embodiments, the compound of formula (I) is not selected from the group consisting of: 2-(3-(benzo[d]thiazol-2-yl)piperidin-1-yl)-N-((2,2,2-trifluoroethyl)carbamoyl)acetamide (1); 2-(3-(benzo[d]thiazol-2-yl)piperidin-1-yl)-N-(3,5-dimethyl-1H-pyrazol-4-yl)acetamide (2); 2-(3-(benzo[d]thiazol-2-yl)piperidin-1-yl)-N-(2-phenoxyethyl)acetamide (2e); 2-(3-(benzo[d]thiazol-2-yl)piperidin-1-yl)-N-(3,5-dimethyl-1-phenyl-1H-pyrazol-4-yl)acetamide (4); 3-[4-(1H-benzimidazol-2-yl)-1-piperidinyl]-1-(1-methyl-1H-pyrazol-4-yl)-2-pyrrolidinone; 3-[3-(1H-benzimidazol-2-yl)-1-piperidinyl]-1-(1-methyl-1H-pyrazol-4-yl)-2-pyrrolidinone; 4-(2-benzoxazolyl)-N-(3,5-dimethyl-1-phenyl-1H-pyrazol-4-yl)-1-piperidineacetamide; 4-(5-chloro-2-benzoxazolyl)-N-(1,3,5-trimethyl-1H-pyrazol-4-yl)-1-piperidineacetamide; 2-(6-fluoro-1H-benzimidazol-2-yl)-N-(1-methyl-1H-pyrazol-4-yl)-1-pyrrolidineacetamide; 4-(2-benzothiazolyl)-N-[3,5-dimethyl-1-(4-methylphenyl)-1H-pyrazol-4-yl]-1-piperidine acetamide; 4-(2-benzoxazolyl)-N-(1,3,5-trimethyl-1H-pyrazol-4-yl)-1-piperidineacetamide; 4-(2-benzoxazolyl)-N-[3,5-dimethyl-1-(4-methylphenyl)-1H-pyrazol-4-yl]-1-piperidine acetamide; N-(1-ethyl-3,5-dimethyl-1H-pyrazol-4-yl)-4-(7-methyl-1H-benzimidazol-2-yl)-1-piperidine acetamide; N-(1-ethyl-3,5-dimethyl-1H-pyrazol-4-yl)-2-(6-methyl-1H-benzimidazol-2-yl)-1-pyrrolidine acetamide; 4-(5-chloro-2-benzoxazolyl)-α-methyl-N-(1,3,5-trimethyl-1H-pyrazol-4-yl)-1-piperidine acetamide; 3-(2-benzoxazolyl)-α-methyl-N-(1,3,5-trimethyl-1H-pyrazol-4-yl)-1-piperidineacetamide; 3-[1-(1-methylethyl)-1H-benzimidazol-2-yl]-N-(1-methyl-1H-pyrazol-4-yl)-1-piperidine acetamide; 3-(2-benzoxazolyl)-α-methyl-N-(1,3,5-trimethyl-1H-pyrazol-4-yl)-1-piperidineacetamide; 3-[1-(1-methylethyl)-1H-benzimidazol-2-yl]-N-(1-ethyl-3-methyl-1H-pyrazol-4-yl)-1-piperidineacetamide; 3-(1H-benzimidazol-2-yl)-N-(1-ethyl-3-1H-pyrazol-4-yl)-1-piperidineacetamide; N-(1,5-dimethyl-1H-pyrazol-4-yl)-3-(1-methyl-1H-benzimidazol-2-yl)-1-piperidineacetamide; 3-[1-(1-methylethyl)-1H-benzimidazol-2-yl]-N-(1,3,5-trimethyl-1H-pyrazol-4-yl)-1-piperidine acetamide; 3-(1H-benzimidazol-2-yl)-N-(1-ethyl-3,5-dimethyl-1H-pyrazol-4-yl)-1-piperidine acetamide; N-(1-ethyl-3,5-dimethyl-1H-pyrazol-4-yl)-3-(1-methyl-1H-benzimidazol-2-yl)-1-piperidineacetamide; N-(1,3-dimethyl-1H-pyrazol-4-yl)-3-(1-methyl ethyl)-1H-benzimidazol-2-yl]-1-piperidineacetamide; N-(1-ethyl-3-methyl-1H-pyrazol-4-yl)-3-[1-(1-methylethyl)-1H-benzimidazol-2-yl]-1-piperidineacetamide; N-(1-ethyl-3-methyl-1H-pyrazol-4-yl)-3-(1-methyl-1H-benzimidazol-2-yl)-1-piperidineacetamide; 3-(1-methyl-1H-benzimidazol-2-yl)-N-(1-methyl-1H-pyrazol-4-yl)-1-piperidineacetamide; 3-(1-methyl-1H-benzimidazol-2-yl)-N-(1,3,5-trimethyl-1H-pyrazol-4-yl)-1-piperidineacetamide; N-(1-ethyl-3,5-dimethyl-1H-pyrazol-4-yl)-3-[(1-methylethyl)-1H-benzimidazol-2-yl]-1-piperidine acetamide; 2-(2-benzothiazolyl)-N-(1,3,5-trimethyl-1H-pyrazol-4-yl)-1-pyrrolidineacetamide; 2-(2-benzothiazolyl)-N-(3,5-dimethyl-1-phenyl-1H-pyrazol-4-yl)-1-pyrrolidineacetamide; 2-(4-(benzo[d]thiazol-2-yl)piperazin-1-yl)-N-(3,5-dimethyl-1H-pyrazol-4-yl)acetamide (2g); 4-(2-benzothiazolyl)-N-(3,5-dimethyl-1-phenyl-1H-pyrazol-4-yl)-1-piperidineacetamide (2h); and, (4-(benzo[d]thiazol-2-yl)piperidin-1-yl)(3,5-dimethyl-1-phenyl-1H-pyrazol-4-yl) methanone (2k)

In certain embodiments, the compound of formula (II) is not selected from the group consisting of 2-((3-methylquinoxalin-2-yl)thio)-N-((2,2,2-trifluoroethyl)carbamoyl) acetamide (3); 2-((3-methylquinoxalin-2-yl)thio)-N-(phenylcarbamoyl)acetamide (5); 2-((3-methylquinoxalin-2-yl)thio)-N-((thiophen-2-ylmethyl)carbamoyl)acetamide (3i); N-[(cyclopentylamino)carbonyl]-2-[(3-methyl-2-quinoxalinyl)thio]-acetamide; N-[(ethylamino)carbonyl]-2-[(3-methyl-2-quinoxalinyl)thio]-propanamide; N-[(methylamino)carbonyl]-2-[(3-methyl-2-quinoxalinyl)thio]-propanamide; N-[aminocarbonyl]-2-[(3-methyl-2-quinoxalinyl)thio]-3-methyl-butanamide; N-[(methylamino)carbonyl]-2-(2-quinoxalinylthio)-propanamide; N-[(ethylamino)carbonyl]-2-(2-quinoxalinylthio)-propanamide; N-[[(1-methylethyl)amino]carbonyl]-2-(2-quinoxalinylthio)-propanamide; N-[[(phenylmethyl)amino]carbonyl]-2-(2-quinoxalinyloxy)-acetamide; N-[[(1-methylethyl)amino]carbonyl]-2-(2-quinoxalinyloxy)-acetamide; ethyl (2-((3-methylquinoxalin-2-yl)thio)acetyl)carbamate (3y); and, ethyl 2-((3-methylquinoxalin-2-yl)thio)acetate (3z).

In certain embodiments, the compound of formula (I) is at least one selected from the group consisting of: 2-(3-(benzo[d]thiazol-2-yl)piperidin-1-yl)-N-((2,2,2-trifluoroethyl)carbamoyl)acetamide (1); 2-(3-(benzo[d]thiazol-2-yl)piperidin-1-yl)-N-(3,5-dimethyl-1H-pyrazol-4-yl)acetamide (2); 2-(3-(benzo[d]thiazol-2-yl)piperidin-1-yl)-N-(2-phenoxyethyl)acetamide (2e); and, 2-(3-(benzo[d]thiazol-2-yl)piperidin-1-yl)-N-(3,5-dimethyl-1-phenyl-1H-pyrazol-4-yl)acetamide (4).

In certain embodiments, the compound of formula (I) is at least one selected from the group consisting of: (4-Benzothiazol-2-yl-piperidin-1-yl)-(3,5-dimethyl-1H-pyrazol-4-yl)-methanone (2i); (4-(benzo[d]thiazol-2-yl)piperidin-1-yl)(1,3,5-trimethyl-1H-pyrazol-4-yl)methanone (2j); 2-[1-(1,3,5-Trimethyl-1H-pyrazol-4-ylmethyl)-piperidin-4-yl]-benzothiazole (2l); and, 2-[1-(3,5-Dimethyl-1-phenyl-1H-pyrazol-4-ylmethyl)-piperidin-4-yl]-benzothiazole (2m).

In certain embodiments, the compound of formula (I) is at least one selected from the group consisting of: 2-(3-(benzo[d]thiazol-2-yl)piperidin-1-yl)-N-2,2,2-trifluoroethyl)carbamoyl)acetamide (1); 2-(3-(benzo[d]thiazol-2-yl)piperidin-1-yl)-N-(3,5-dimethyl-1H-pyrazol-4-yl)acetamide (2); 2-(3-(benzo[d]thiazol-2-yl)piperidin-1-yl)-N-(2-phenoxyethypacetamide (2e); 2-(3-(benzo[d]thiazol-2-yl)piperidin-1-yl)-N-(3,5-dimethyl-1-phenyl-1H-pyrazol-4-yl)acetamide (4); (4-Benzothiazol-2-yl-piperidin-1-yl)-(3,5-dimethyl-1H-pyrazol-4-yl)-methanone (2i); (4-(benzo[d]thiazol-2-yl)piperidin-1-yl)(1,3,5-trimethyl-1H-pyrazol-4-yl)methanone (2j); 2-[1-(1,3,5-Trimethyl-1H-pyrazol-4-ylmethyl)-piperidin-4-yl]-benzothiazole (2l); and, 2-[1-(3,5-Dimethyl-1-phenyl-1H-pyrazol-4-ylmethyl)-piperidin-4-yl]-benzothiazole (2m).

In certain embodiments, the compound of formula (II) is at least one selected from the group consisting of: N-(ethylcarbamoyl)-2-((3-methylquinoxalin-2-yl)thio) acetamide (3f); N-(cyclopropylcarbamoyl)-2-((3-methylquinoxalin-2-yl)thio)acetamide (3g); 6-(3-Methyl-quinoxalin-2-ylsulfanylmethyl)-1H-pyrimidine-2,4-dione (3n); N-(benzylcarbamoyl)-2-((3-methylquinoxalin-2-yl)thio)acetamide (3o); 2-((3-methyl quinoxalin-2-yl)thio)-N-(pyridin-2-ylcarbamoyl)acetamide (3p); 2-((3-methylquinoxalin-2-yl)thio)-N-(pyridin-3-ylcarbamoyl)acetamide (3q); N-((1H-pyrazol-3-yl)carbamoyl)-2-((3-methylquinoxalin-2-yl)thio)acetamide (3r); N-((3,5-dimethyl-1H-pyrazol-4-yl)carbamoyl)-2-((3-methylquinoxalin-2-yl)thio)acetamide (3s); 2-((3-methylquinoxalin-2-yl)thio)-N-((1,3,5-trimethyl-1H-pyrazol-4-yl)carbamoyl)acetamide (3t); N-((2-fluorophenyl)carbamoyl)-2-((3-methylquinoxalin-2-yl)thio)acetamide (3u); N-((3-fluorophenyl)carbamoyl)-2-((3-methylquinoxalin-2-yl)thio)acetamide (3v); N-((4-fluorophenyl)carbamoyl)-2-((3-methylquinoxalin-2-yl)thio)acetamide (3w); 1-[2-(3-methyl-quinoxalin-2-yloxy)-acetyl]-3-phenyl-urea (3x); 1-Methyl-3-[2-(3-methyl-quinoxalin-2-ylsulfanyl)-acetyl]-1-phenyl-urea (3aa); 1-[2-(3-Benzyl-quinoxalin-2-ylsulfanyl)-acetyl]-3-(3,5-dimethyl-1H-pyrazol-4-yl)-urea (3ab); 2-((3-benzylquinoxalin-2-yl)thio)-N-1,3,5-trimethyl-1H-pyrazol-4-yl)carbamoyl acetamide (3ac); and, 2-((3-benzylquinoxalin-2-yl)thio)-N-((4-fluorophenyl)carbamoyl) acetamide (3ad).

In certain embodiments, the compound of formula (II) is at least one selected from the group consisting of: 2-((3-methylquinoxalin-2-yl)thio)-N-((2,2,2-trifluoroethyl) carbamoyl) acetamide (3); 2-((3-methylquinoxalin-2-yl)thio)-N-(phenylcarbamoyl)acetamide (5); and, 2-((3-methylquinoxalin-2-yl)thio)-N-((thiophen-2-ylmethyl) carbamoyl)acetamide (3i).

In certain embodiments, the compound of formula (II) is at least one selected from the group consisting of: 2-((3-methylquinoxalin-2-yl)thio)-N-((2,2,2-trifluoroethyl) carbamoyl) acetamide (3); N-(ethylcarbamoyl)-2-((3-methylquinoxalin-2-yl)thio)acetamide (3f); N-(cyclopropylcarbamoyl)-2-((3-methylquinoxalin-2-yl)thio)acetamide (3g); 2-((3-methylquinoxalin-2-yl)thio)-N-(phenylcarbamoyl)acetamide (5); 2-((3-methylquinoxalin-2-yl)thio)-N-((thiophen-2-ylmethyl)carbamoyl)acetamide (3i); 6-(3-Methyl-quinoxalin-2-ylsulfanylmethyl)-1H-pyrimidine-2,4-dione (3n); N-(benzylcarbamoyl)-2-((3-methyl quinoxalin-2-yl)thio)acetamide (3o); 2-((3-methylquinoxalin-2-yl)thio)-N-(pyridin-2-ylcarbamoyl)acetamide (3p); 2-((3-methylquinoxalin-2-yl)thio)-N-(pyridin-3-ylcarbamoyl)acetamide (3q); N-((1H-pyrazol-3-yl)carbamoyl)-2-((3-methylquinoxalin-2-yl)thio)acetamide (3r); N-((3,5-dimethyl-1H-pyrazol-4-yl)carbamoyl)-2-((3-methylquinoxalin-2-yl)thio)acetamide (3s); 2-((3-methylquinoxalin-2-yl)thio)-N-((1,3,5-trimethyl-1H-pyrazol-4-yl)carbamoyl) acetamide (3t); N-((2-fluorophenyl)carbamoyl)-2-((3-methylquinoxalin-2-yl)thio)acetamide (3u); N-((3-fluorophenyl)carbamoyl)-2-((3-methylquinoxalin-2-yl)thio) acetamide (3v); N-((4-fluorophenyl)carbamoyl)-2-((3-methylquinoxalin-2-yl)thio)acetamide (3w); 1-[2-(3-Methyl-quinoxalin-2-yloxy)-acetyl]-3-phenyl-urea (3x); 1-Methyl-3-[2-(3-methyl-quinoxalin-2-ylsulfanyl)-acetyl]-1-phenyl-urea (3aa); 1-[2-(3-Benzyl-quinoxalin-2-ylsulfanyl)-acetyl]-3-(3,5-dimethyl-1H-pyrazol-4-yl)-urea (3ab); 2-((3-benzylquinoxalin-2-yl) thio)-N-((1,3,5-trimethyl-1H-pyrazol-4-yl)carbamoyl)acetamide (3ac); and, 2-((3-benzyl quinoxalin-2-yl)thio)-N-((4-fluorophenyl)carbamoyl)acetamide (3ad).

In certain embodiments, the at least one compound is selected from the group consisting of: 2-(3-(benzo[d]thiazol-2-yOpiperidin-1-yl)-N-(3,5-dimethyl-1H-pyrazol-4-yl) acetamide (2); 2-(3-(benzo[d]thiazol-2-yOpiperidin-1-yl)-N-(2-phenoxyethyl)acetamide (2e); and, 2-(3-(benzo[d]thiazol-2-yOpiperidin-1-yl)-N-(3,5-dimethyl-1-phenyl-1H-pyrazol-4-yl) acetamide (4); (4-B enzothiazol-2-yl-piperidin-l-yl)-(3,5 -dimethyl-1H-py razol-4-yl)-methanone (2i); (4-(benzo[d]thiazol-2-yOpiperidin-1-yl)(1,3,5-trimethyl-1H-pyrazol-4-yl) methanone (2j); 2-[1-(1,3,5-Trimethyl-1H-pyrazol-4-ylmethyl)-piperidin-4-yl]-benzothiazole (2l); 2-[1-(3,5-Dimethyl-1-phenyl-1H-pyrazol-4-ylmethyl)-piperidin-4-yl]-benzothiazole (2m); 2-((3-methylquinoxalin-2-yl)thio)-N-((2,2,2-trifluoroethyl) carbamoyl) acetamide (3); N-(ethylcarbamoyl)-2-((3-methylquinoxalin-2-yl)thio)acetamide (3f); N-(cyclopropyl carbamoyl)-2-((3-methylquinoxalin-2-yl)thio)acetamide (3g); 2-((3-methyl quinoxalin-2-yl)thio)-N-(phenylcarbamoyl)acetamide (5); 2-((3-methylquinoxalin-2-yl)thio)-N-((thiophen-2-ylmethyl)carbamoyl)acetamide (3i); 6-Methyl-quinoxalin-2-ylsulfanyl methyl)-1H-pyrimidine-2,4-dione (3n); N-(benzylcarbamoyl)-2-((3-methyl quinoxalin-2-yl)thio) acetamide (3o); 2-((3-methylquinoxalin-2-yl)thio)-N-(pyridin-2-ylcarbamoyl)acetamide (3p); 2-((3-methylquinoxalin-2-yl)thio)-N-(pyridin-3-ylcarbamoyl)acetamide (3q); N-((1H-pyrazol-3-yl)carbamoyl)-2-((3-methylquinoxalin-2-yl)thio)acetamide (3r); N-((3,5-dimethyl-1H-pyrazol-4-yl)carbamoyl)-2-((3-methylquinoxalin-2-yl)thio)acetamide (3s); 2-((3-methyl quinoxalin-2-yl) thio)-N-((1,3,5-trimethyl-1H-pyrazol-4-yl)carbamoyl) acetamide (3t); N-((2-fluorophenyl)carbamoyl)-2-((3-methylquinoxalin-2-yl)thio)acetamide (3u); N-((3-fluorophenyl)carbamoyl)-2-((3-methylquinoxalin-2-yl)thio) acetamide (3v); N-((4-fluorophenyl)carbamoyl)-2-((3-methylquinoxalin-2-yl)thio)acetamide (3w); 1-[2-(3-Methyl-quinoxalin-2-yloxy)-acetyl]-3-phenyl-urea (3x); ethyl (2-((3-methylquinoxalin-2-yl)thio) acetyl)carbamate (3y); ethyl 2-((3-methylquinoxalin-2-yl)thio)acetate (3z); 1-Methyl-3-[2-(3-methyl-quinoxalin-2-ylsulfanyl)-acetyl]-1-phenyl-urea (3aa); 1-[2-(3-Benzyl-quinoxalin-2-ylsulfanyl)-acetyl]-3-(3,5-dimethyl-1H-pyrazol-4-yl)-urea (3ab); 2-((3-benzylquinoxalin-2-yl)thio)-N-1,3,5-trimethyl-1H- pyrazol-4-yl)carbamoyl)acetamide (3ac); and, 2-((3-benzylquinoxalin-2-yl)thio)-N-((4-fluorophenyl)carbamoyl)acetamide (3ad).

In certain embodiments, the composition further comprises at least one additional antiviral agent. In other embodiments, the compound and the at least one additional agent are coformulated in the composition.

In certain embodiments, the method comprises administering to subject a therapeutically effective amount of at least one compound of the invention, or salt or solvate thereof.

In certain embodiments, the compound interferes with viral budding within the subject. In other embodiments, the compound interferes with the interaction of the subject's Nedd4 E3 ubiquitin ligase and at least one viral budding domain. In yet other embodiments, the compound disrupts or prevents virus budding within the subject. In yet other embodiments, the compound disrupts or prevents virus dissemination within the subject. In other embodiments, the compound blocks at least one selected from the group consisting of viral disease progression and viral disease transmission. In other embodiments, the viral infection is caused by at least one virus selected from the group consisting of a filovirus, arenavirus, rhabdovirus, paramyxovirus, and retrovirus.

In certain embodiments, the subject is further administered at least one additional antiviral agent. In other embodiments, the subject is co-administered the compound and the at least one additional agent. In yet other embodiments, the compound and the at least one additional agent are coformulated. In yet other embodiments, the subject is a mammal. In yet other embodiments, the mammal is human.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIGS. 2A-2B illustrate the effect of 1 on PPxY-dependent budding of MARV VP40 VLPs and live VSV. FIG. 2A: HEK293T cells transfected with pCAGGS vector (lane 1) or mVP40 (lanes 2-6) were treated with DMSO alone (lanes 1 and 2), or with the indicated concentrations of compound 1 (lanes 3-6). Cells and VLPs were harvested at 24 hours post-transfection, and a representative Western blot to detect mVP40 is illustrated. A Western blot control for β-actin in cells is illustrated. The bar graph showing mVP40 levels (Image J software) in VLPs from samples receiving 0 and 20 μM of 1 represents the average from three independent experiments. FIG. 2B: HEK293T cells were infected with VSV-WT (black) or VSV-PY>A4 (gray) at an MOI of 0.1 in the absence (DMSO alone) or presence of 10 μM 1. Supernatants were harvested at 8 hours post-infection, and virions were quantified by standard plaque assay on BHK-21 cells performed in triplicate and graphed as relative release efficiency. Infected cells extracts were harvested at 8 hours post-infection, and both VSV M and cellular actin were detected by Western blotting.

FIG. 4A: HEK293T cells transfected with mVP40 were treated with DMSO alone (lane 1), or with the indicated concentrations of 4 (lanes 2-4). Cells and VLPs were harvested at 24 hours post-transfection, and a representative Western blot for mVP40 is illustrated. Western blot controls for cellular GAPDH and HSP70 in cells are illustrated. The bar graph represents the average levels (Image J software) of mVP40 VLPs from three independent experiments. FIG. 4B: HEK293T cells transfected with eVP40 were treated with DMSO alone (lane 1), or with the indicated concentrations of 4 (lanes 2 and 3). Cells and VLPs were harvested at 24 hours post-transfection, and a representative Western blot for eVP40 is illustrated. Western blot controls for cellular GAPDH and HSP70 in cells are illustrated. The bar graph represents the average levels (Image J software) of eVP40 VLPs from three independent experiments. FIG. 4C: BiMC assay and representative images of HEK293T cells co-expressing NYFP-Nedd4 and CYFP-mVP40 fusion proteins in the absence (DMSO alone), or presence of the indicated concentrations of 4 or 6. The green signal represents an interaction between mVP40 and Nedd4, and cell nuclei were stained blue with NucBlue. Bar=200 μm.

FIG. 5A: HEK293T cells transfected with mVP40 were treated with DMSO alone (lane 1), or with the indicated concentrations of 5 (lanes 2-4). Cells and VLPs were harvested at 24 hours post-transfection, and a representative Western blot for mVP40 is illustrated. Western blot controls for cellular GAPDH and HSP70 in cells are illustrated. The bar graph represents the average levels (Image J software) of mVP40 VLPs from three independent experiments. FIG. 5B: HEK293T cells transfected with eVP40 were treated with DMSO alone (lane 1), or with the indicated concentrations of 5 (lanes 2-4). Cells and VLPs were harvested at 24 hours post-transfection, and a representative Western blot for eVP40 is illustrated. Western blot controls for cellular GAPDH and HSP70 in cells are illustrated. The bar graph represents the average levels (Image J software) of eVP40 VLPs from three independent experiments. FIG. 5C: BiMC assay and representative images of HEK293T cells co-expressing NYFP-Nedd4 and CYFP-mVP40 fusion proteins in the absence (DMSO alone), or presence of the indicated concentrations of 5. The green signal represents an interaction between mVP40 and Nedd4, and cell nuclei were stained blue with NucBlue. Bar=200 µm.

FIGS. 6A-6C illustrate the finding that Compounds 4 and 5 inhibit budding of LFV Z VLPs. FIG. 6A: VLP budding assay and Western blot demonstrating that the PPxY L-domain motif of LFV Z protein is important for efficient VLP egress from HEK293T cells. Budding of LFV Z-ΔPPPY VLPs was reduced by 4-fold compared to that of LFV-Z-WT. HEK293T cells transfected with LFV Z-WT were treated with DMSO alone (0), or with the indicated concentrations of 4 (FIG. 6B) or 5 (FIG. 6C). Cells and VLPs were harvested at 24 hours post-transfection, and LFV Z-WT was detected by Western blot. Western blot loading controls for cellular actin are illustrated.

FIG. 7A: HEK293T cells were infected with VSV-WT, VSV-M40, or VSV-PY/A4 at an MOI of 0.1 in the absence (DMSO alone) or presence of 0.1 or 0.5 µM 4. Supernatants were harvested at 8 hours post-infection, and virions were quantified by standard plaque assay on BHK-21 cells performed in triplicate. *=p value<0.5 and **=p value<0.01 as determined by a one way ANOVA test. Infected cells extracts were harvested at 8 hours post-infection, and VSV M, GAPDH, and HSP70 were detected by Western blotting. FIG. 7B: HEK293T cells were infected with VSV-WT, VSV-M40, or VSV-PY/A4 at an MOI of 0.1 in the absence (DMSO alone) or presence of 0.1 µM or 0.5 µM 5. Supernatants were harvested at 8 hours post-infection, and virions were quantified by standard plaque assay on BHK-21 cells performed in triplicate. *=p value<0.5 and **=p value<0.01 as determined by a one way ANOVA test. Infected cells extracts were harvested at 8 hours post-infection, and VSV M, GAPDH, and HSP70 were detected by Western blotting.

FIG. 8C: Western blot analysis of RABV infected HEK293T cells in the absence (DMSO alone) or presence of the indicated concentrations of 4 and 5. Cell extracts were harvested at 36 hours p.i., and detection of RABV M protein (24 kDa) by Western blotting is illustrated.

FIGS. 9A-9B illustrate a diagram of arenavirus, filovirus, and rhabdovirus virions budding efficiently from the plasma membrane in the absence of inhibitors (FIG. 9A), or remaining tethered to the plasma membrane (FIG. 9B) as a result of PPxY inhibitors blocking the interaction between host Nedd4 and the PPxY L-domains present in the Z, VP40, and M viral matrix proteins.

FIG. 11 is a table that illustrates budding, BiMC, VSV assays and MW/logP/TPSA properties for selected compounds of the invention.

FIG. 12A: VLP budding assay for Marburg VP40 (mVP40) in HEK293T cells in the absence (DMSO alone), or presence of compound 4 at 0.1, 0.5, or 1.0 µM. Equivalent amounts of mVP40 and host protein GAPDH were observed in cell extracts (Cells) under all conditions; however, budding of mVP40 VLPs was reduced by >90% in cells treated with compound 4 at 0.5 or 1.0 µM. FIG. 12B: BiMC assay showing the PPxY-dependent interaction between mVP40 and host Nedd4 (green cells) in the absence (DMSO alone), or presence of compound 4 at 0.5 or 1.0 µM. Equivalent numbers of cells are present under all conditions as determined by quantification of Hoechst stained nuclei (blue). FIG. 12C: HEK293T cells were infected with WT VSV in the absence (DMSO alone), or presence of compound 4 at 0.1 or 0.5 µM concentrations. Cell extracts and supernatants (containing budded virions) were harvested at 8 hours post-infection. Budded virions were quantified by plaque assay performed in triplicate on BHK-21 cells, and both VSV M and host GAPDH proteins in infected cells were quantified by Western blotting. Compound 4 had no effect on protein synthesis at the concentrations tested; however, PPxY-dependent budding of VSV was reduced by approximately 50% and 100% at 0.1 and 0.5 µM concentrations of compound 4, respectively.

DETAILED DESCRIPTION OF THE INVENTION

Figure 1:
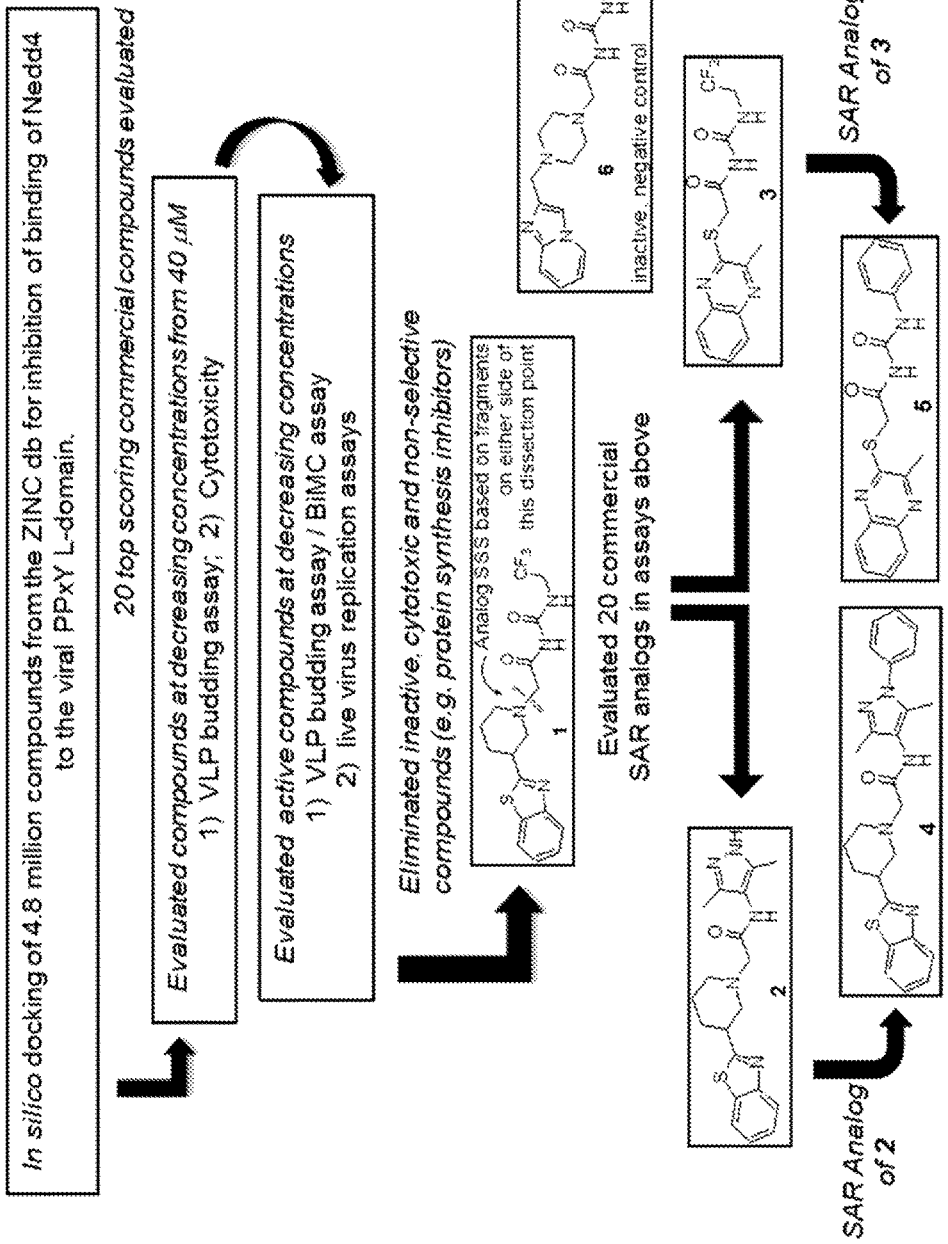
FIG. 1 is a non-limiting illustration of a strategy contemplated within the invention for identifying PPxY budding inhibitors. The flow chart illustrates an in silico screen and SAR analysis to identify inhibitors of the viral PPxY-host Nedd4 interaction and PPxY-mediated budding. The in silico screen involved computational docking with AutoDock 4.0, energy minimization using CHARMM with the MMFF force field, and ranking with Accelrys LigScore2 of 4.8 million drug-like compounds from the ZINC database. The top 20 scoring compounds were tested as indicated leading to the identification of the lead 1. The lead 1 was dissected into two fragments and twenty commercially available compounds having these two fragment substructures (ten compounds from each) were evaluated. Two compounds (2 and 3), one from each substructure search, were found to be more potent than 1. Compound 4 showed improved potency over SAR analog 2, and 5 showed improved potency over SAR analog 3. Compound 6 is a control compound.

The present invention relates to the unexpected discovery that the compounds of the invention are antiviral agents. In one aspect, the compounds of the invention interfere with viral budding. In certain embodiments, the compounds of the invention interfere with the interaction of the host Nedd4 E3 ubiquitin ligase and at least one viral budding domain. In other embodiments, the compounds of the invention disrupt or hamper virus budding. In yet other embodiments, the compounds of the invention prevent or hamper virus dissemination. In yet other embodiments, the compounds of the invention block viral disease progression and/or transmission.

In certain embodiments, the compounds of the invention treat or prevent a viral infection in a subject. In other embodiments, the viral infection is caused by at least one single strand RNA virus. In yet other embodiments, the infection is caused by at least one virus selected from the group consisting of a Filovirus (such as, but not limited to, Ebola or Marburg virus), arenavirus (such as, but not limited to, Lassas fever virus), rhaddovirus (such as, but not limited to, rabies, vesicular stomatitis, or emerging lyssavirus), paramyxovirus (such as, but not limited to, Nipah or Hendra virus), retrovirus (such as, but not limited to, HIV-1, HIV-2, or human T-cell leukemia virus, also known as HTLV-1), and any combinations thereof. In other embodiments, the subject is a mammal.

As described herein, budding of filoviruses, arenaviruses, and rhabdoviruses is facilitated by subversion of host proteins, such as Nedd4 E3 ubiquitin ligase, by viral PPxY late (L) budding domains expressed within the matrix proteins of these RNA viruses. As L domains are important for budding and are highly conserved in a wide array of RNA viruses, they represent potential broad-spectrum targets for the development of antiviral drugs. Without wishing to be limited by any theory, the Nedd4 WW-domain/PPxY interaction interface was used as the basis of an in silico screen for inhibitors. Using PPxY-dependent budding of Marburg (MARV) VP40 virus-like particles (VLPs) as the model system, compound 1, which inhibited Nedd4-PPxY interaction and PPxY-dependent budding, was identified. Optimization of this compound, with enhancement of anti-budding activity, allowed for the identification of compounds 4 and 5. These compounds exhibit on-target effects by specifically blocking the MARV VP40 PPxY-host Nedd4 interaction and subsequent PPxY-dependent egress of MARV VP40 VLPs. In addition, compounds 4 and 5 exhibited anti-budding activity against Ebola and Lassa fever VLPs, as well as live vesicular stomatitis (VSV) and rabies (RABV) viruses. These data indicate that inhibition of the PPxY-Nedd4 interaction can serve as the basis for the development of a novel class of broad-spectrum, host-oriented antiviral compounds targeting viruses that depend on a functional PPxY L domain for efficient egress.

Definitions

As used herein, each of the following terms has the meaning associated with it in this section. Unless defined otherwise, all technical and scientific terms used herein generally have the same meaning as commonly understood by one of ordinary skill in the art to which this invention belongs. Generally, the nomenclature used herein and the laboratory procedures in animal pharmacology, pharmaceutical science, virology and organic chemistry are those well-known and commonly employed in the art.

As used herein, the articles "a" and "an" refer to one or to more than one (i.e. to at least one) of the grammatical object of the article. By way of example, "an element" means one element or more than one element.

As used herein, the term "about" is understood by persons of ordinary skill in the art and varies to some extent on the context in which it is used. As used herein when referring to a measurable value such as an amount, a temporal duration, and the like, the term "about" is meant to encompass variations of ±20% or ±10%, in certain embodiments ±5%, in certain embodiments ±1%, and in certain embodiments ±0.1% from the specified value, as such variations are appropriate to perform the disclosed methods.

In one aspect, the terms "co-administered" and "co-administration" as relating to a subject refer to administering to the subject a compound of the invention or salt thereof along with a compound that may also treat a disease or disorder contemplated within the invention. In certain embodiments, the co-administered compounds are administered separately, or in any kind of combination as part of a single therapeutic approach. The co-administered compound may be formulated in any kind of combinations as mixtures of solids and liquids under a variety of solid, gel, and liquid formulations, and as a solution.

As used herein, the term "composition" or "pharmaceutical composition" refers to a mixture of at least one compound useful within the invention with a pharmaceutically acceptable carrier. The pharmaceutical composition facilitates administration of the compound to a subject.

As used herein, a "disease" is a state of health of a subject wherein the subject cannot maintain homeostasis, and wherein if the disease is not ameliorated then the subject's health continues to deteriorate.

As used herein, a "disorder" in a subject is a state of health in which the subject is able to maintain homeostasis, but in which the subject's state of health is less favorable than it would be in the absence of the disorder. Left untreated, a disorder does not necessarily cause a further decrease in the subject's state of health.

As used herein, the term "EBOV" refers to Ebola viruses.

As used herein, the term "ESCRT" complex refers to endosomal sorting complex required for transport.

As used herein, an "effective amount," "therapeutically effective amount" or "pharmaceutically effective amount" of a compound is that amount of compound that is sufficient to provide a beneficial effect to the subject to which the compound is administered.

"Instructional material" as that term is used herein includes a publication, a recording, a diagram, or any other medium of expression that can be used to communicate the usefulness of the composition and/or compound of the invention in a kit. The instructional material of the kit may, for example, be affixed to a container that contains a compound and/or composition of the invention or be shipped together with a container that contains the compound and/or composition. Alternatively, the instructional material may be shipped separately from the container with the intention that the recipient uses the instructional material and the compound cooperatively. Delivery of the instructional material may be, for example, by physical delivery of the publication or other medium of expression communicating the usefulness of the kit, or may alternatively be achieved by electronic transmission, for example by means of a computer, such as by electronic mail, or download from a website.

As used herein, the term "JUNV" refers to Junin viruses.

As used herein, the term "LFV" refers to Lassa fever viruses.

As used herein, the term "MARV" refers to Marburg viruses.

As used herein, the term "pharmaceutically acceptable" refers to a material, such as a carrier or diluent, which does not abrogate the biological activity or properties of the compound useful within the invention, and is relatively non-toxic, i.e., the material may be administered to a subject without causing undesirable biological effects or interacting in a deleterious manner with any of the components of the composition in which it is contained.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the subject such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the subject. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate;

powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the invention, and are physiologically acceptable to the subject. Supplementary active compounds may also be incorporated into the compositions. The "pharmaceutically acceptable carrier" may further include a pharmaceutically acceptable salt of the compound useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

As used herein, the language "pharmaceutically acceptable salt" refers to a salt of the administered compound prepared from pharmaceutically acceptable non-toxic acids and bases, including inorganic acids, inorganic bases, organic acids, inorganic bases, solvates, hydrates, and clathrates thereof.

The term "prevent," "preventing" or "prevention," as used herein, means avoiding or delaying the onset of symptoms associated with a disease or condition in a subject that has not developed such symptoms at the time the administering of an agent or compound commences. Disease, condition and disorder are used interchangeably herein.

As used herein, the term "Nedd4" refers to mammalian E3 ubiquitin ligase neural precursor cell expressed developmentally down-regulated protein 4.

As used herein, the term "RABV" refers to rabies viruses.

By the term "specifically bind" or "specifically binds," as used herein, is meant that a first molecule preferentially binds to a second molecule (e.g., a particular receptor or enzyme), but does not necessarily bind only to that second molecule.

As used herein, a "subject" may be a human or non-human mammal or a bird. Non-human mammals include, for example, livestock and pets, such as ovine, bovine, porcine, canine, feline and murine mammals. il certain embodiments, the subject is human.

The terms "treat," "treating" and "treatment," as used herein, means reducing the frequency or severity with which symptoms of a disease or condition are experienced by a subject by virtue of administering an agent or compound to the subject.

As used herein, the term "VLPs" refers to virus-like particles.

As used herein, the term "VSV" refers to vesicular stomatitis viruses.

As used herein, the term "alkyl" by itself or as part of another substituent means, unless otherwise stated, a straight or branched chain hydrocarbon having the number of carbon atoms designated (i.e., $C_1$-$C_{10}$ means one to ten carbon atoms) and includes straight, branched chain, or cyclic substituent groups. Examples include methyl, ethyl, propyl, isopropyl, butyl, isobutyl, tert-butyl, pentyl, neopentyl, hexyl, and cyclopropylmethyl. In certain embodiments alkyl is ($C_1$-$C_6$)alkyl, such as, but not limited to, ethyl, methyl, isopropyl, isobutyl, n-pentyl, n-hexyl and cyclopropylmethyl.

As used herein, the term "cycloalkyl" by itself or as part of another substituent means, unless otherwise stated, a cyclic chain hydrocarbon having the number of carbon atoms designated (i.e., $C_3$-$C_6$ means a cyclic group comprising a ring group consisting of three to six carbon atoms) and includes straight, branched chain or cyclic substituent groups. Examples include cyclopropyl, cyclobutyl, cyclopentyl, cyclohexyl, cycloheptyl, and cyclooctyl. In certain embodiments cycloalkyl is ($C_3$-$C_6$)cycloalkyl, such as, but not limited to, cyclopropyl, cyclobutyl, cyclopentyl and cyclohexyl.

As used herein, the term "alkenyl" employed alone or in combination with other terms means, unless otherwise stated, a stable mono-unsaturated or di-unsaturated straight chain or branched chain hydrocarbon group having the stated number of carbon atoms. Examples include vinyl, propenyl (or allyl), crotyl, isopentenyl, butadienyl, 1,3-pentadienyl, 1,4-pentadienyl, and the higher homologs and isomers. A functional group representing an alkene is exemplified by —$CH_2$—CH=$CH_2$.

As used herein, the term "alkynyl" employed alone or in combination with other terms means, unless otherwise stated, a stable straight chain or branched chain hydrocarbon group with a triple carbon-carbon bond, having the stated number of carbon atoms. Non-limiting examples include ethynyl and propynyl, and the higher homologs and isomers. The term "propargylic" refers to a group exemplified by —$CH_2$—C≡CH. The term "homopropargylic" refers to a group exemplified by —$CH_2CH_2$—C≡CH. The term "substituted propargylic" refers to a group exemplified by —$CR_2$—C≡CR, wherein each occurrence of R is independently H, alkyl, substituted alkyl, alkenyl or substituted alkenyl, with the proviso that at least one R group is not hydrogen. The term "substituted homopropargylic" refers to a group exemplified by —$CR_2CR_2$—C≡CR, wherein each occurrence of R is independently H, alkyl, substituted alkyl, alkenyl or substituted alkenyl, with the proviso that at least one R group is not hydrogen.

As used herein, the term "substituted alkyl," "substituted cycloalkyl," "substituted alkenyl" or "substituted alkynyl" means alkyl, cycloalkyl, alkenyl or alkynyl, as defined above, substituted by one, two or three substituents selected from the group consisting of halogen, —OH, alkoxy, tetrahydro-2-H-pyranyl, —$NH_2$, —N($CH_3$)$_2$, (1-methyl-imidazol-2-yl), pyridin-2-yl, pyridin-3-yl, pyridin-4-yl, —C(=O)OH, trifluoromethyl, —C≡N, —C(=O)O($C_1$-$C_4$)alkyl, —C(=O)$NH_2$, —C(=O)NH($C_1$-$C_4$)alkyl, —C(=O)N(($C_1C_4$)alkyl)$_2$, —$SO_2NH_2$, —C(=NH)$NH_2$, and —$NO_2$, in certain embodiments containing one or two substituents selected from halogen, —OH, alkoxy, —$NH_2$, trifluoromethyl, —N($CH_3$)$_2$, and —C(=O)OH, in certain embodiments selected from halogen, alkoxy and —OH. Examples of substituted alkyls include, but are not limited to, 2,2-difluoropropyl, 2-carboxycyclopentyl and 3-chloropropyl.

As used herein, the term "alkoxy" employed alone or in combination with other terms means, unless otherwise stated, an alkyl group having the designated number of carbon atoms, as defined above, connected to the rest of the molecule via an oxygen atom, such as, for example, methoxy, ethoxy, 1-propoxy, 2-propoxy (isopropoxy) and the higher homologs and isomers. In certain embodiments alkoxy is ($C_1$-$C_3$)alkoxy, such as, but not limited to, ethoxy and methoxy.

As used herein, the term "halo" or "halogen" employed alone or as part of another substituent means, unless otherwise stated, a fluorine, chlorine, bromine, or iodine atom, in certain embodiments, fluorine, chlorine, or bromine, in other embodiments, fluorine or chlorine.

As used herein, the term "heteroalkyl" by itself or in combination with another term means, unless otherwise stated, a stable straight or branched chain alkyl group consisting of the stated number of carbon atoms and one or two heteroatoms selected from the group consisting of O, N, and S, and wherein the nitrogen and sulfur atoms may be optionally oxidized and the nitrogen heteroatom may be optionally quaternized. The heteroatom(s) may be placed at any position of the heteroalkyl group, including between the rest of the heteroalkyl group and the fragment to which it is attached, as well as attached to the most distal carbon atom in the heteroalkyl group. Examples include: —O—$CH_2$—$CH_2$—$CH_3$, —$CH_2$—$CH_2$—$CH_2$—OH, —$CH_2$—$CH_2$—NH—$CH_3$, —$CH_2$—S—$CH_2$—$CH_3$, and —$CH_2CH_2$—S(=O)—$CH_3$. Up to two heteroatoms may be consecutive, such as, for example, —$CH_2$—NH—$OCH_3$, or —$CH_2$—$CH_2$—S—S—$CH_3$ As used herein, the term "heteroalkenyl" by itself or in combination with another term means, unless otherwise stated, a stable straight or branched chain monounsaturated or di-unsaturated hydrocarbon group consisting of the stated number of carbon atoms and one or two heteroatoms selected from the group consisting of O, N, and S, and wherein the nitrogen and sulfur atoms may optionally be oxidized and the nitrogen heteroatom may optionally be quaternized. Up to two heteroatoms may be placed consecutively. Examples include —CH=CH—O—$CH_3$, —CH=CH—$CH_2$—OH, —$CH_2$—CH=N—$OCH_3$, —CH=CH—N($CH_3$)—$CH_3$, and —$CH_2$—CH=CH—$CH_2$—SH.

As used herein, the term "aromatic" refers to a carbocycle or heterocycle with one or more polyunsaturated rings and having aromatic character, i.e. having (4n+2) delocalized π (pi) electrons, where n is an integer.

As used herein, the term "aryl" employed alone or in combination with other terms means, unless otherwise stated, a carbocyclic aromatic system containing one or more rings (typically one, two or three rings) wherein such rings may be attached together in a pendent manner, such as a biphenyl, or may be fused, such as naphthalene. Examples include phenyl, anthracyl, and naphthyl. In certain embodiments aryl is phenyl and naphthyl, in other embodiments is phenyl.

As used herein, the term "arylalkyl" means a functional group wherein an alkylene chain is attached to an aryl group, e.g., —$CH_2CH_2$-phenyl or —$CH_2$-phenyl (benzyl). In certain embodiments arylalkyl is aryl-$CH_2$— and aryl-CH($CH_3$)—. The term "substituted aryl-($C_1$-$C_3$)alkyl" means an aryl-($C_1$-$C_3$)alkyl functional group in which the aryl group is substituted; in certain embodiments, is substituted aryl($CH_2$)—. Similarly, the term "heteroarylalkyl" means a functional group wherein an alkylene chain is attached to a heteroaryl group, e.g., —$CH_2CH_2$-pyridyl; in certain embodiments is heteroaryl-($CH_2$)—. The term "substituted heteroaryl-($C_1$-$C_3$)alkyl" means a heteroaryl-($C_1$-$C_3$)alkyl functional group in which the heteroaryl group is substituted; in certain embodiments, is substituted heteroaryl-($CH_2$)—.

As used herein, the term "heterocycle" or "heterocyclyl" or "heterocyclic" by itself or as part of another substituent means, unless otherwise stated, an unsubstituted or substituted, stable, mono- or multi-cyclic heterocyclic ring system that consists of carbon atoms and at least one heteroatom selected from the group consisting of N, O, and S, and wherein the nitrogen and sulfur heteroatoms may be optionally oxidized, and the nitrogen atom may be optionally quaternized. The heterocyclic system may be attached, unless otherwise stated, at any heteroatom or carbon atom that affords a stable structure. A heterocycle may be aromatic or non-aromatic in nature. In certain embodiments, the heterocycle is a heteroaryl. As used herein, the term "heteroaryl" or "heteroaromatic" refers to a heterocycle having aromatic character. A polycyclic heteroaryl may include one or more rings that are partially saturated. Examples include tetrahydroquinoline and 2,3-dihydrobenzofuryl.

Examples of non-aromatic heterocycles include monocyclic groups such as aziridine, oxirane, thiirane, azetidine, oxetane, thietane, pyrrolidine, pyrroline, imidazoline, pyrazolidine, dioxolane, sulfolane, 2,3-dihydrofuran, 2,5-dihydrofuran, tetrahydrofuran, thiophane, piperidine, 1,2,3,6-tetrahydropyridine, 1,4-dihydropyridine, piperazine, morpholine, thiomorpholine, pyran, 2,3-dihydropyran, tetrahydropyran, 1,4-dioxane, 1,3-dioxane, homopiperazine, homopiperidine, 1,3-dioxepane, 4,7-dihydro-1,3-dioxepin and hexamethyleneoxide.

Examples of heteroaryl groups include pyridyl, pyrazinyl, pyrimidinyl (such as, but not limited to, 2- and 4-pyrimidinyl), pyridazinyl, thienyl, furyl, pyrrolyl, imidazolyl, thiazolyl, oxazolyl, pyrazolyl, isothiazolyl, 1,2,3-triazolyl, 1,2,4-triazolyl, 1,3,4-triazolyl, tetrazolyl, 1,2,3-thiadiazolyl, 1,2,3-oxadiazolyl, 1,3,4-thiadiazolyl and 1,3,4-oxadiazolyl.

Examples of polycyclic heterocycles include indolyl (such as, but not limited to, 3-, 4-, 5-, 6- and 7-indolyl), indolinyl, quinolyl, tetrahydroquinolyl, isoquinolyl (such as, but not limited to, 1- and 5-isoquinolyl), 1,2,3,4-tetrahydroisoquinolyl, cinnolinyl, quinoxalinyl (such as, but not limited to, 2- and 5-quinoxalinyl), quinazolinyl, phthalazinyl, 1,8-naphthyridinyl, 1,4-benzodioxanyl, coumarin, dihydrocoumarin, 1,5-naphthyridinyl, benzofuryl (such as, but not limited to, 3-, 4-, 5-, 6- and 7-benzofuryl), 2,3-dihydrobenzofuryl, 1,2-benzisoxazolyl, benzothienyl (such as, but not limited to, 3-, 4-, 5-, 6-, and 7-benzothienyl), benzoxazolyl, benzothiazolyl (such as, but not limited to, 2-benzothiazolyl and 5-benzothiazolyl), purinyl, benzimidazolyl, benztriazolyl, thioxanthinyl, carbazolyl, carbolinyl, acridinyl, pyrrolizidinyl, and quinolizidinyl.

The aforementioned listing of heterocyclyl and heteroaryl moieties is intended to be representative and not limiting.

As used herein, the term "substituted" means that an atom or group of atoms has replaced hydrogen as the substituent attached to another group.

For aryl, aryl-($C_1$-$C_3$)alkyl and heterocyclyl groups, the term "substituted" as applied to the rings of these groups refers to any level of substitution, namely mono-, di-, tri-, tetra-, or penta-substitution, where such substitution is permitted. The substituents are independently selected, and substitution may be at any chemically accessible position. In certain embodiments, the substituents vary in number between one and four. In other embodiments, the substituents vary in number between one and three. In yet other embodiments, the substituents vary in number between one and two. In yet other embodiments, the substituents are independently selected from the group consisting of $C_1$-$C_6$ alkyl, —OH, $C_1$-$C_6$ alkoxy, halo, amino, acetamido and nitro. As used herein, where a substituent is an alkyl or alkoxy group, the carbon chain may be branched, straight or cyclic.

Disclosure

The present invention relates in part to the identification of potent, broad-spectrum antiviral compounds. In certain embodiments, the compounds of the invention target high-priority pathogens for which no current treatments are available.

Figures 9A, 9B:
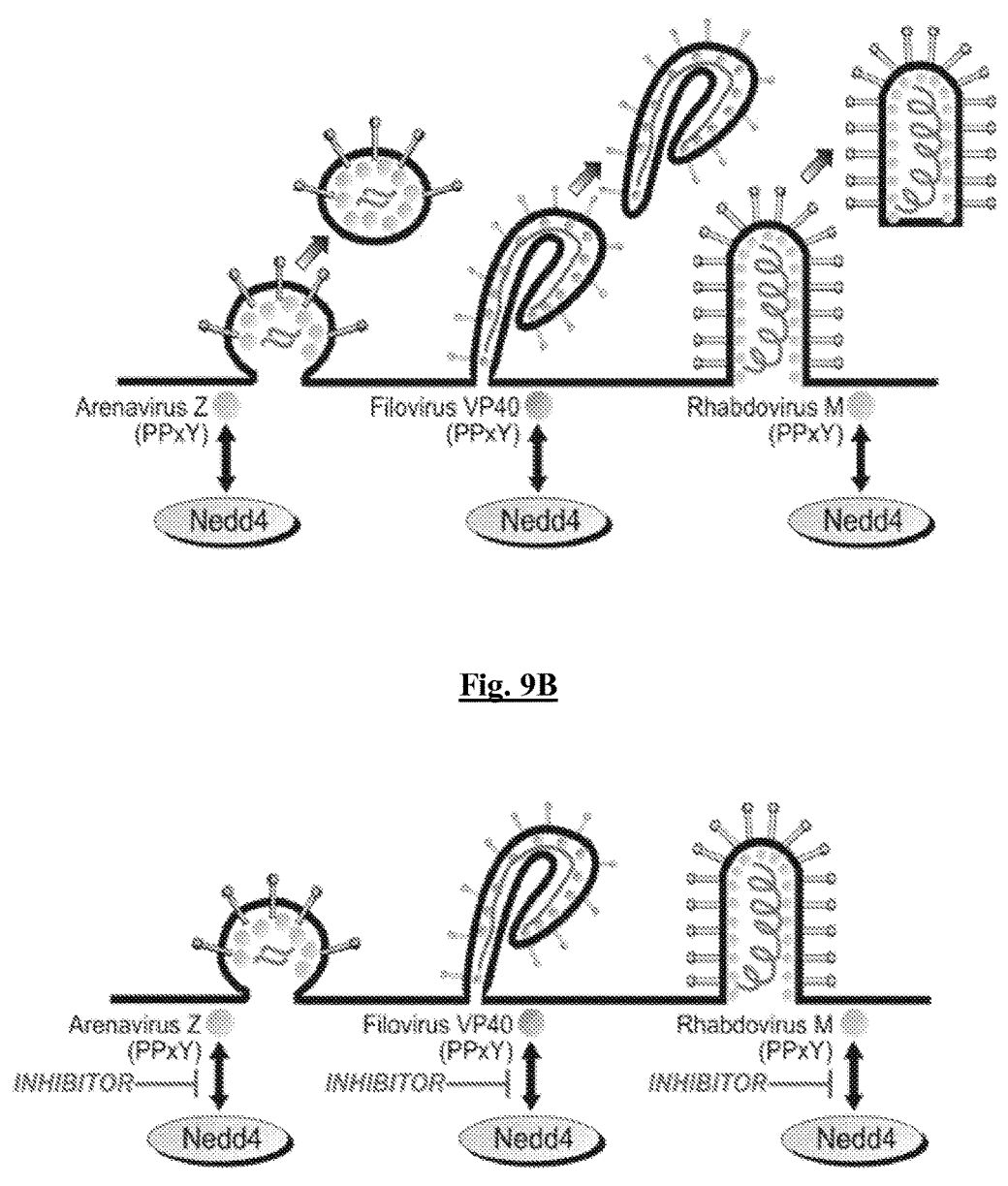

As described herein, an in silico approach combined with functional VLP and live virus budding assays was used to identify small molecules possessing potent antiviral activity. The viral PPxY/host Nedd4 interaction was targeted to identify broad-spectrum inhibitors that diminish the frequency of drug resistance-conferring mutations readily induced by most RNA containing viruses. As demonstrated herein, administration of such an antiviral compound during an outbreak inhibits virus dissemination and spread in infected individuals (FIGS. 9A-9B), thus slowing disease progression and allowing an individual's immune system time to mount a robust response to effectively combat and clear the infection. By inhibiting PPxY-dependent recruitment of host Nedd4, a percentage of mature virions remain tethered to the plasma membrane, unable to bud and spread efficiently to infect new cells (FIGS. 9A-9B).

Figure 7A:
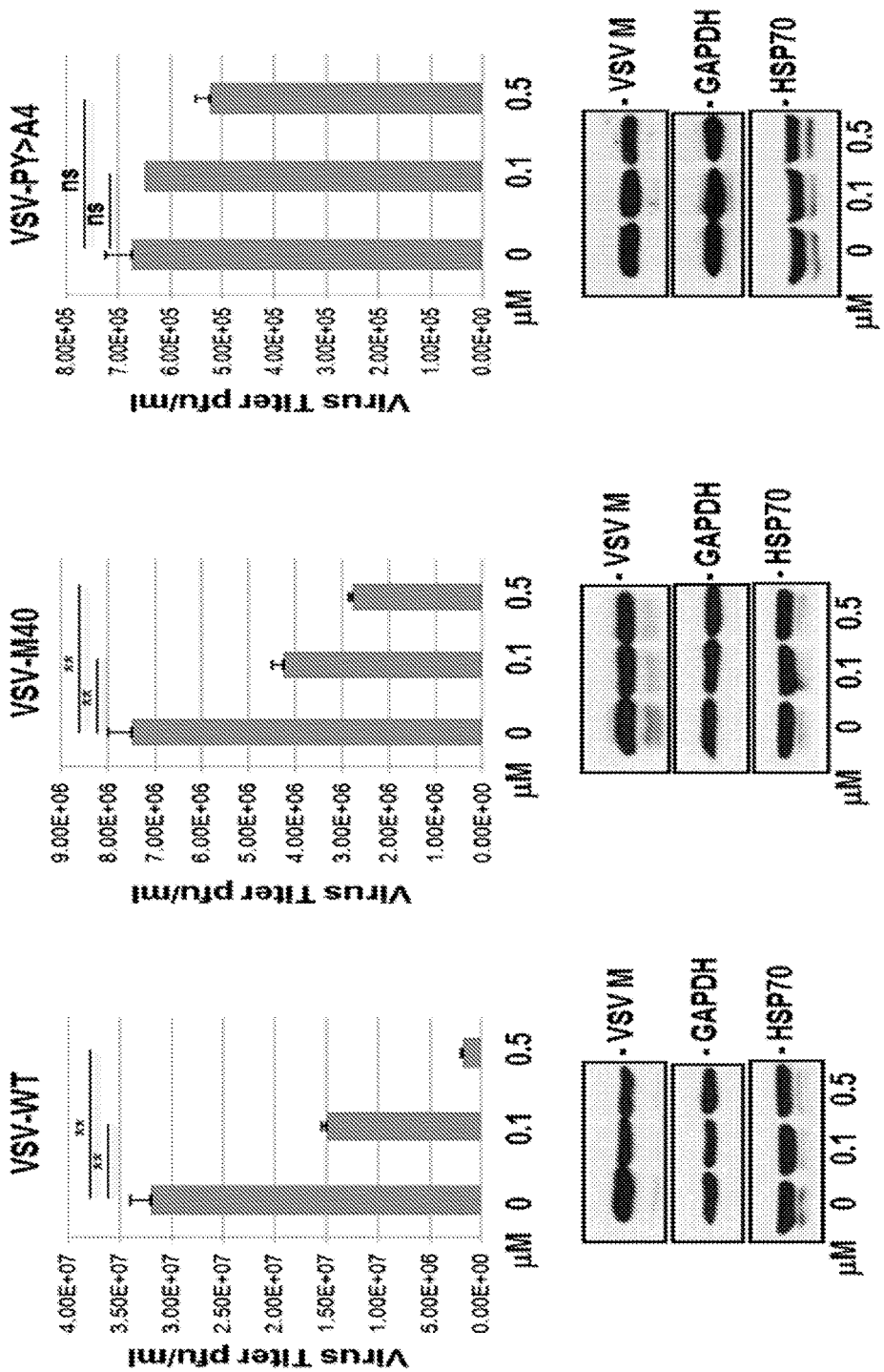
FIGS. 7A-7B illustrate the finding that compounds 4 and 5 inhibit egress of live VSV and VSV recombinants in a PPxY-dependent and dose-dependent manner.

Using iterative rounds of analog selection, potent compounds were identified, such as compounds 4 and 5. Compounds 4 and 5 exhibited broad-spectrum anti-budding activity against filoviruses, arenavirus, and rhabdovirus VLPs and/or virions with virtually no cytotoxicity by MTT assay at the concentrations tested. Without wishing to be limited by any theory, in certain embodiments, 4 and 5 competitively disrupt the viral PPxY/host Nedd4 interaction. Compound 4 significantly inhibited egress of live VSV-WT (a PPxY-dependent virus) by more than 1 log at a concentration of 0.5 μM, yet had no significant effect on egress of VSV-PY>A4 at the same concentration (FIG. 7A). The finding that 4 inhibited budding of VSV-WT to levels comparable to those of VSV-PY>A4 in the absence of drug suggest that 4 specially targets the function of the PPxY motif.

Figure 4A:
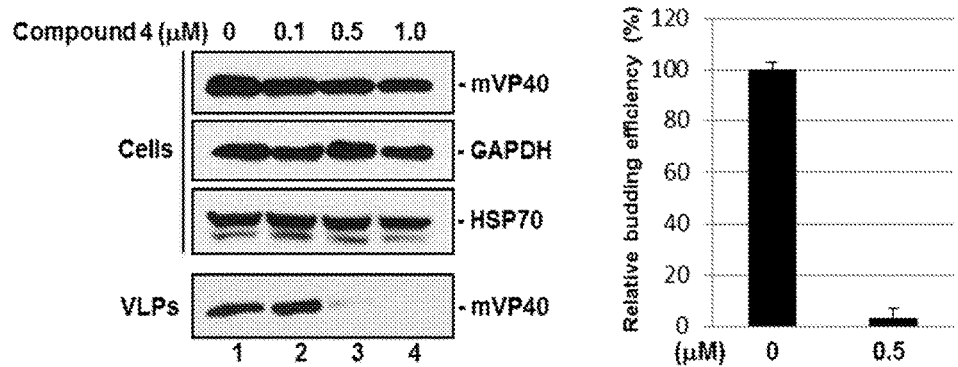
FIGS. 4A-4C illustrate the finding that compound 4 inhibits budding of mVP40 and eVP40 VLPs and blocks mVP40-Nedd4 protein-protein interaction.
Figure 4B:
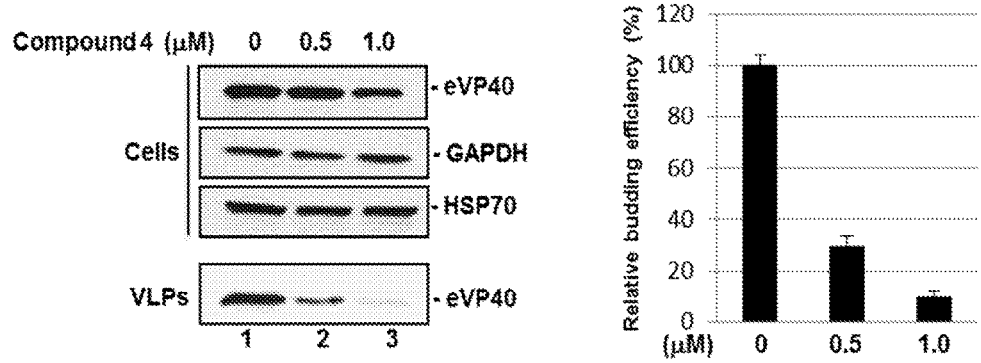
Figure 4C:
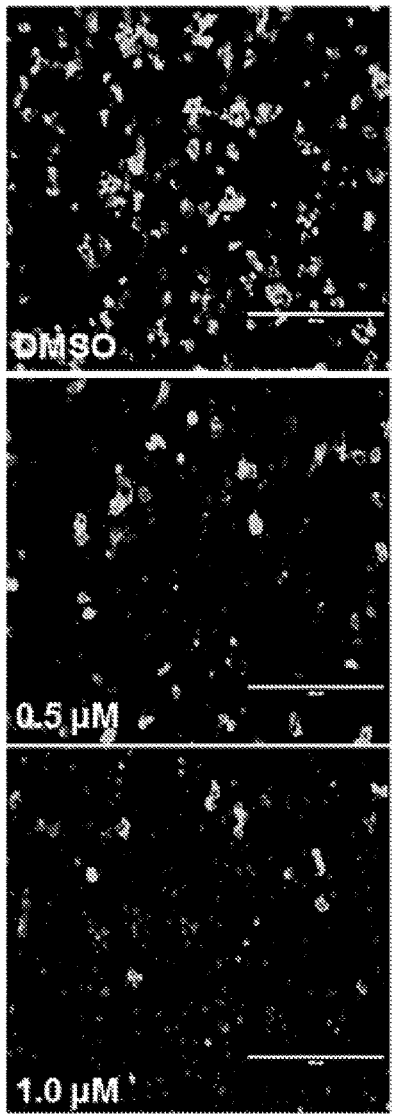
Figure 4C:
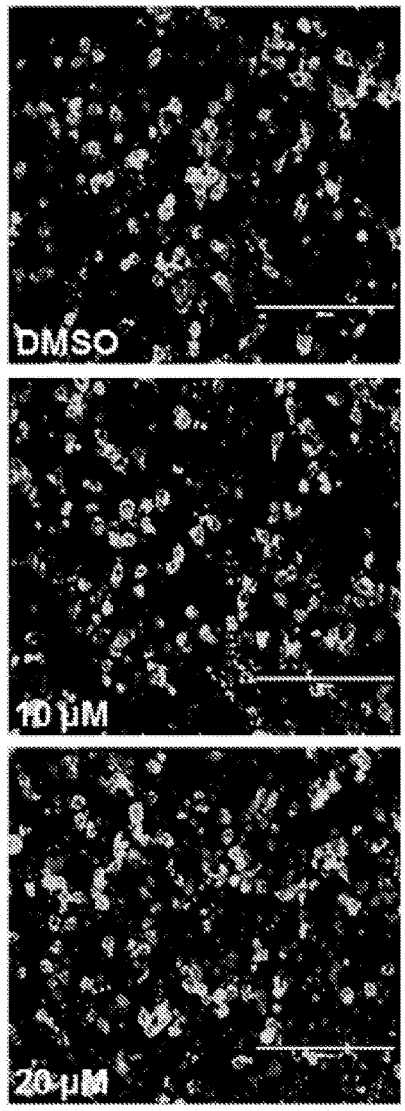
Figure 8B:
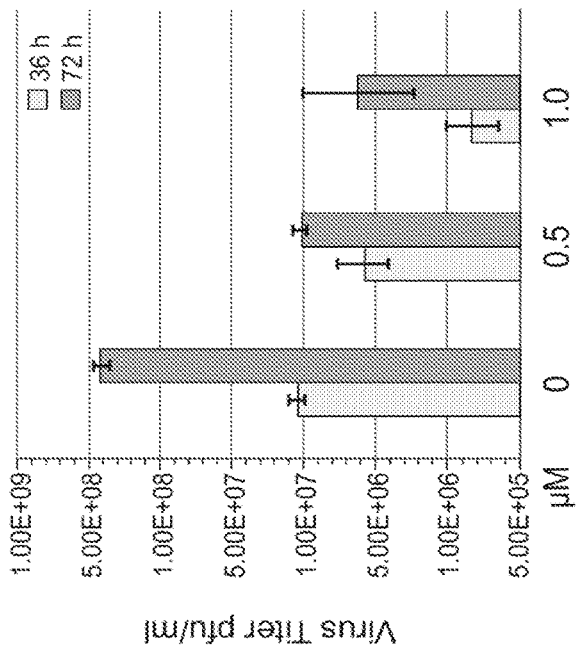
FIGS. 8A-8C illustrate the finding that compounds 4 and 5 inhibit egress of live RABV in cell culture. Bar graphs representing multistep growth of RABV in HEK293T cells in the absence (DMSO alone) or presence of the indicated concentrations of 4 (FIG. 8A) or 5 (FIG. 8B). At the indicated time points, virus-containing supernatant was harvested and titrated in duplicate on BSR cells.
Figure 8A:
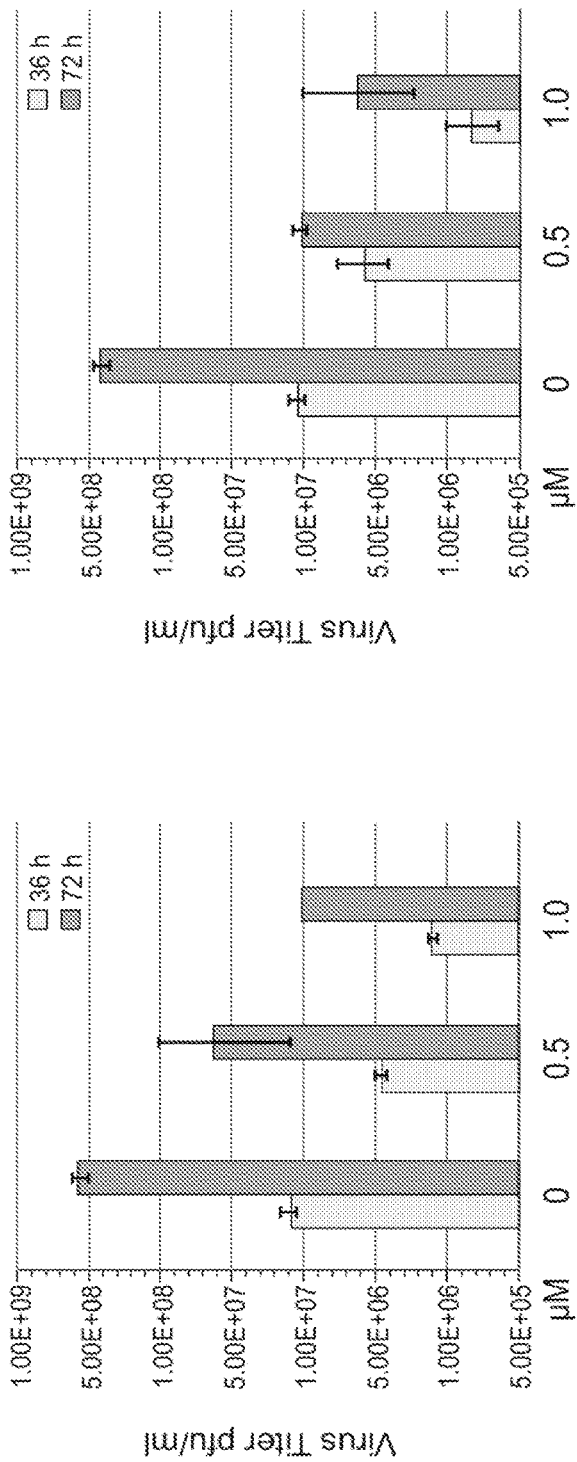
Figure 8C:
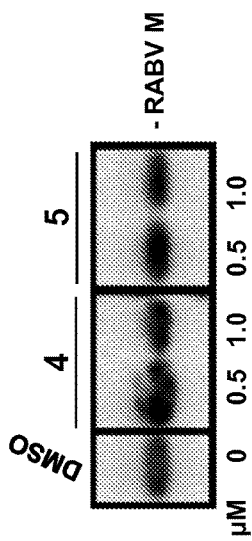

The use of VSV recombinant M40 as a surrogate virus allowed for the assessment of the antiviral activity of 4 and 5 against a BSL-2 virus possessing the PPxY-type L-domain motif originating from a BSL-4 pathogen (EBOV). Compounds 4 and 5 also inhibited egress of live RABV by>1 log at 72 hours post-infection, without any apparent cytotoxicity or inhibitory effect on viral protein synthesis (FIGS. 8A-8C). Interestingly, the replicative cycles and pathogenesis of VSV and RABV are distinct, yet both viruses depend on a PPxY L-domain for efficient egress. BiMC analyses indicated that both 4 and 5, but not 6, can inhibit PPxY-dependent binding of MARV VP40 and Nedd4 in live mammalian cells in a dose-dependent manner (FIGS. 4-5). Indeed, the fraction of positively fluorescing cells, as well as the overall signal intensity, decreased from about 20% in the absence of drug to approximately 3% in the presence of a 1.0 μM concentration of 4 (FIGS. 4A-4C).

The present studies validate the concept of host-oriented therapeutics. As these virus L-domain/host interactions are conserved in a range of emerging RNA viruses, they may represent an Achilles heel in the life cycle of these pathogens. Without wishing to be limited by any theory, RNA viruses may contain one or more L-domains, and a combination of both PTAP and PPxY inhibitors may have a synergistic effect, resulting in enhanced antiviral potency.

Compounds

In one aspect, the invention provides compounds, as well as compositions comprising at least one of the compounds of the present invention.

In another aspect, the invention provides a compound of formula (I), or a salt or solvate thereof:

(I)

[chemical structure of formula (I)]

wherein in (I):

ring a is fused with ring b to form bicyclic core ab, wherein ring a is selected from the group consisting of benzene, pyridine, pyrimidine, pyrazine and triazine, wherein a is optionally substituted with one or more substituents independently selected from the group consisting of $C_1$-$C_4$ alkyl optionally substituted with one or more fluoro atoms, $C_3$-$C_6$ cycloalkyl optionally substituted with one or more fluoro atoms, nitro, cyano, halogen, hydroxy, $C_1$-$C_4$ alkoxy optionally substituted with one or more fluoro atoms, $C_1$-$C_4$ thioalkoxy optionally substituted with one or more fluoro atoms, —$SO_2$($C_1$-$C_4$ alkyl), —C(=O)OR, —NRR, and —C(=O)NRR;

Q is selected from the group consisting of S, S(=O), S(=O)$_2$, O and NR;

Z is selected from the group consisting of —$CH_2$—, —C(=O)—, and —C(R)($R^4$)—C(=O)N ($R^5$)-*, wherein -* is the covalent bond that links Z and $R^1$;

m is 0, 1 or 2;

n is 1, 2, or 3; with the proviso that if m is 0, then n is 2 or 3; each occurrence of R, $R^4$ and $R^5$ is independently H or $C_1$-$C_4$ alkyl; or $R^4$ and $R^5$ are joined as to form an optionally substituted —($CH_2$)$_{1-4}$-alkanediyl group;

$R^1$ is selected from the group consisting of

[chemical structure showing pyrazole with $R^2$, $R^2$, $R^3$ substituents]

—$CH_2CH_2$O-(aryl or substituted aryl), —$CH_2CH_2$O-(hereoaryl or substituted heteroaryl), and —C(=O)—N(R) $CH_2CF_3$;

each occurrence of $R^2$ is independently selected from the group consisting of H, halo, —OR, $C_1$-$C_4$ alkyl optionally substituted with one or more fluoro atoms, $C_3$-$C_6$ cycloalkyl optionally substituted with one or more fluoro atoms, aryl, substituted aryl, heteroaryl, substituted heteroaryl, arylalkyl, substituted arylalkyl, heteroarylalkyl, substituted heteroarylalkyl, heteroalkyl, substituted heteroalkyl, —C(=O)OR, and —C(=O)NRR; and, $R^3$ is selected from the group consisting of H, $C_1$-$C_4$ alkyl optionally substituted with one or more fluoro atoms, $C_3$-$C_6$ cycloalkyl optionally substituted with one or more fluoro atoms, aryl, substituted aryl, heterocycle, substituted heterocycle, arylalkyl, substituted arylalkyl, heteroarylalkyl, substituted heteroarylalkyl, heteroalkyl, substituted heteroalkyl, —$CH_2$C(=O)OR, and —$CH_2$C(=O)NRR. In certain embodiments, the compound of formula (I) is the compound of formula (Ia), or a salt or solvate thereof:

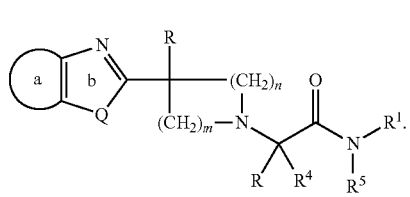

In certain embodiments, the compound of formula (I) is not selected from the group consisting of 2-(3-(benzo[d]thiazol-2-yl)piperidin-1-yl)-N-((2,2,2-trifluoroethyl)carbamoyl) acetamide (1)

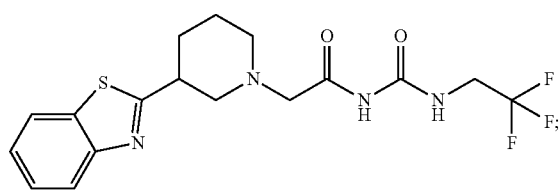 [SMILES: O=C(CN1CCCC(c2nc3ccccc3s2)C1)NC(=O)NCC(F)(F)F]

2-(3-(benzo[d]thiazol-2-yl)piperidin-1-yl)-N-(3,5-dimethyl-1H-pyrazol-4-yl) acetamide (2)

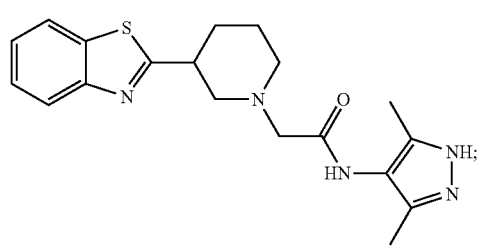 [SMILES: Cc1n[nH]c(C)c1NC(=O)CN1CCCC(c2nc3ccccc3s2)C1]

2-(3-(benzo[d]thiazol-2-yl)piperidin-1-yl)-N-(2-phenoxyethyl)acetamide (2e)

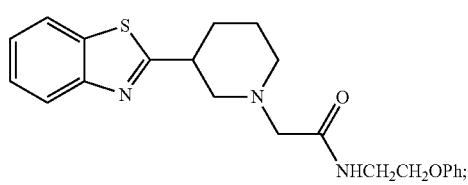

2-(3-(benzo[d]thiazol-2-yl)piperidin-1-yl)-N-(3,5-dimethyl-1-phenyl-1H-pyrazol-4-yl)acetamide (4)

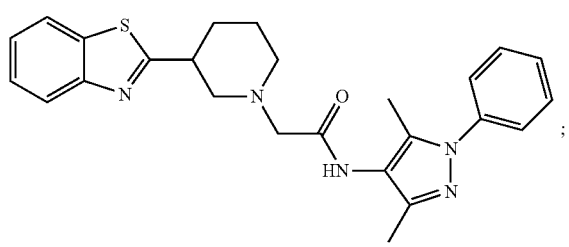 [SMILES: Cc1nn(-c2ccccc2)c(C)c1NC(=O)CN1CCCC(c2nc3ccccc3s2)C1]

3-[4-(1H-benzimidazol-2-yl)-1-piperidinyl]-1-(1-methyl-1H-pyrazol-4-yl)-2-pyrrolidinone

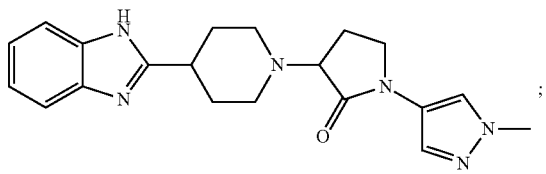 [SMILES: Cn1cc(N2CCC(N3CCC(c4nc5ccccc5[nH]4)CC3)C2=O)cn1]

3-[3-(1H-benzimidazol-2-yl)-1-piperidinyl]-1-(1-methyl-1H-pyrazol-4-yl)-2-pyrrolidinone

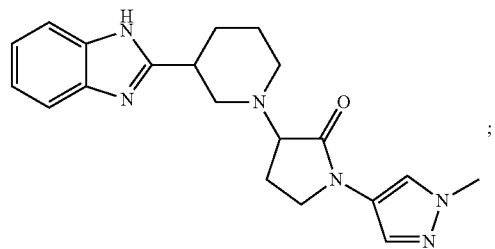 [SMILES: Cn1cc(N2CCC(N3CCCC(c4nc5ccccc5[nH]4)C3)C2=O)cn1]

4-(2-benzoxazolyl)-N-(3,5-dimethyl-1-phenyl-1H-pyrazol-4-yl)-1-piperidineacetamide

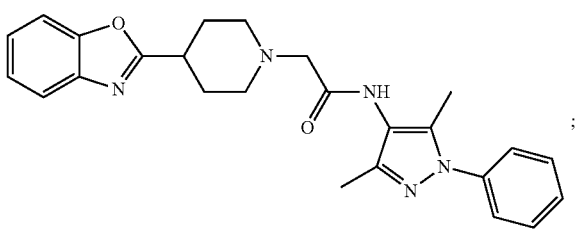 [SMILES: Cc1nn(-c2ccccc2)c(C)c1NC(=O)CN1CCC(c2nc3ccccc3o2)CC1]

4-(5-chloro-2-benzoxazolyl)-N-(1,3,5-trimethyl-1H-pyrazol-4-yl)-1-piperidineacetamide

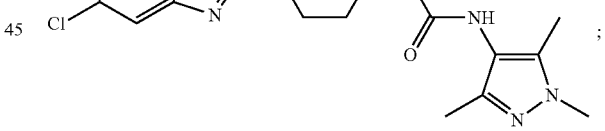

2-(6-fluoro-1H-benzimidazol-2-yl)-N-(1-methyl-1H-pyrazol-4-yl)-1-pyrrolidineacetamide

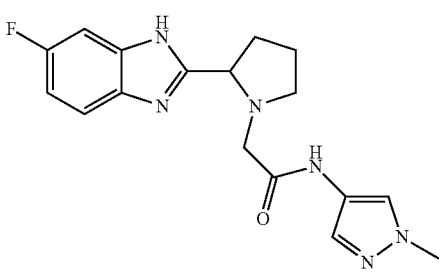

4-(2-benzothiazolyl)-N-[3,5-dimethyl-1-(4-methylphenyl)-1H-pyrazol-4-yl]-1-piperidine acetamide

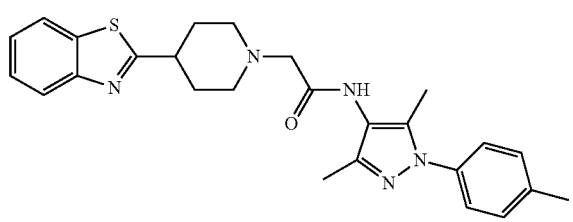

4-(2-benzoxazolyl)-N-(1,3,5-trimethyl-1H-pyrazol-4-yl)-1-piperidineacetamide

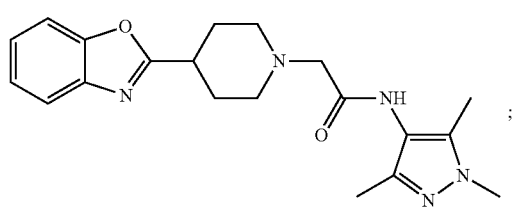 [SMILES: Cc1nn(C)c(C)c1NC(=O)CN1CCC(c2nc3ccccc3o2)CC1]

4-(2-benzoxazolyl)-N-[3,5-dimethyl-1-(4-methylphenyl)-1H-pyrazol-4-yl]-1-piperidine acetamide

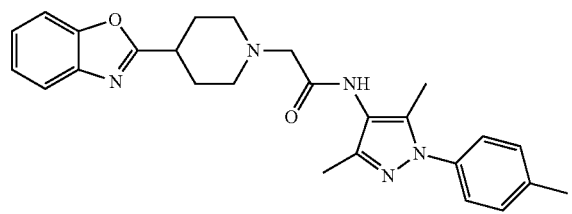

N-(1-ethyl-3,5-dimethyl-1H-pyrazol-4-yl)-4-(7-methyl-1H-benzimidazol-2-yl)-1-piperidine acetamide

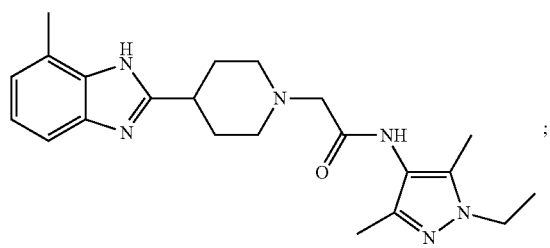 [SMILES: CCn1nc(C)c(NC(=O)CN2CCC(c3nc4cccc(C)c4[nH]3)CC2)c1C]

N-(1-ethyl-3,5-dimethyl-1H-pyrazol-4-yl)-2-(6-methyl-1H-benzimidazol-2-yl)-1-pyrrolidine acetamide

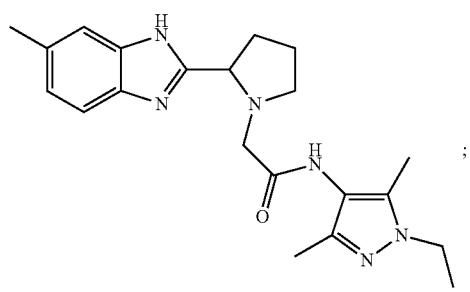 [SMILES: CCn1nc(C)c(NC(=O)CN2CCCC2c2nc3ccc(C)cc3[nH]2)c1C]

4-(5-chloro-2-benzoxazolyl)-α-methyl-N-(1,3,5-trimethyl-1H-pyrazol-4-yl)-1-piperidine acetamide

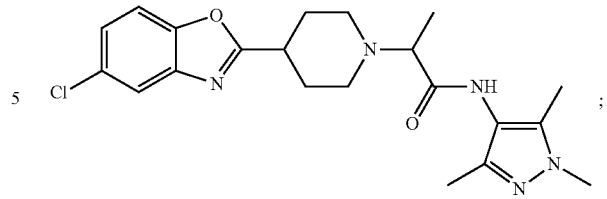

3-(2-benzoxazolyl)-α-methyl-N-(1,3,5-trimethyl-1H-pyrazol-4-yl)-1-piperidineacetamide

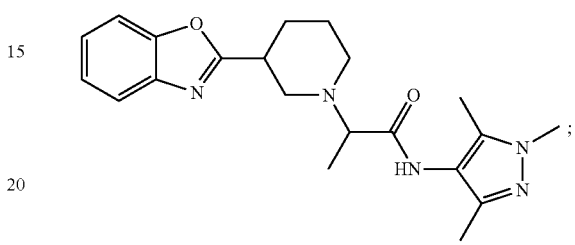

3-[1-(1-methylethyl)-1H-benzimidazol-2-yl]-N-(1-methyl-1H-pyrazol-4-yl)-1-piperidineacetamide

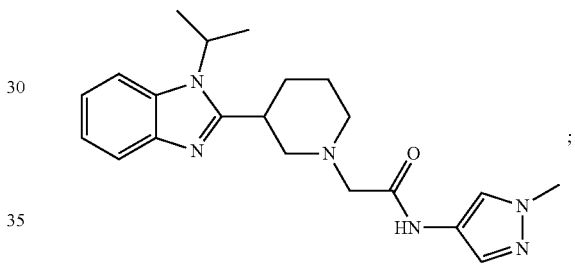

3-(1H-benzimidazol-2-yl)-N-(1-ethyl-3-methyl-1H-pyrazol-4-yl)-1-piperidineacetamide

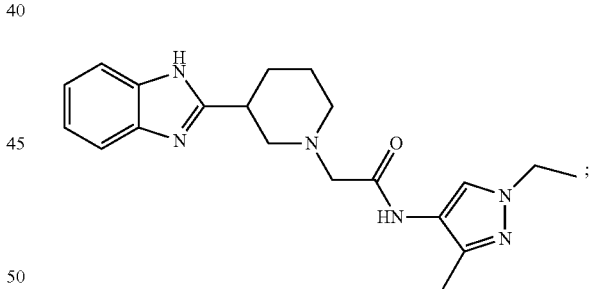

N-(1,5-dimethyl-1H-pyrazol-4-yl)-3-(1-methyl-1H-benzimidazol-2-yl)-1-piperidineacetamide

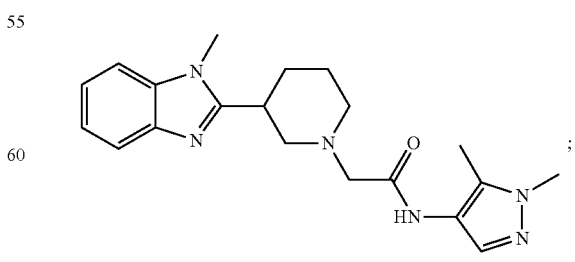

3[1-(1-methylethyl)-1H-benzimidazol-2-yl]-N-(1,3,5-trimethyl-1H-pyrazol-4-yl)-1-piperidineacetamide

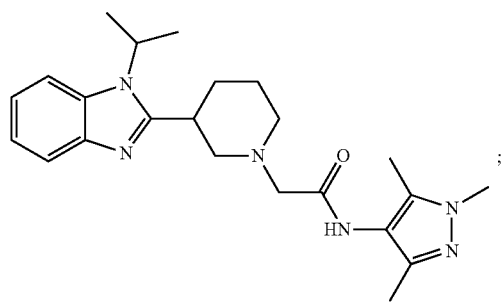 [SMILES: Cc1nn(C)c(C)c1NC(=O)CN1CCCC(c2nc3ccccc3n2C(C)C)C1]

3-(1H-benzimidazol-2-yl)-N-(1-ethyl-3,5-dimethyl-1H-pyrazol-4-yl)-1-piperidineacetamide

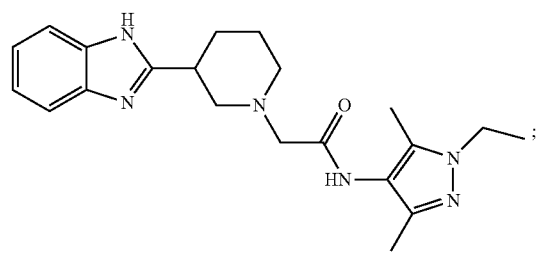 [SMILES: CCn1nc(C)c(NC(=O)CN2CCCC(c3nc4ccccc4[nH]3)C2)c1C]

N-(1-ethyl-3,5-dimethyl-1H-pyrazol-4-yl)-3-(1-methyl-1H-benzimidazol-2-yl)-1-piperidineacetamide

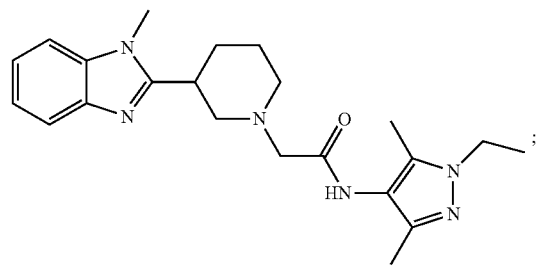 [SMILES: CCn1nc(C)c(NC(=O)CN2CCCC(c3nc4ccccc4n3C)C2)c1C]

N-(1,3-dimethyl-1H-pyrazol-4-yl)-3-[1-(1-methylethyl)-1H-benzimidazol-2-yl]-1-piperidineacetamide

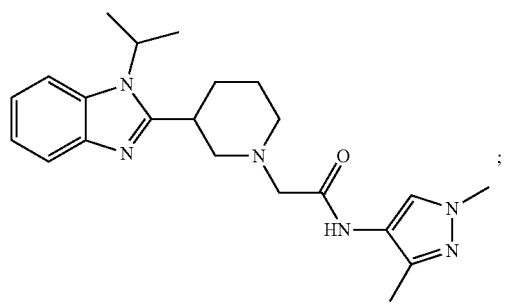 [SMILES: Cc1nn(C)cc1NC(=O)CN1CCCC(c2nc3ccccc3n2C(C)C)C1]

N-(1-ethyl-3-methyl-1H-pyrazol-4-yl)-3-[1-(1-methylethyl)-1H-benzimidazol-2-yl]-1-piperidineacetamide

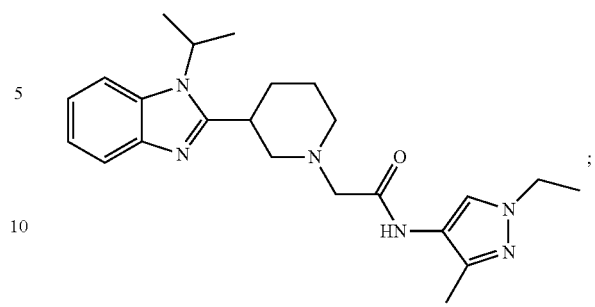

N-(1-ethyl-3-methyl-1H-pyrazol-4-yl)-3-(1-methyl-1H-benzimidazol-2-yl)-1-piperidineacetamide

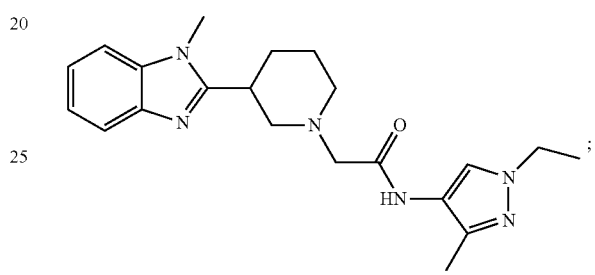

3-(1-methyl-1H-benzimidazol-2-yl)-N-(1-methyl-1H-pyrazol-4-yl)-1-piperidineacetamide

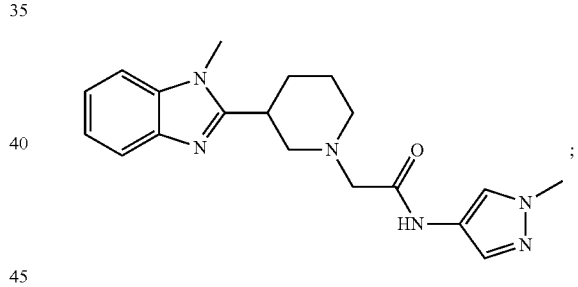

3-(1-methyl-1H-benzimidazol-2-yl)-N-(1,3,5-trimethyl-1H-pyrazol-4-yl)-1-piperidineacetamide

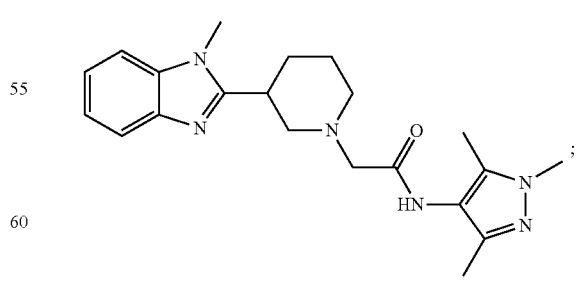

N-(1-ethyl-3,5-dimethyl-1H-pyrazol-4-yl)-3-[1-(1-methylethyl)-1H-benzimidazol-2-yl]-1-piperidineacetamide

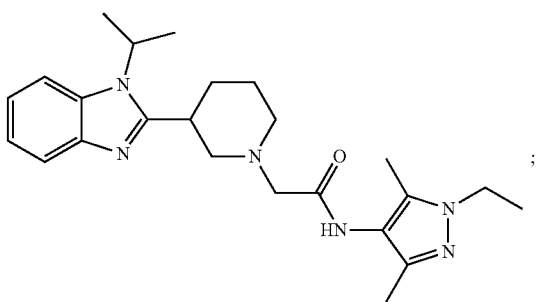 [SMILES: CCn1nc(C)c(NC(=O)CN2CCCC(c3nc4ccccc4n3C(C)C)C2)c1C]

2-(2-benzothiazolyl)-N-(1,3,5-trimethyl-1H-pyrazol-4-yl)-1-pyrrolidineacetamide

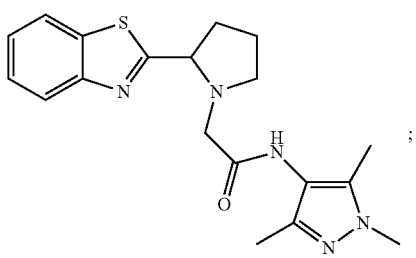 [SMILES: Cc1nn(C)c(C)c1NC(=O)CN1CCCC1c1nc2ccccc2s1]

2-(2-benzothiazolyl)-N-(3,5-dimethyl-1-phenyl-1H-pyrazol-4-yl)-1-pyrrolidineacetamide

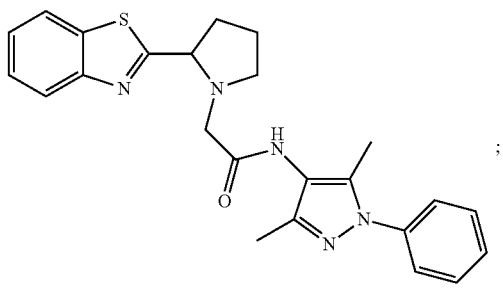 [SMILES: Cc1nn(-c2ccccc2)c(C)c1NC(=O)CN1CCCC1c1nc2ccccc2s1]

2-(4-(benzo[d]thiazol-2-yl)piperazin-1-yl)-N-(3,5-dimethyl-1H-pyrazol-4-yl)acetamide (2g)

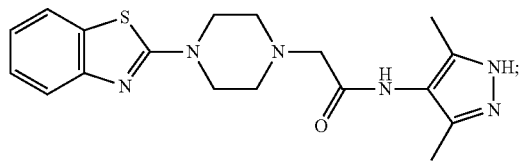 [SMILES: Cc1n[nH]c(C)c1NC(=O)CN1CCN(c2nc3ccccc3s2)CC1]

4-(2-benzothiazolyl)-N-(3,5-dimethyl-1-phenyl-1H-pyrazol-4-yl)-1-piperidineacetamide (2h)

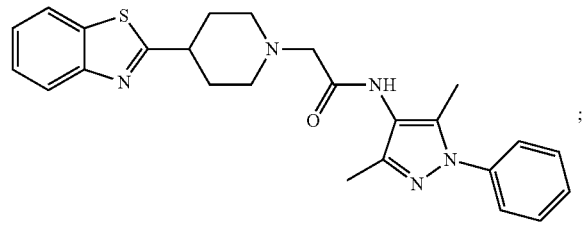 [SMILES: Cc1nn(-c2ccccc2)c(C)c1NC(=O)CN1CCC(c2nc3ccccc3s2)CC1]

and,
(4-(benzo[d]thiazol-2-yl)piperidin-1-yl)(3,5-dimethyl-1-phenyl-1H-pyrazol-4-yl)methanone (2k)

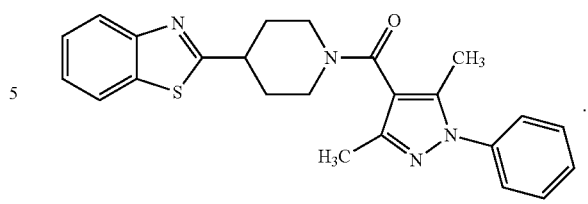

In certain embodiments, the compound of formula (I) is at least one selected from the group consisting of:

2-(3-(benzo[d]thiazol-2-yl)piperidin-1-yl)-N-(3,5-dimethyl-1H-pyrazol-4-yl)acetamide (2);

2-(3-(benzo[d]thiazol-2-yl)piperidin-1-yl)-N-(2-phenoxyethyl)acetamide (2e); and, and, 2-(3-(benzo[d]thiazol-2-yl)piperidin-1-yl)-N-(3,5-dimethyl-1-phenyl-1H-pyrazol-4-yl) acetamide (4).

In certain embodiments, the compound of formula (I) is at least one selected from the group consisting of:

2-(3-(benzo[d]thiazol-2-yl)piperidin-1-yl)-N-(3,5-dimethyl-1H-pyrazol-4-yl)acetamide (2);

2-(3-(benzo[d]thiazol-2-yl)piperidin-1-yl)-N-(2-phenoxyethyl)acetamide (2e);

and, 2-(3-(benzo[d]thiazol-2-yl)piperidin-1-yl)-N-(3,5-dimethyl-1-phenyl-1H-pyrazol-4-yl) acetamide (4);

(4-Benzothiazol-2-yl-piperidin-1-yl)-(3,5-dimethyl-1H-pyrazol-4-yl)-methanone (2i)

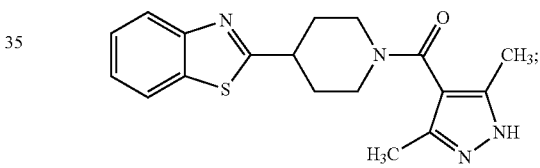

(4-(benzo[d]thiazol-2-yl)piperidin-1-yl)(1,3,5-trimethyl-1H-pyrazol-4-yl)methanone (2j)

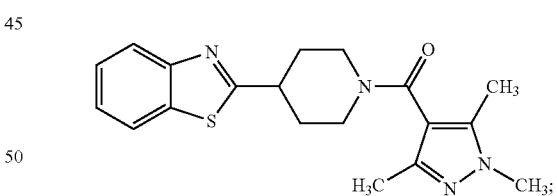

2-[1-(1,3,5-Trimethyl-1H-pyrazol-4-ylmethyl)-piperidin-4-yl]-benzothiazole (2l)

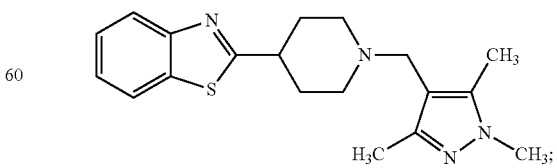

2-[1-(3,5-Dimethyl-1-phenyl-1H-pyrazol-4-ylmethyl)-piperidin-4-yl ]-benzothiazole (2m)

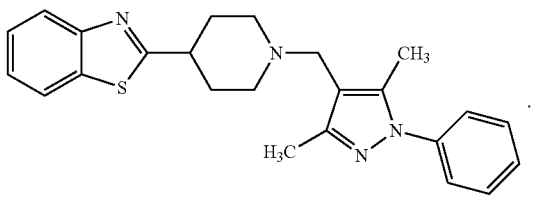 [SMILES: Cc1nn(-c2ccccc2)c(C)c1CN1CCC(c2nc3ccccc3s2)CC1]

In certain embodiments, the compound of formula (I) is at least one selected from the group consisting of: (4-benzothiazol-2-yl-piperidin-1-yl)-(3,5-dimethyl-1H-pyrazol-4-yl)-methanone (2i); (4-(benzo[d]thiazol-2-yl)piperidin-1-yl)(1,3,5-trimethyl-1H-pyrazol-4-yl)methanone (2j); 2-[1-(1,3,5-trimethyl-1H-pyrazol-4-ylmethyl)-piperidin-4-yl]-benzothiazole (2l); and, 2-[1-(3,5-dimethyl-1-phenyl-1H-pyrazol-4-ylmethyl)-piperidin-4-yl]-benzothiazole (2m).

In certain embodiments, the bicyclic core ab is selected from the group consisting of:

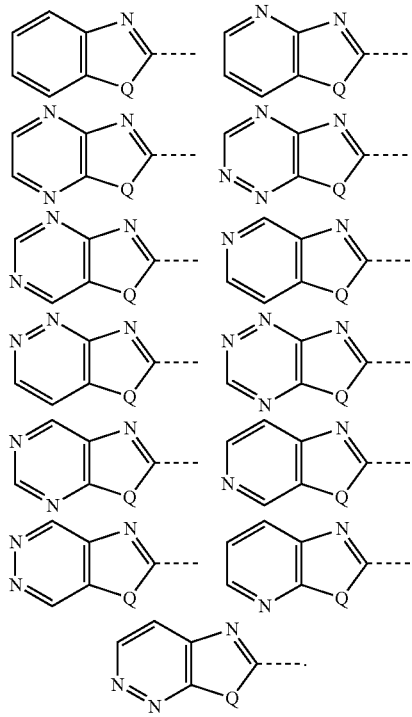

In one aspect, the invention provides a compound of formula (II), or a salt or solvate thereof:

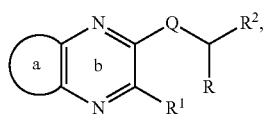

(II)

wherein in (II):

ring a is fused with ring b to form bicyclic core ab, wherein ring a is selected from the group consisting of benzene, pyridine, pyrimidine, pyrazine and triazine, wherein a is optionally substituted with one or more substituents independently selected from the group consisting of $C_1$-$C_4$ alkyl optionally substituted with one or more fluoro atoms, $C_3$-$C_6$ cycloalkyl optionally substituted with one or more fluoro atoms, nitro, cyano, halogen, hydroxy, $C_1$-$C_4$ alkoxy optionally substituted with one or more fluoro atoms, $C_1$-$C_4$ thioalkoxy optionally substituted with one or more fluoro atoms, —SO$_2$($C_1$-$C_4$ alkyl), —C(=O)OR, —NRR, and —C(=O)NRR;

Q is S, S(=O), S(=O)$_2$, O or NR;

each occurrence of R is independently H or $C_1$-$C_4$ alkyl;

$R^1$ is selected from the group consisting of H, $C_1$-$C_4$ alkyl optionally substituted with one or more fluoro atoms, $C_3$-$C_6$ cycloalkyl optionally substituted with one or more fluoro atoms, aryl, substituted aryl, heteroaryl, substituted heteroaryl, arylalkyl, substituted arylalkyl, heteroarylalkyl, substituted heteroarylalkyl, heteroalkyl, substituted heteroalkyl, —C(=O)OR, and —C(=O)NRR;

$R^2$ is selected from the group consisting of —C(=O)N(R)C(=O)NR$^3$R$^4$, —C(=O)N(R)C(=O)OR$^3$ and

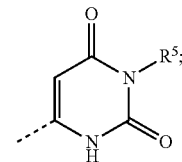

$R^3$ is selected from the group consisting of H, $C_1$-$C_4$ alkyl optionally substituted with one or more fluoro atoms, $C_3$-$C_6$ cycloalkyl optionally substituted with one or more fluoro atoms, aryl, substituted aryl, heteroaryl, substituted heteroaryl, arylalkyl, substituted arylalkyl, heteroarylalkyl, substituted heteroarylalkyl, heteroalkyl, substituted heteroalkyl, —C(=O)OR and —C(=O)NRR;

$R^4$ is H or $C_1$-$C_4$ alkyl, or $R^3$ and $R^4$ are taken together with the N atom to which both groups are bound to form a four- to seven-membered optionally substituted heterocyclic or heteroaromatic ring; and, $R^5$ is selected from the group consisting of H and $C_1$-$C_4$ alkyl optionally substituted with at least one substituent selected from the group consisting of halo, hydroxy, $C_1$-$C_4$ alkoxy, $C_1$-$C_4$ thioalkoxy, —SO$_2$($C_1$-$C_4$ alkyl), —C(=O)OR, —NRR and —C(=O)NRR.

In certain embodiments, the compound of formula (II) is not selected from the group consisting of:

2-((3-methylquinoxalin-2-yl)thio)-N-((2,2,2-trifluoroethyl)carbamoyl) acetamide (3)

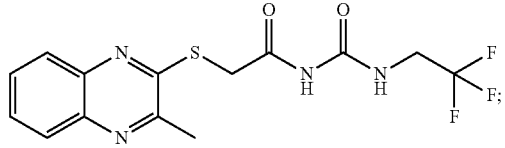 [SMILES: Cc1nc2ccccc2nc1SCC(=O)NC(=O)NCC(F)(F)F]

2-((3-methylquinoxalin-2-yl)thio)-N-(phenylcarbamoyl)acetamide (5)

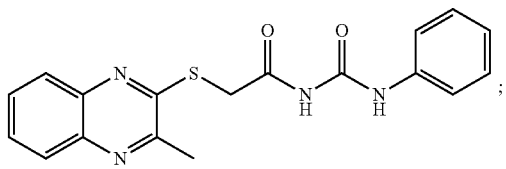 [SMILES: Cc1nc2ccccc2nc1SCC(=O)NC(=O)Nc1ccccc1]

2-((3-methylquinoxalin-2-yl)thio)-N-((thiophen-2-ylmethyl)carbamoyl)acetamide (3i)

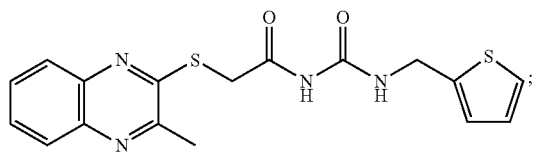 [SMILES: Cc1nc2ccccc2nc1SCC(=O)NC(=O)NCc1cccs1]

N-[(cyclopentylamino)carbonyl]-2-[(3-methyl-2-quinoxalinyl)thio]-acetamide

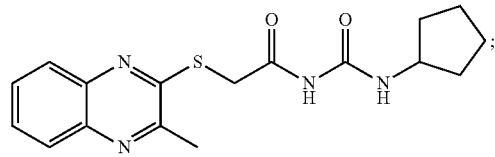 [SMILES: Cc1nc2ccccc2nc1SCC(=O)NC(=O)NC1CCCC1]

N-[(ethylamino)carbonyl]-2-[(3-methyl-2-quinoxalinyl)thio]-propanamide

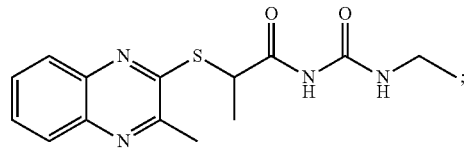 [SMILES: CCNC(=O)NC(=O)C(C)Sc1nc2ccccc2nc1C]

N-[(methylamino)carbonyl]-2-[(3-methyl-2-quinoxalinyl)thio]-propanamide

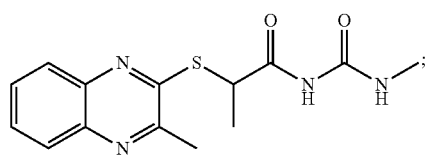 [SMILES: CNC(=O)NC(=O)C(C)Sc1nc2ccccc2nc1C]

N-[aminocarbonyl]-2-[(3-methyl-2-quinoxalinyl)thio]-3-methyl-butanamide

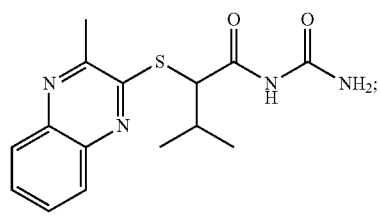 [SMILES: Cc1nc2ccccc2nc1SC(C(=O)NC(N)=O)C(C)C]

N-[(methylamino)carbonyl]-2-(2-quinoxalinyl)thio)-propanamide

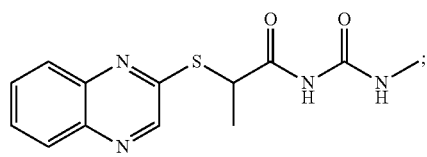 [SMILES: CNC(=O)NC(=O)C(C)Sc1cnc2ccccc2n1]

N-[(ethylamino)carbonyl]-2-(2-quinoxalinyl)thio)-propanamide

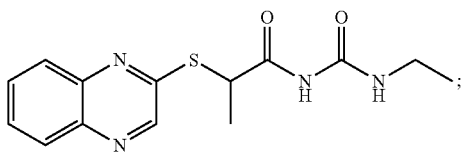 [SMILES: CCNC(=O)NC(=O)C(C)Sc1cnc2ccccc2n1]

N-[[(1-methylethyl)amino]carbonyl]-2-(2-quinoxalinylthio)-propanamide

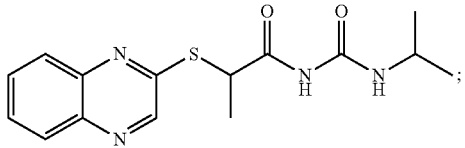 [SMILES: CC(C)NC(=O)NC(=O)C(C)Sc1cnc2ccccc2n1]

N-[[(phenylmethyl)amino]carbonyl]-2-(2-quinoxalinyloxy)-acetamide

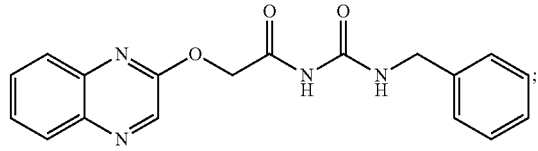 [SMILES: O=C(COc1cnc2ccccc2n1)NC(=O)NCc1ccccc1]

N-[[(1-methylethyl)amino]carbonyl]-2-(2-quinoxalinyloxy)-acetamide

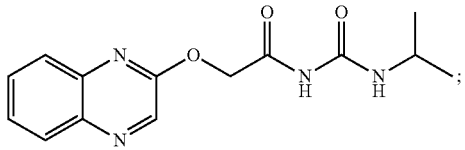 [SMILES: CC(C)NC(=O)NC(=O)COc1cnc2ccccc2n1]

ethyl (2-((3-methylquinoxalin-2-yl)thio)acetyl)carbamate (3y)

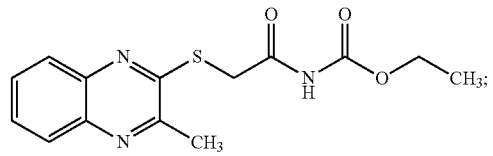 [SMILES: CCOC(=O)NC(=O)CSc1nc2ccccc2nc1C]

and
ethyl 2-((3-methylquinoxalin-2-yl)thio)acetate (3z)

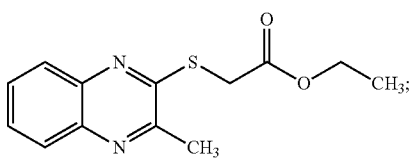 [SMILES: CCOC(=O)CSc1nc2ccccc2nc1C]

In certain embodiments, the compound of formula (II) is at least one selected from the group consisting of:
2-((3-methylquinoxalin-2-yl)thio)-N-((2,2,2-trifluoroethyl)carbamoyl) acetamide (3);

2-((3-methylquinoxalin-2-yl)thio)-N-(phenylcarbamoyl)acetamide (5); and,
2-((3-methylquinoxalin-2-yl)thio)-N-((thiophen-2-ylmethyl)carbamoyl)acetamide (3i).

In certain embodiments, the compound of formula (II) is at least one selected from the group consisting of:
2-((3-methylquinoxalin-2-yl)thio)-N-((2,2,2-trifluoroethyl)carbamoyl)acetamide (3);
N-(ethylcarbamoyl)-2-((3-methylquinoxalin-2-yl)thio)acetamide (3f)

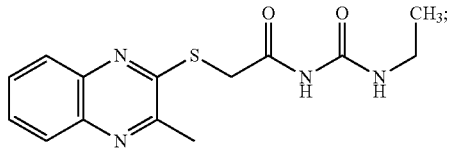 [SMILES: CCNC(=O)NC(=O)CSc1nc2ccccc2nc1C]

N-(cyclopropylcarbamoyl)-2-((3-methylquinoxalin-2-yl)thio)acetamide (3g)

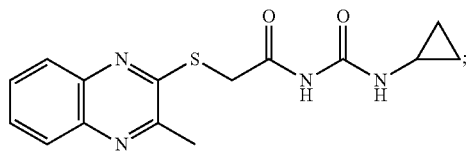 [SMILES: Cc1nc2ccccc2nc1SCC(=O)NC(=O)NC1CC1]

2-((3-methylquinoxalin-2-yl)thio)-N-(phenylcarbamoyl)acetamide (5);
2-((3-methylquinoxalin-2-yl)thio)-N-((thiophen-2-ylmethyl)carbamoyl)acetamide (3i);
6-(3′-Methyl-quinoxalin-2-ylsulfanylmethyl)-1H-pyrimidine-2,4-dione (3n)

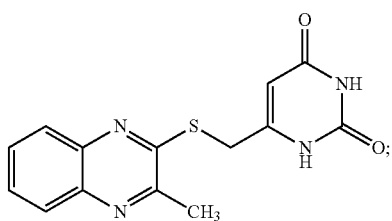 [SMILES: Cc1nc2ccccc2nc1SCc1cc(=O)[nH]c(=O)[nH]1]

N-(benzylcarbamoyl)-2-((3-methylquinoxalin-2-yl)thio)acetamide (3o)

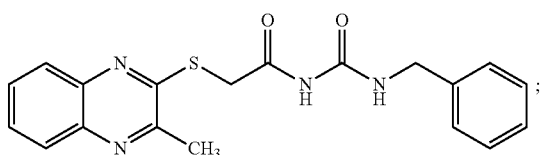

2-((3-methylquinoxalin-2-yl)thio)-N-(pyridin-2-ylcarbamoyl)acetamide (3p)

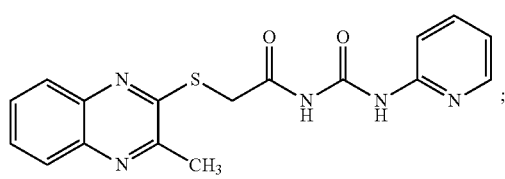

2-((3-methylquinoxalin-2-yl)thio)-N-(pyridin-3-ylcarbamoyl)acetamide (3q)

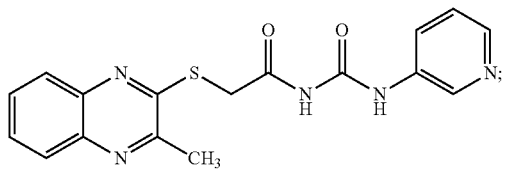 [SMILES: Cc1nc2ccccc2nc1SCC(=O)NC(=O)Nc1cccnc1]

N-((1H-pyrazol-3-yl)carbamoyl)-2-((3-methylquinoxalin-2-yl)thio)acetamide (3r)

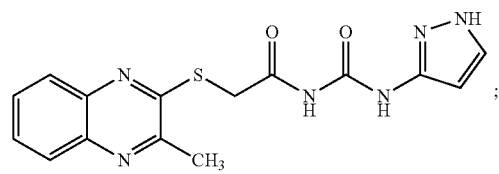 [SMILES: Cc1nc2ccccc2nc1SCC(=O)NC(=O)Nc1cc[nH]n1]

N-((3,5-dimethyl-1H-pyrazol-4-yl)carbamoyl)-2-((3-methylquinoxalin-2-yl)thio)acetamide (3s)

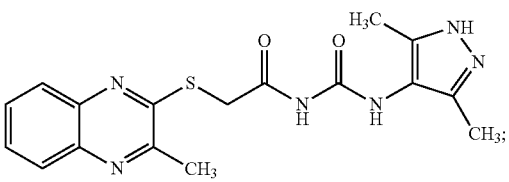

2-((3-methylquinoxalin-2-yl)thio)-N-((1,3,5-trimethyl-1H-pyrazol-4-yl)carbamoyl)acetamide (3t)

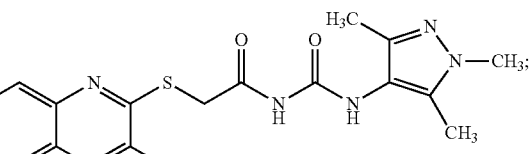

N-((2-fluorophenyl)carbamoyl)-2-((3-methylquinoxalin-2-yl)thio)acetamide (3u)

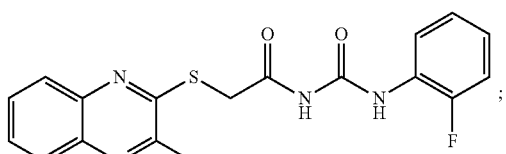

N-((3-fluorophenyl)carbamoyl)-2-((3-methylquinoxalin-2-yl)thio)acetamide (3v)

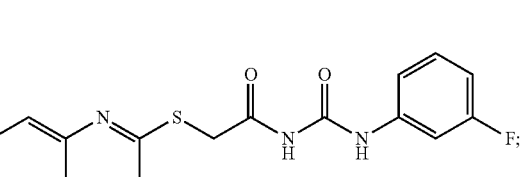

N-((4-fluorophenyl)carbamoyl)-2-((3-methylquinoxalin-2-yl)thio)acetamide (3w)

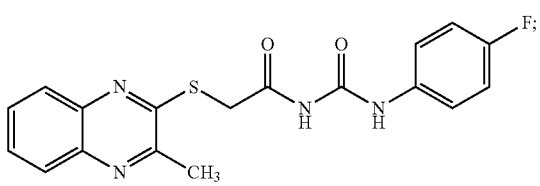 [SMILES: Cc1nc2ccccc2nc1SCC(=O)NC(=O)Nc1ccc(F)cc1]

1-[2-(3-Methyl-quinoxalin-2-yloxy)-acetyl]-3-phenyl-urea (3x)

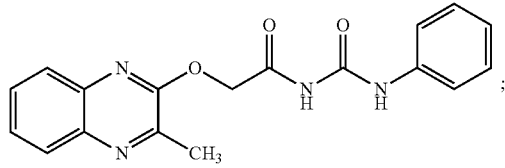 [SMILES: Cc1nc2ccccc2nc1OCC(=O)NC(=O)Nc1ccccc1]

1-Methyl-3-[2-(3-methyl-quinoxalin-2-ylsulfanyl)-acetyl]-1-phenyl-urea (3aa)

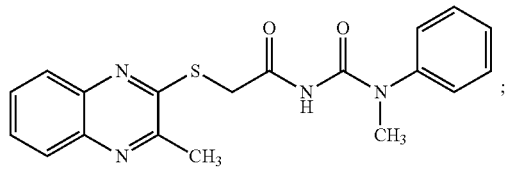 [SMILES: Cc1nc2ccccc2nc1SCC(=O)NC(=O)N(C)c1ccccc1]

1-[2-(3-Benzyl-quinoxalin-2-ylsulfanyl)-acetyl]-3-(3,5-dimethyl-1H-pyrazol-4-yl)-urea (3ab)

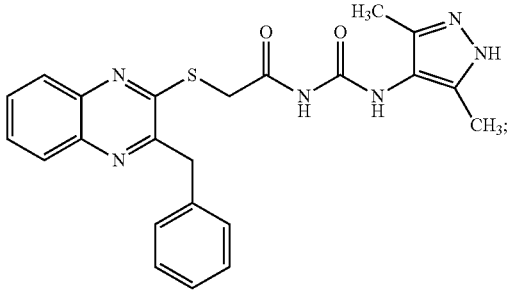 [SMILES: Cc1n[nH]c(C)c1NC(=O)NC(=O)CSc1nc2ccccc2nc1Cc1ccccc1]

2-((3-benzylquinoxalin-2-yl)thio)-N-((1,3,5-trimethyl-1H-pyrazol-4-yl)carbamoyl)acetamide (3ac)

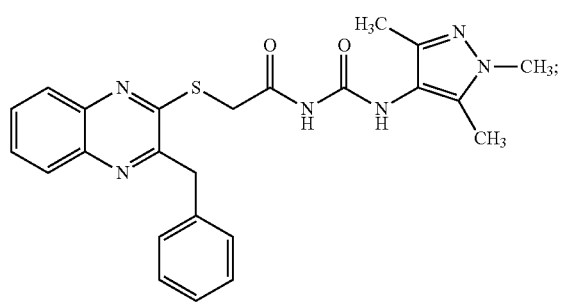 [SMILES: Cc1nn(C)c(C)c1NC(=O)NC(=O)CSc1nc2ccccc2nc1Cc1ccccc1]

and,
2-((3-benzylquinoxalin-2-yl)thio)-N-((4-fluorophenyl)carbamoyl)acetamide (3ad)

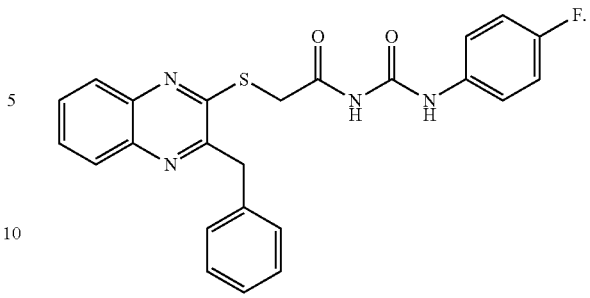

In certain embodiments, the compound of formula (II) is at least one selected from the group consisting of: N-(ethylcarbamoyl)-2-((3-methylquinoxalin-2-yl)thio) acetamide (3f); N-(cyclopropylcarbamoyl)-2-((3-methylquinoxalin-2-yl)thio)acetamide (3g); 6-(3-Methyl-quinoxalin-2-ylsulfanylmethyl)-1H-pyrimidine-2,4-dione (3n); N-(benzyl carbamoyl)-2-((3-methylquinoxalin-2-yl)thio)acetamide (3o); 2-((3-methylquinoxalin-2-yl) thio)-N-(pyridin-2-ylcarbamoyl)acetamide (3p); 2-((3-methylquinoxalin-2-yl)thio)-N-(pyridin-3-ylcarbamoyl)acetamide (3q); N-((1H-pyrazol-3-yl)carbamoyl)-2-((3-methyl quinoxalin-2-yl)thio)acetamide (3r); N-((3,5-dimethyl-1H-pyrazol-4-yl)carbamoyl)-2-((3-methylquinoxalin-2-yl)thio)acetamide (3s); 2-((3-methylquinoxalin-2-yl)thio)-N-((1,3,5-trimethyl-1H-pyrazol-4-yl)carbamoyl)acetamide (3t); N-((2-fluorophenyl) carbamoyl)-2-((3-methylquinoxalin-2-yl)thio)acetamide (3u); N-((3-fluorophenyl)carbamoyl)-2-((3-methyl quinoxalin-2-yl)thio)acetamide (3v); N-((4-fluorophenyl)carbamoyl)-2-((3-methylquinoxalin-2-yl)thio)acetamide (3w); 1-12-(3-Methyl-quinoxalin-2-yloxy)-acetyl]-3-phenyl-urea (3x); 1-Methyl-3-[2-(3-methyl-quinoxalin-2-ylsulfanyl)-acetyl]-1-phenyl-urea (3aa); 1-[2-(3-Benzyl-quinoxalin-2-ylsulfanyl)-acetyl]-3-(3,5-dimethyl-1H-pyrazol-4-yl)-urea (3ab); 2-((3-benzylquinoxalin-2-yl)thio)-N-((1,3,5-trimethyl-1H-pyrazol-4-yl)carbamoyl)acetamide (3ac); 2-((3-benzylquinoxalin-2-yl)thio)-N-((4-fluorophenyl)carbamoyl)acetamide (3ad).

In certain embodiments, the bicyclic core ab is selected from the group consisting of

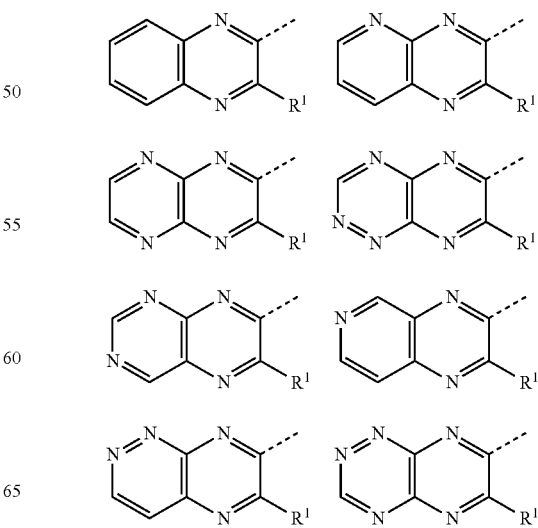

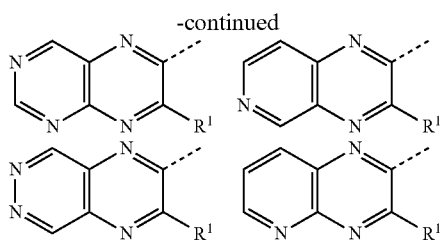
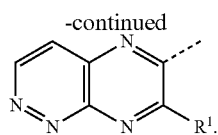
In certain embodiments, the compounds of formula (I) may be prepared according to the following procedure:
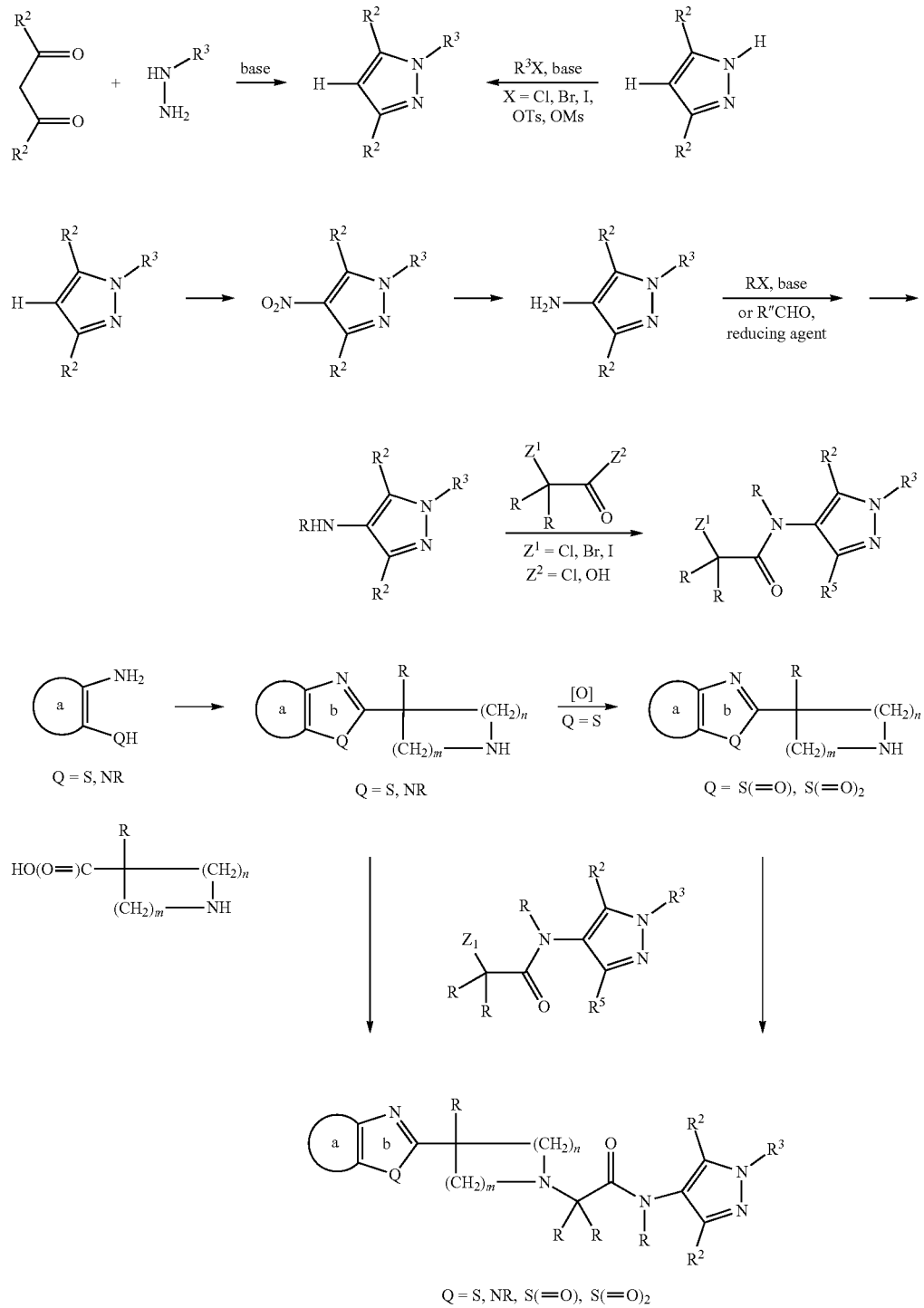

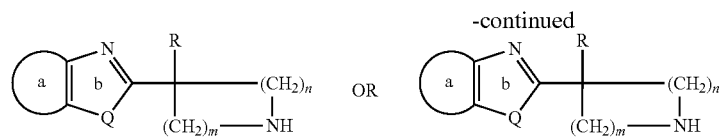
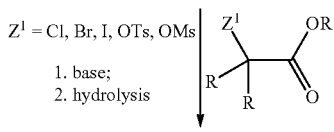
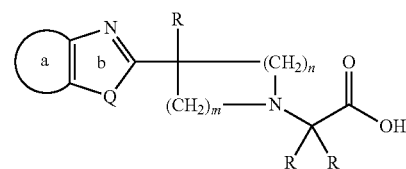
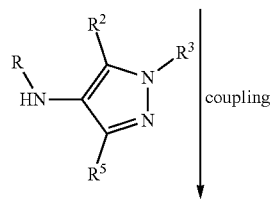
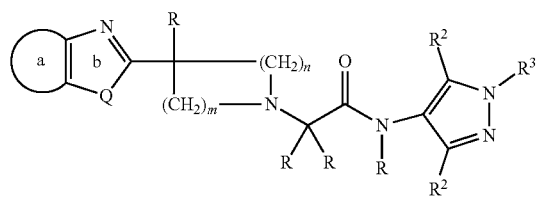
In certain embodiments, the compounds of formula (II) may be prepared according to the following procedure:
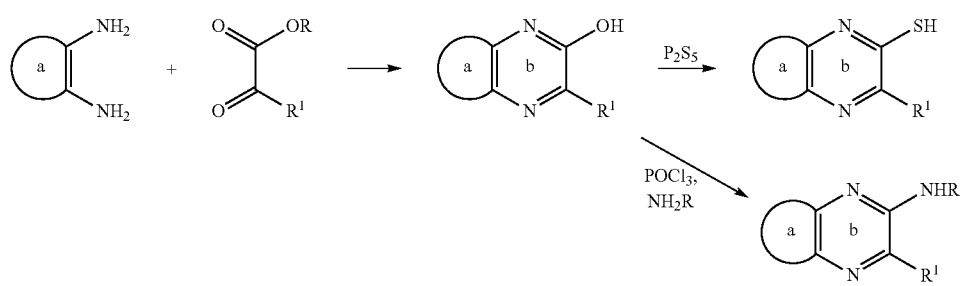
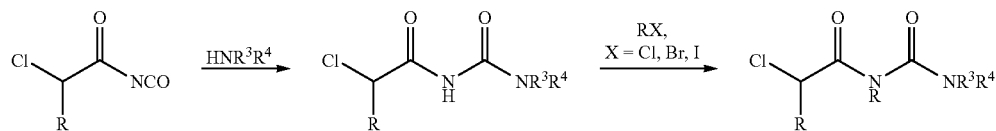

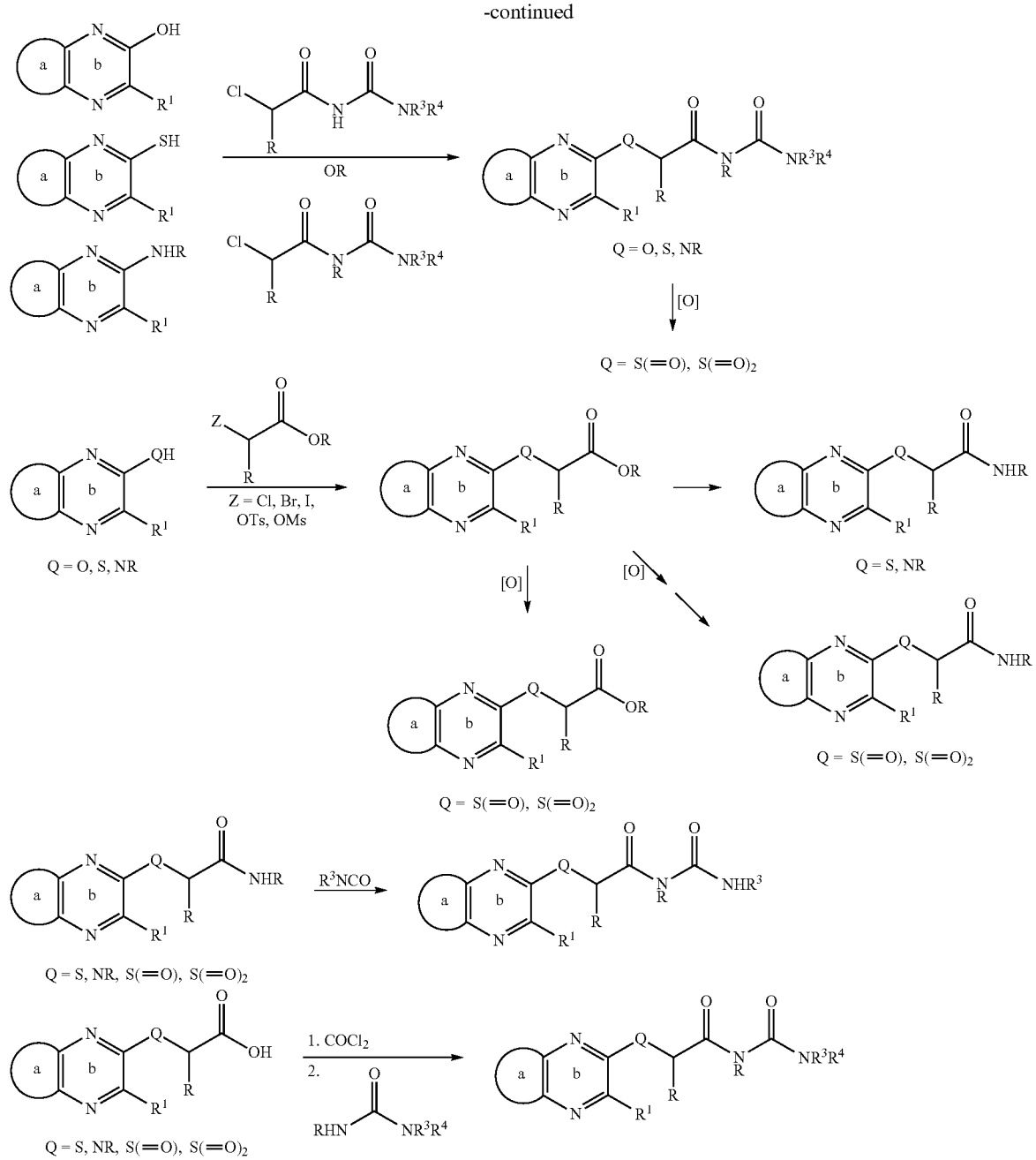

The compounds of the invention may possess one or more stereocenters, and each stereocenter may exist independently in either the (R) or (S) configuration. In certain embodiments, compounds described herein are present in optically active or racemic forms. The compounds described herein encompass racemic, optically-active, regioisomeric and stereoisomeric forms, or combinations thereof that possess the therapeutically useful properties described herein. Preparation of optically active forms is achieved in any suitable manner, including by way of non-limiting example, by resolution of the racemic form with recrystallization techniques, synthesis from optically-active starting materials, chiral synthesis, or chromatographic separation using a chiral stationary phase. In certain embodiments, a mixture of one or more isomer is utilized as the therapeutic compound described herein. In other embodiments, compounds described herein contain one or more chiral centers. These compounds are prepared by any means, including stereoselective synthesis, enantioselective synthesis and/or separation of a mixture of enantiomers and/ or diastereomers. Resolution of compounds and isomers thereof is achieved by any means including, by way of non-limiting example, chemical processes, enzymatic processes, fractional crystallization, distillation, and chromatography.

The methods and formulations described herein include the use of N-oxides (if appropriate), crystalline forms (also known as polymorphs), solvates, amorphous phases, and/or pharmaceutically acceptable salts of compounds having the structure of any compound of the invention, as well as metabolites and active metabolites of these compounds having the same type of activity. Solvates include water, ether (e.g., tetrahydrofuran, methyl tert-butyl ether) or alcohol (e.g., ethanol) solvates, acetates and the like. In certain embodiments, the compounds described herein exist in solvated forms with pharmaceutically acceptable solvents such as water, and ethanol. In other embodiments, the compounds described herein exist in unsolvated form.

In certain embodiments, the compounds of the invention may exist as tautomers. All tautomers are included within the scope of the compounds recited herein.

In certain embodiments, compounds described herein are prepared as prodrugs. A "prodrug" is an agent converted into the parent drug in vivo. In certain embodiments, upon in vivo administration, a prodrug is chemically converted to the biologically, pharmaceutically or therapeutically active form of the compound. In other embodiments, a prodrug is enzymatically metabolized by one or more steps or processes to the biologically, pharmaceutically or therapeutically active form of the compound. In certain embodiments, sites on, for example, the aromatic ring portion of compounds of the invention are susceptible to various metabolic reactions. Incorporation of appropriate substituents on the aromatic ring structures may reduce, minimize or eliminate this metabolic pathway. In certain embodiments, the appropriate substituent to decrease or eliminate the susceptibility of the aromatic ring to metabolic reactions is, by way of example only, a deuterium, a halogen, or an alkyl group.

Compounds described herein also include isotopically-labeled compounds wherein one or more atoms is replaced by an atom having the same atomic number, but an atomic mass or mass number different from the atomic mass or mass number usually found in nature. Examples of isotopes suitable for inclusion in the compounds described herein include and are not limited to $^2$H, $^3$H, $^{11}$C, $^{13}$C, $^{14}$C, $^{36}$Cl, $^{18}$F, $^{123}$I, $^{125}$I, $^{13}$N, $^{15}$N, $^{15}$O, $^{17}$O, $^{18}$O, $^{32}$P, and $^{35}$S. In certain embodiments, isotopically-labeled compounds are useful in drug and/or substrate tissue distribution studies. In other embodiments, substitution with heavier isotopes such as deuterium affords greater metabolic stability (for example, increased in vivo half-life or reduced dosage requirements). In yet other embodiments, substitution with positron emitting isotopes, such as $^{11}$C, $^{18}$F, $^{15}$O and $^{13}$N, is useful in Positron Emission Topography (PET) studies for examining substrate receptor occupancy. Isotopically-labeled compounds are prepared by any suitable method or by processes using an appropriate isotopically-labeled reagent in place of the non-labeled reagent otherwise employed.

In certain embodiments, the compounds described herein are labeled by other means, including, but not limited to, the use of chromophores or fluorescent moieties, bioluminescent labels, or chemiluminescent labels.

The invention further includes a pharmaceutical composition comprising the compound of the invention and a pharmaceutically acceptable carrier.

In certain embodiments, the pharmaceutical composition further comprises at least one additional agent that is useful to treat the diseases or disorders contemplated herein. In certain embodiments, the compound of the invention and the additional agent are co-formulated in the composition.

Salts

The compounds described herein may form salts with acids or bases, and such salts are included in the present invention. In certain embodiments, the salts are pharmaceutically acceptable salts. The term "salts" embraces addition salts of free acids or bases that are useful within the methods of the invention. The term "pharmaceutically acceptable salt" refers to salts that possess toxicity profiles within a range that affords utility in pharmaceutical applications. Pharmaceutically unacceptable salts may nonetheless possess properties such as high crystallinity, which have utility in the practice of the present invention, such as for example utility in process of synthesis, purification or formulation of compounds useful within the methods of the invention.

Suitable pharmaceutically acceptable acid addition salts may be prepared from an inorganic acid or from an organic acid. Examples of inorganic acids include hydrochloric, hydrobromic, hydriodic, nitric, carbonic, sulfuric (including sulfate and hydrogen sulfate), and phosphoric acids (including hydrogen phosphate and dihydrogen phosphate). Appropriate organic acids may be selected from aliphatic, cycloaliphatic, aromatic, aralyphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, malonic, saccharin, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid.

Suitable pharmaceutically acceptable base addition salts of compounds of the invention include, for example, metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N'-dibenzylethylene-diamine, chloroprocaine, choline, diethanolamine, ethylenediamine, meglumine (N-methylglucamine) and procaine. All of these salts may be prepared from the corresponding compound by reacting, for example, the appropriate acid or base with the compound.

Combination Therapies

In certain embodiments, the compounds of the invention are useful in the methods of the invention in combination with at least one additional compound useful for treating or preventing a disease or disorder contemplated within the invention. This additional compound may comprise compounds identified herein or compounds, e.g., commercially available compounds, known to treat, prevent or reduce the symptoms of a viral infection.

In certain embodiments, the at least one additional compound is an antiviral agent. Non-limiting examples of antiviral agents include, but are not limited to, compound 0013 (2-((1,1-dioxidobenzo[d]isothiazol-3-yl)amino)phenyl 2-chlorobenzoate, or a salt or solvate thereof), as recited in Lu et al., 2014, J. Virol. doi: 10.1128/JVI.03757-13:

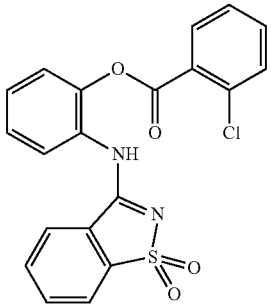 [SMILES: O=C(Oc1ccccc1NC1=NS(=O)(=O)c2ccccc21)c1ccccc1Cl]

A synergistic effect may be calculated, for example, using suitable methods such as, for example, the Sigmoid-$E_{max}$ equation (Holford & Scheiner, 19981, Clin. Pharmacokinet.

6: 429-453), the equation of Loewe additivity (Loewe & Muischnek, 1926,Arch. Exp. Pathol Pharmacol. 114: 313-326) and the median-effect equation (Chou & Talalay, 1984, Adv. Enzyme Regul. 22:27-55). Each equation referred to above may be applied to experimental data to generate a corresponding graph to aid in assessing the effects of the drug combination. The corresponding graphs associated with the equations referred to above are the concentration-effect curve, isobologram curve and combination index curve, respectively.

Methods

In one aspect, the invention includes a method of treating or preventing viral infection in a subject in need thereof In certain embodiments, the method comprises administering to the subject a therapeutically effective amount of a pharmaceutically acceptable composition comprising at least one compound of the invention. In other embodiments, the viral infection is caused by at least one virus selected from the group consisting of a filovirus, arenavirus, rhabdovirus, paramyxovirus, retrovirus, and any combinations thereof.

In certain embodiments, the composition is administered to the subject by at least one route selected from oral, rectal, mucosal (e.g., by oral or nasal inhalation), transmucosal, topical (transdermal), or by intravenous, intradermal, intramuscular, subcutaneous, intracutaneous, intrauterine, epidural or intracerebroventricular injection. In other embodiments, the subject is further administered at least one additional compound useful for treating or preventing a viral infection. In yet other embodiments, the subject is a mammal. In yet other embodiments, the mammal is human. In yet other embodiments, the subject is not responsive to one or more commercially available antivirals.

Formulations/Administration

The compositions of the present invention may contain a pharmaceutical acceptable carrier, excipient and/or diluent, and may be administered by a suitable method to a subject. The compositions of the present invention may be formulated in various forms, including oral dosage forms or sterile injectable solutions, according to any conventional method known in the art. In other embodiments, the compositions may also be used as an inhalation-type drug delivery system. In yet other embodiments, the compositions of the invention may be formulated for injectable solutions.

The compositions may be formulated as powders, granules, tablets, capsules, suspensions, emulsions, syrup, aerosol, preparations for external application, suppositories and sterile injectable solutions. Suitable formulations known in the art are disclosed in, for example, Remington's Pharmaceutical Science (Mack Publishing Company, Easton Pa.).

Carriers, excipients and diluents that may be contained in the composition of the present invention include lactose, dextrose, sucrose, sorbitol, mannitol, xylitol, erythritol, maltitol, starch, acacia gum, alginate, gelatin, calcium phosphate, calcium silicate, cellulose, methyl cellulose, microcrystalline cellulose, polyvinyl pyrrolidone, water, methylhydroxybenzoate, propyl hydroxylbenzoate, talc, magnesium stearate or mineral oil.

Tablets may also contain such standard ingredients as binding and granulating agents such as polyvinylpyrrolidone, disintegrants (e.g. swellable crosslinked polymers such as crosslinked carboxymethylcellulose), lubricating agents (e.g. stearates), preservatives (e.g. parabens), antioxidants (e.g. BHT), buffering agents (for example phosphate or citrate buffers), and effervescent agents such as citrate/bicarbonate mixtures. Such excipients are well known and do not need to be discussed in detail here. Capsule formulations may be of the hard gelatin or soft gelatin variety and can contain the active component in solid, semi-solid, or liquid form. Gelatin capsules can be formed from animal gelatin or synthetic or plant derived equivalents thereof. The solid dosage forms (e.g.; tablets, capsules etc.) can be coated or un-coated, but typically have a coating, for example a protective film coating (e.g. a wax or varnish) or a release controlling coating. The coating (e.g. a Eudragit™ type polymer) can be designed to release the active component at a desired location within the gastro-intestinal tract. Thus, the coating can be selected so as to degrade under certain pH conditions within the gastrointestinal tract, thereby selectively release the compound in the stomach or in the ileum or duodenum. Alternatively or additionally, the coating can be used as a taste masking agent to mask unpleasant tastes such as bitter tasting drugs. The coating may contain sugar or other agents that assist in masking unpleasant tastes. Instead of, or in addition to, a coating, the antibiotic can be presented in a solid matrix comprising a release controlling agent, for example a release delaying agent which may be adapted to selectively release the compound under conditions of varying acidity or alkalinity in the gastrointestinal tract. Alternatively, the matrix material or release retarding coating can take the form of an erodible polymer (e.g., a maleic anhydride polymer) which is substantially continuously eroded as the dosage form passes through the gastrointestinal tract. As a further alternative, the active compound can be formulated in a delivery system that provides osmotic control of the release of the compound. Osmotic release and other delayed release or sustained release formulations may be prepared in accordance with methods well known to those skilled in the art. The pharmaceutical formulations may be presented to a patient in "patient packs" containing an entire course of treatment in a single package, usually a blister pack. Patient packs have an advantage over traditional prescriptions, where a pharmacist divides a patient's supply of a pharmaceutical from a bulk supply, in that the patient always has access to the package insert contained in the patient pack, normally missing in patient prescriptions. The inclusion of a package insert has been shown to improve patient compliance with the physician's instructions. Each tablet, capsule, caplet, pill, etc. can be a single dose, with a dose, for example, as herein discussed, or a dose can be two or more tablets, capsules, caplets, pills, etc; for example if a tablet, capsule etc is 125 mg and the dose is 250 mg, the patient may take two tablets, capsules and the like, at each interval there is to administration.

The compositions of the present invention may be formulated with commonly used diluents or excipients, such as fillers, extenders, binders, wetting agents, disintegrants, or surfactants. Solid formulations for oral administration include tablets, pills, powders, granules, or capsules, and such solid formulations comprise, in addition to the composition, at least one excipient, for example, starch, calcium carbonate, sucrose, lactose or gelatin. In addition to simple excipients, lubricants such as magnesium stearate or talc may also be used. Liquid formulations for oral administration include suspensions, solutions, emulsions and syrup, and may contain various excipients, for example, wetting agents, flavoring agents, aromatics and preservatives, in addition to water and liquid paraffin, which are frequently used simple diluents.

Formulations for parenteral administration include sterilized aqueous solutions, non-aqueous solutions, suspensions, emulsions, freeze-dried preparations, and suppositories. As non-aqueous solvents or suspending agents, propylene glycol, polyethylene glycol, plant oils such as olive oil, or injectable esters such as ethyl oleate may be used. As the base of the suppositories, witepsol, Macrogol, Tween 61, cacao butter, laurin fat, or glycerogelatin may be used.

The compounds for use in the method of the invention may be formulated in unit dosage form. The term "unit dosage form" refers to physically discrete units suitable as unitary dosage for patients undergoing treatment, with each unit containing a predetermined quantity of active material calculated to produce the desired therapeutic effect, optionally in association with a suitable pharmaceutical carrier. The unit dosage form may be for a single daily dose or one of multiple daily doses (e.g., about 1 to 4 or more times per day). When multiple daily doses are used, the unit dosage form may be the same or different for each dose.

The compositions of the present invention may be administered to a subject by various routes. All modes of administration are contemplated, for example, orally, rectally, mucosally (e.g., by oral or nasal inhalation), transmucosally, topically (transdermal), or by intravenous, intradermal, intramuscular, subcutaneous, intracutaneous, intrauterine, epidural or intracerebroventricular injection.

Dosing

The contemplated dose of the pharmaceutical compositions of the present invention varies depending on the patient's condition and weight, the severity of the disease, the type of drug, and the route and period of administration and may be suitably selected by those skilled in the art. For certain effects, the pharmaceutical composition of the present invention may be administered at a dose of 0.01-100 mg/kg/day. The administration may be anywhere from 1 to 4 times daily, e.g., once, twice, three times or four times daily. The maximum amount administered in a 24 hour period may be up to 1,500 mg. The administration may be over a course of 2 to 30 days, e.g., 3 to 21 days, such as 7, 10 or 14 days. The skilled person can adjust dosing depending on the subject's body weight and overall health condition and the purpose for administering the compound. Repeated courses of treatment may be pursued depending on the response obtained. The skilled artisan will be able to determine appropriate dosages depending on these and other factors.

A suitable dose of a compound of the present invention may be in the range of from about 0.01 mg to about 5,000 mg per day, such as from about 0.1 mg to about 1,000 mg, for example, from about 1 mg to about 500 mg, such as about 5 mg to about 250 mg per day. The dose may be administered in a single dosage or in multiple dosages, for example from 1 to 4 or more times per day. When multiple dosages are used, the amount of each dosage may be the same or different. For example, a dose of 1 mg per day may be administered as two 0.5 mg doses, with about a 12-hour interval between doses.

It is understood that the amount of compound dosed per day may be administered, in non-limiting examples, every day, every other day, every 2 days, every 3 days, every 4 days, or every 5 days. For example, with every other day administration, a 5 mg per day dose may be initiated on Monday with a first subsequent 5 mg per day dose administered on Wednesday, a second subsequent 5 mg per day dose administered on Friday, and so on.

Controlled Release Formulations and Drug Delivery Systems

In certain embodiments, the formulations of the present invention may be, but are not limited to, short-term, rapid-offset, as well as controlled, for example, sustained release, delayed release and pulsatile release formulations.

The term sustained release is used in its conventional sense to refer to a drug formulation that provides for gradual release of a drug over an extended period of time, and that may, although not necessarily, result in substantially constant blood levels of a drug over an extended time period. The period of time may be as long as a month or more and should be a release which is longer that the same amount of agent administered in bolus form.

For sustained release, the compounds may be formulated with a suitable polymer or hydrophobic material which provides sustained release properties to the compounds. As such, the compounds for use the method of the invention may be administered in the form of microparticles, for example, by injection or in the form of wafers or discs by implantation.

In certain embodiments of the invention, the compounds of the invention are administered to a patient, alone or in combination with another pharmaceutical agent, using a sustained release formulation.

The term delayed release is used herein in its conventional sense to refer to a drug formulation that provides for an initial release of the drug after some delay following drug administration and that mat, although not necessarily, includes a delay of from about 10 minutes up to about 12 hours.

The term pulsatile release is used herein in its conventional sense to refer to a drug formulation that provides release of the drug in such a way as to produce pulsed plasma profiles of the drug after drug administration.

The term immediate release is used in its conventional sense to refer to a drug formulation that provides for release of the drug immediately after drug administration.

As used herein, short-term refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes and any or all whole or partial increments thereof after drug administration after drug administration.

As used herein, rapid-offset refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes, and any and all whole or partial increments thereof after drug administration.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only, and the invention is not limited to these Examples, but rather encompasses all variations that are evident as a result of the teachings provided herein.

Materials:

Unless otherwise noted, all remaining starting materials were obtained from commercial suppliers and used without purification. Final products are typically isolated as acid addition salts unless noted otherwise.

Cell Lines, Viruses, and Antibodies:

HEK293T, BHK-21, and BSR cells were maintained in Dulbecco's modified Eagle's medium (DMEM) supplemented with 10% fetal calf serum (FCS), penicillin (100 U/ml)/streptomycin (100 µg/ml) at 37° C. in a humidified 5% CO2 incubator. Anti-GAPDH (ab8245) and anti-Hsp70 antibodies [BRM-22] (ab6535) were purchased from Abcam (Cambridge, Mass.); mouse anti-flag monoclonal antibody (F1804-200UG) and mouse anti-β-actin (A1978-200 UL) were obtained from Sigma-Aldrich (St. Louis, Mo.); polyclonal anti-EBOV VP40 antibody was generated by ProSci Incorporated (Poway, Calif.); anti-VSV-M monoclonal antibody 23H12 was provided by D. Lyles (Winston-Salem, N.C.); anti-RABV M is a rabbit polyclonal serum raised against an N-terminal peptide (aa 4-19) from SAD B19; anti-LFV-Z is a rabbit polyclonal serum provided by S. Urata (Nagasaki, Japan) (Urata et al., 2006, J. Virol. 80:4191-4195). VSV-WT (Indiana strain), VSV recombinant M40, and VSV-PY>A4 were propagated in BHK-21 cells (Irie et al., 2004, J. Virol. 78:2657-2665; Irie et al., 2005, Virol. 336:291-298; Irie et al., 2004, J. Virol. 78:7823-7827). RABV (SPBN) is derived from the SAD B19 vaccine strain (Gomme et al., 2010, J. Virol. 84:2820-2831).

Test Compounds:

All compounds were >95% pure (as determined independently using LC/MS [Micromass ZQ Mass Spectrometer with Waters 2695 HPLC with 996 diode array detector]), dissolved in DMSO at concentrations of 10 or 100 mM, and stored at −20° C. Compound 1 (Z106187460) was purchased from ChemDiv (San Diego, Calif.). Compounds 2 (Amb207302), 3 (Amb21795400), 4 (Amb123203), 5 (Amb21795397), and 6 (Amb21639324) were purchased from Ambinter (Orléans, FRANCE).

Plasmids:

pCAGGS-based plasmids expressing EBOV (Zaire) VP40 and Flag-tagged MARV (Muskoke) VP40 were described in previously (Liu et al., 2010, Future Virol. 5:481-491; Licata et al., 2003, J. Virol. 77:1812-1819; Lu et al., 2013, J. Virol. 87:7777-7780). CYFP-mVP40 was described in Liu et al., 2011, J. Infect. Dis. 204 Suppl 3:S817-824).

Plasmid NYFP-Nedd4 was generated by amplifying the human Nedd4 ORF using standard PCR techniques and joining it to the NYFP fragment. The NYFP-Nedd4 fusion gene was cloned into the SmaI and NheI sites of the pCAGGS vector. The plasmid expressing LFV Z-WT protein (pCLFV-Z) was provided by S. Urata (Nagasaki, Japan) (Urata et al., 2006, J. Virol. 80:4191-4195). A pCAGGS-based plasmid expressing LFV-Z- ΔPPPY was constructed by standard PCR and cloning techniques.

Bimolecular Complementation (BiMC) Assay:

BiMC in HEK293T cells was performed as described previously in Liu et al., 2011, J. Infect. Dis. 204 Suppl 3:S817-824. Briefly, HEK293T cells were co-transfected with CYFP-mVP40 and NYFP-Nedd4 for 4-5 hours, and the cells were then treated with the indicated concentrations of 4, 5, or 6 for an additional 24 hours. Cell nuclei were stained with NucBlue Live Cell Stain reagent (Life Technologies) according to the manufacturer's instructions. Cells were examined by fluorescence microscopy.

VLP Budding Assay and Western Blotting:

VLP budding assays and Western blotting were performed as described previously in McCarthy et al., 2007, J. Virol. 81:11452-11460; Liu et al., 2010, J. Virol. 84:2294-2303).

Virus Budding and Titration:

To evaluate the effect of compounds on the release of VSV-WT, recombinant VSV-M40, or mutant VSV PY>A4, HEK293T cells in collagen-coated 6-well plates were infected with the appropriate virus at an MOI of 0.1 for 1 hour. The inoculum was removed, cells were washed 3X with PBS, and then incubated in serum-free OPTI-MEM in the presence of DMSO alone (mock), or the appropriate compounds at the indicated concentrations. Virions from the culture media were harvested at 8 hours post-infection and centrifuged at 2,500 rpm for 10 minutes at 4° C. to remove cellular debris. Cells were lysed in RIPA buffer (50mM Tris HCl pH 8, 150 mM NaCl, 1% NP-40, 0.5% sodium deoxycholate, 0.1% SDS and protease inhibitor).

VSV M or M40 proteins in cell extracts were analyzed by SDS-PAGE and Western-blot with anti-VSV M monoclonal antibody 23H12, followed by anti-mouse IgG HRP-conjugated secondary antibody. For virus titration, BHK-21 cells in 6-well plates were washed 1X with PBS and inoculated with 200 µl of 10-fold serial dilutions of virus in serum free DMEM in triplicate and incubated for 1 hour. The inoculum was removed and the cells were washed 3X with PBS and incubated with 2.0 mls of Eagle's MEM containing 5% FBS and 1% methylcellulose at 37° C. for 36-48 hour until plaques were observed. Cells were washed 2X with PBS, fixed with methanol and stained with 1% crystal violet solution.

To evaluate the effect of compounds on the release of RABV, HEK293T cells were infected with SPBN at an MOI of 0.1 in the absence or presence of the probe, and cells were incubated at 34° C. Virus-containing supernatants were harvested at the indicated times post-infection, and titers were determined in duplicate on BSR cells. RABV M protein was detected by Western blotting of HEK293T cells infected with SPBN at an MOI of 10 for 36 hours.

Structure/Activity Studies:

Compound 1 was identified via an in silico screen involving computational docking of over 4.8 million drug-like compounds from the ZINC database into the published structure between the viral PPxY motif and the host WW-domain of Nedd4 (Kanelis et al., 1998. Biochem. Cell Biol. 76:341-350; Otte et al., 2003, Protein Sci. 12:491-500) with AutoDock 4.0, followed by energy minimization using CHARMM with the MMFF force field, and ranking with Accelrys LigScore2 (FIG. 1) (Morris et al., 2009, J. Comp. Chem. 30:2785-2791; Zhang et al., 2008, BMC Bioinform. 9:126).

Experimentally testing the top twenty scoring compounds as described (FIG. 1) allowed for the identification of initial hit 1. Compound 1 was then dissected into two fragments as shown by the red colored dissection line in FIG. 1 and the 2-piperidin-3-yl-benzothiazole fragment (left side) and 1-acetyl-3-(2,2,2-trifluoro-ethyl)-urea fragment (right side) was used for substructure searching (SSS) of the Ambinter (Orléans, FRANCE) commercial compound database.

Ten commercially available compounds (five from each fragment substructure) were evaluated. This allowed for the identification of more potent compounds, namely congener 2 obtained from SSS of the left side fragment and analog 3 from SSS of the right side fragment. Structurally related inactive compound 6, used as a negative control in later studies, was also identified (SSS analog of right hand fragment of 1).

Substructure/similarity searching for analogs of 2 allowed for identification of two additional analogs of 2. One of these two was compound 4 which proved to be more potent than 2. Substructure/similarity searching for analogs of 3 allowed for the identification of eight additional analogs of 3. In certain embodiments, compound 5 stood out as the most potent, exceeding the potency of 3.

Example 1: Chemical Synthesis of Exemplary Compounds

Compound 3h: 2-((3-methylquinoxalin-2-yl)thio)-N-(phenylcarbamoyl)acetamide

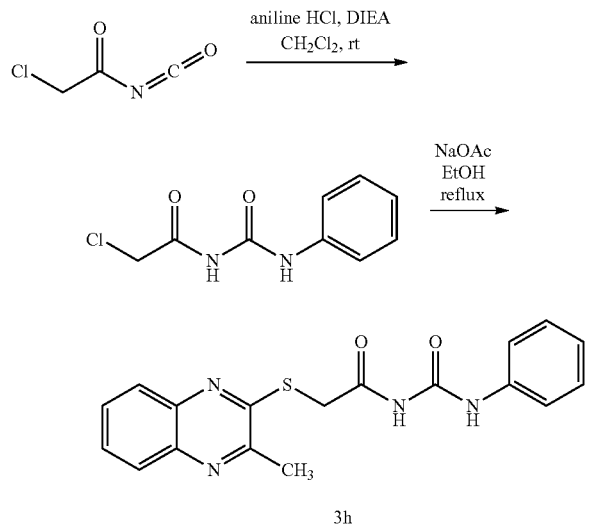

3h

Compound 3n: 6-(3-Methyl-quinoxalin-2-ylsulfanylmethyl)-1H-pyrimidine-2,4-dione

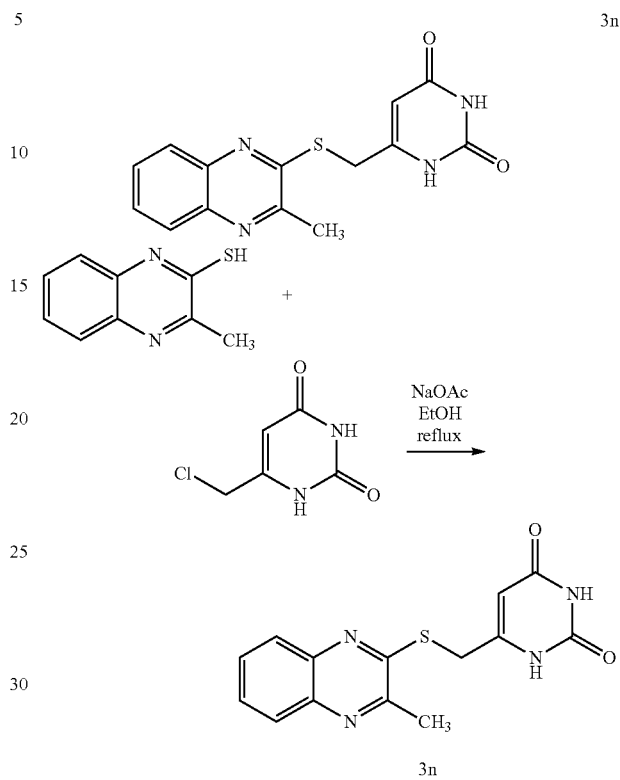

3n

3-Methylquinoxaline-2-thiol (25 mg, 0.14 mmol), 6-(chloromethyl)uracil (23 mg, 0.14 mmol) and sodium acetate (17 mg, 0.21 mmol) were combined in EtOH (700 μL) and refluxed for 30 minutes. The reaction was cooled, and the solids were collected by vacuum filtration and washed with EtOH, to obtain the title compound as a pink powder (41 mg, 95% yield). LCMS (ESI) m/z 301.4 (M+1)$^+$, retention time 3.4 min. $^1$H NMR (300 MHz, d6-DMSO) δ 11.1 (br. s., 1H), 11.0 (br. s., 1H), 8.0-7.9 (m, 2H), 7.8-7.7 (m, 2H), 5.7-5.6 (m, 1H), 4.3 (s, 2H), 2.6 (s, 3H).

Compound 5: 1-[2-(3-Methyl-quinoxalin-2-ylsulfanyl)-acetyl]-3-phenyl-urea

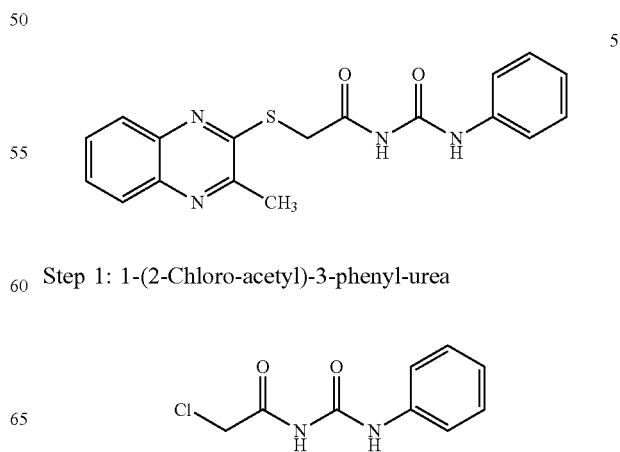

5

Step 1: 1-(2-Chloro-acetyl)-3-phenyl-urea

2-Chloroacetylisocyanate (102 µL, 1.2 mmol) was added dropwise to a room temperature stirred solution of aniline hydrochloride (130 mg, 1.0 mmol) and DIEA (174 µL, 1.0 mmol) in DCM (5mL). The reaction was stirred overnight at room temperature. The reaction was purified by flash chromatography (12 g silica, 0-25% EtOAc/Hexane) to obtain the title compound as a white powder (195 mg, 95% yield). Retention time 3.9 min. $^1$H NMR (300 MHz, DMSO) δ=10.87 (s, 1H), 10.12 (s, 1H), 7.53-7.47 (m, 2H), 7.32 (t, J=7.5 Hz, 2H), 7.08 (t, J=7.2 Hz, 1H), 4.37 (s, 2H).

Step 2: 1-[2-(3-Methyl-quinoxalin-2-ylsulfanyl)-acetyl]-3-phenyl-urea

In a similar manner to 3n, 1-(2-chloro-acetyl)-3-phenyl-urea was used in place of 6-(chloromethyl)uracil to afford the title compound (50 mg, quantitative yield). LCMS (ESI) m/z 353.3 (M+1)$^+$, retention time 5.3 min. $^1$H NMR (300 MHz, d$_6$-DMSO) δ11.1 (br. s., 1H), 10.3 (br. s., 1H), 7.9 (d, J=7.7 Hz, 1H), 7.8-7.6 (m, 3H), 7.5 (d, J=8.2 Hz, 2H), 7.3 (t, J=7.8 Hz, 2H), 7.1-7.0 (m, 1H), 4.3 (s, 2H), 2.6 (s, 3H).

In a similar manner to 5, the following compounds were prepared:

| Cpd. | Structure | LCMS (ESI) m/z (M + 1)$^+$ | LCMS retention time (min) | $^1$H NMR (300 MHz, d$_6$-DMSO) δ |
|---|---|---|---|---|
| 3o | 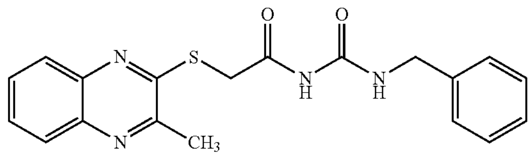 [SMILES: Cc1nc2ccccc2nc1SCC(=O)NC(=O)NCc1ccccc1] | 367.4 | 5.0 | 10.9 (br. s., 1H), 8.6 (br. s., 1H), 7.9 (d, J = 7.5 Hz, 1H), 7.8-7.7 (m, 3H), 7.3-7.1 (m, 5H), 4.3 (d, J = 6.2 Hz, 2H), 4.2 (s, 2H), 2.6 (s, 3H) |
| 3p | 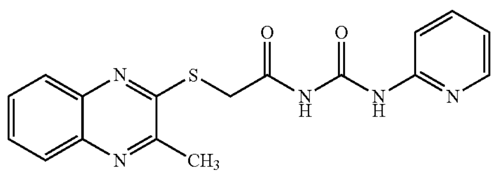 [SMILES: Cc1nc2ccccc2nc1SCC(=O)NC(=O)Nc1ccccn1] | 354.4 | 3.9 | 11.3 (br. s., 1H), 10.7 (s, 1H), 8.2 (d, J = 4.9 Hz, 1H), 8.0-7.9 (m, 2H), 7.8-7.6 (m, 4H), 7.1 (t, J = 6.1 Hz, 1H), 4.3 (s, 2H), 2.6 (s, 3H) |
| 3q | 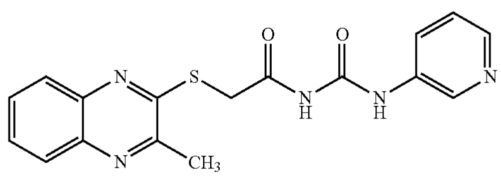 [SMILES: Cc1nc2ccccc2nc1SCC(=O)NC(=O)Nc1cccnc1] | 354.4 | 3.2 | 11.3 (br. s., 1H), 10.3 (s, 1H), 8.7 (d, J = 2.6 Hz, 1H), 8.3 (dd, J = 1.2, 4.7 Hz, 1H), 8.0-7.9 (m, 2H), 7.8-7.6 (m, 3H), 7.3 (dd, J = 4.7, 8.5 Hz, 1H), 4.3 (s, 2H), 2.6 (s, 3H) |
| 3r | 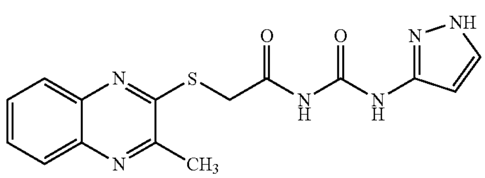 [SMILES: Cc1nc2ccccc2nc1SCC(=O)NC(=O)Nc1cc[nH]n1] | 343.4 | 3.7 | 12.4 (br. s., 1H), 11.2 (br. s., 1H), 10.4 (br. s., 1H), 7.9 (d, J = 7.6 Hz, 1H), 7.8-7.6 (m, 4H), 6.4 (s, 1H), 4.3 (s, 2H), 2.6 (s, 3H) |
| 3s | 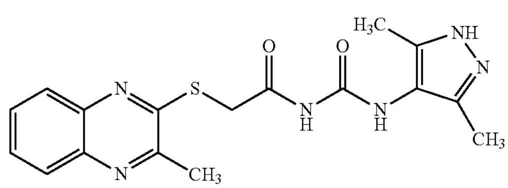 [SMILES: Cc1nc2ccccc2nc1SCC(=O)NC(=O)Nc1c(C)n[nH]c1C] | 371.4 | 3.4 | 12.2 (br. s., 1H), 11.0 (br. s., 1H), 9.2 (s, 1H), 7.9 (dd, J = 1.5, 7.9 Hz, 1H), 7.8-7.6 (m, 3H), 4.3 (s, 2H), 2.6 (s, 3H), 1.9 br. s., 6H) |
| 3t | 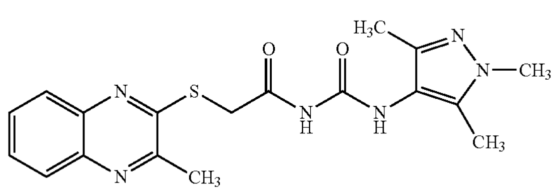 [SMILES: Cc1nc2ccccc2nc1SCC(=O)NC(=O)Nc1c(C)nn(C)c1C] | 385.5 | 3.8 | 11.0 (br. s., 1H), 9.2 (s, 1H), 8.0 (d, J = 7.6 Hz, 1H), 7.8-7.6 (m, 3H), 4.3 (s, 2H), 3.6 (s, 3H), 2.6 (s, 3H), 2.0 (s, 3H), 1.9 (s, 3H) |
| 3u | 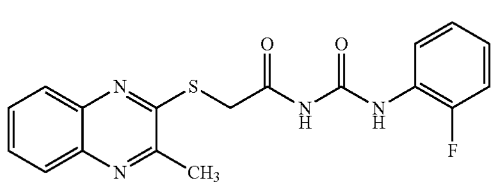 [SMILES: Cc1nc2ccccc2nc1SCC(=O)NC(=O)Nc1ccccc1F] | 371.4 | 5.4 | 11.4 (s, 1H), 10.6 (br. s., 1H), 8.1 (dt, J = 1.8, 8.1 Hz, 1H), 7.9 (d, J = 7.7 Hz, 1H), 7.8-7.6 (m, 3H), 7.3-7.0 (m, 3H), 4.3 (s, 2H), 2.6 (s, 3H) |

-continued

| Cpd. | Structure | LCMS (ESI) m/z (M + 1)+ | LCMS retention time (min) | $^1$H NMR (300 MHz, $d_6$-DMSO) δ |
|---|---|---|---|---|
| 3v | 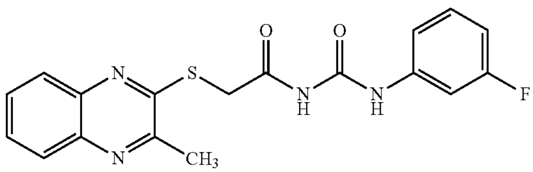 [SMILES: Cc1nc2ccccc2nc1SCC(=O)NC(=O)Nc1cccc(F)c1] | 371.4 | 5.5 | 11.2 (br. s., 1H), 10.5 (s, 1H), 7.9 (d, J = 7.7 Hz, 1H), 7.8-7.6 (m, 3H), 7.5 (dt, J = 2.2, 11.5 Hz, 1H), 7.3-7.2 (m, 2H), 6.9-6.8 (m, 1H), 4.3 (s, 2H), 2.6 (s, 3H) |
| 3w | 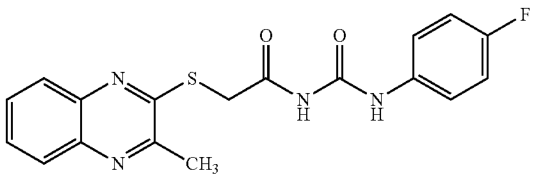 [SMILES: Cc1nc2ccccc2nc1SCC(=O)NC(=O)Nc1ccc(F)cc1] | 371.4 | 5.3 | 11.1 (br. s., 1H), 10.3 (s, 1H), 8.0 (d, J = 7.6 Hz, 1H), 7.8-7.6 (m, 3H), 7.6-7.5 (m, 2H), 7.2-7.1 (m, 2H), 4.3 (s, 2H), 2.6 (s, 3H) |
| 3y* | 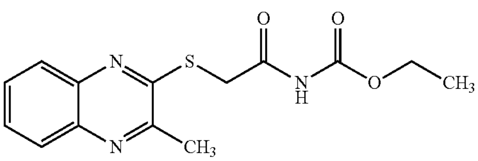 [SMILES: CCOC(=O)NC(=O)CSc1nc2ccccc2nc1C] | 306.4 | 4.3 | (in CD$_3$OD) 7.97-7.83 (m, 2H), 7.74-7.60 (m, 2H), 4.38-4.21 (m, 4H), 2.69 (s, 3H), 1.33 (t, J = 7.0 Hz, 3H) |
| 3z* | 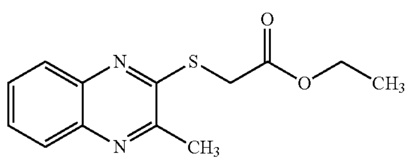 [SMILES: CCOC(=O)CSc1nc2ccccc2nc1C] | 263.3 | 5.2 | (in CD$_3$OH) 7.95-7.79 (m, 2H), 7.71-7.61 (m, 2H), 4.25-4.13 (m, 4H), 2.67 (s, 3H), 1.33-1.20 (m, 3H) |

*3-(2-Chloro-acetyl)-1-methyl-1-phenyl-urea was the alkylating reagent for this reaction but EtOH further reacted with the product to give these two products.

Compound 3aa: 1-Methyl-3-[2-(3-methyl-quinoxalin-2-yl-sulfanyl)-acetyl]-1-phenyl-urea

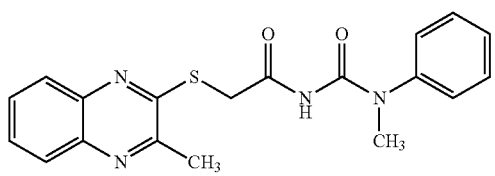

3aa

A mixture of 3-methylquinoxaline-2-thiol (25 mg, 0.14 mmol) and 3-(2-chloro-acetyl)-1-methyl-1-phenyl-urea (32 mg, 0.14 mmol, similar synthesis as 5, Step 1, but no base was used) in DMF (710 µL) was heated overnight at 100° C. The reaction was purified by prep HPLC and freeze dried from dioxane to afford the title compound as a grey powder (10 mg, 20% yield). LCMS (ESI) m/z 389.5 (M+Na) retention time 5.2 min. $^1$H NMR (300 MHz, CD$_3$OD) δ=7.93-7.74 (m, 2H), 7.72-7.55 (m, 2H), 7.55-7.45 (m, 4H), 7.42-7.23 (m, 1H), 4.04 (s, 2H), 3.31-3.29 (m, 3H), 2.63 (s, 3H).

Compound 3x: 1-[2-(3-Methyl-quinoxalin-2-yloxy)-acetyl]-3-phenyl-urea

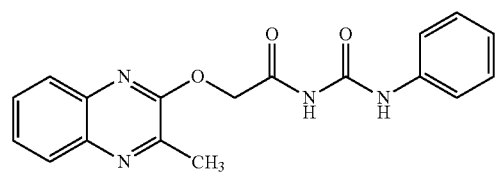

3x

A mixture of 3-methyl-2-quinoxalinol (25 mg, 0.16 mmol), 1-(2-chloro-acetyl)-3-phenyl-urea (33 mg, 0.16 mmol), and K$_2$CO$_3$ (32 mg, 0.23 mmol) in DMF (780 µL) was stirred at 60° C. for 3 hours. The reaction was partitioned between water and EtOAc. Brine was added to break up the emulsion formed. The layers were separated, and the aqueous layer was extracted twice more with EtOAc. The combined organic extracts were washed with brine, dried over Na$_2$SO$_4$, filtered and concentrated in vacuum. The residue was purified by prep HPLC and freeze dried from dioxane to afford the title compound as a white powder (32 mg, 62% yield). LCMS (ESI) m/z 337.4 (M+1)+ retention time 4.4 min. $^1$H NMR (300 MHz, $d_6$-DMSO) δ11.1 (br. s., 1H), 10.1 (br. s., 1H), 7.8 (d, J=7.6 Hz, 1H), 7.6-7.5 (m, 4H), 7.4-7.2 (m, 3H), 7.1 (t, J=7.8 Hz, 1H), 5.2 (s, 2H), 2.4 (s, 3H).

Compound 3ab: 1-12-(3-Benzyl-quinoxalin-2-ylsulfanyl)-acetyl1-3-(3,5-dimethyl-1H-pyrazol-4-yl)-urea

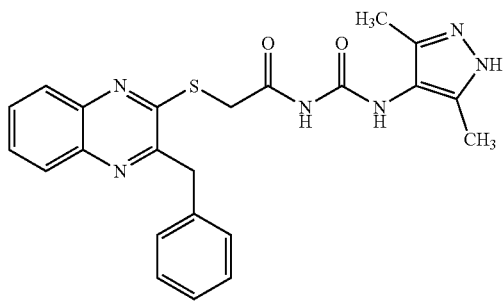

3ab

-continued

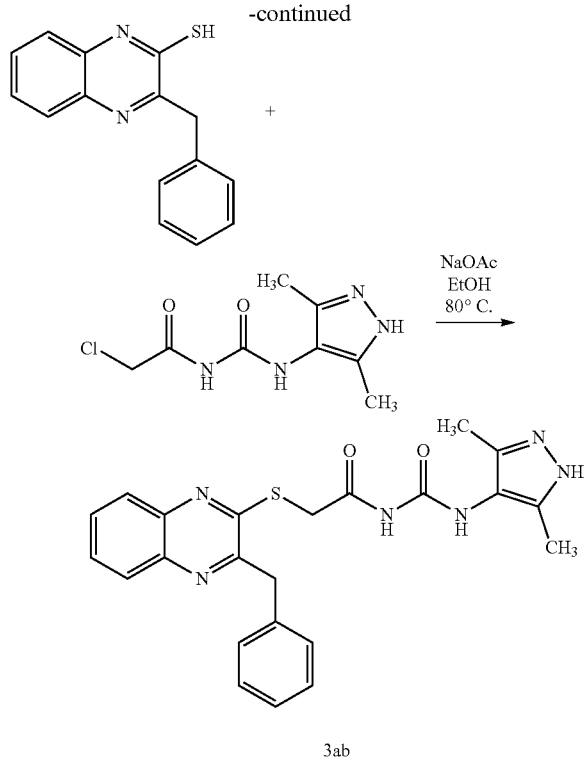

3ab

A mixture of 3-benzyl-quinoxaline-2-thiol (25 mg, 0.099 mmol), 1-(2-Chloro-acetyl)-3-(3,5-dimethyl-1H-pyrazol-4-yl)-urea (23 mg, 0.099 mmol, prepared in a similar manner as in 5, Step 1), and sodium acetate (12 mg, 0.15 mmol) in EtOH (700 µL) was heated overnight at 80° C. The solid that had precipitated out of the cooled reaction were collected by vacuum filtration, washing with ethanol, to give the title compound as a white powder (24 mg, 55% yield). LCMS (ESI) m/z 447.5 (M+1)$^+$ retention time 4.5 min. $^1$H NMR (300 MHz, DMSO) δ=12.08 (br. s., 1H), 10.95 (br. s., 1H), 9.12 (br. s., 1H), 7.99 (d, J=6.2 Hz, 1H), 7.83-7.67 (m, 3H), 7.30 (br. s., 4H), 7.22 (br. s., 1H), 4.32 (br. s., 2H), 4.22 (br. s., 2H), 1.92 (br. s., 6H).

In a similar manner to 3ab, the following compounds were prepared::

| Cpd. | Structure | LCMS (ESI) m/z (M + 1)$^+$ | LCMS retention time (min) | $^1$H NMR (300 MHz, d$_6$-DMSO) δ |
|---|---|---|---|---|
| 3ac | 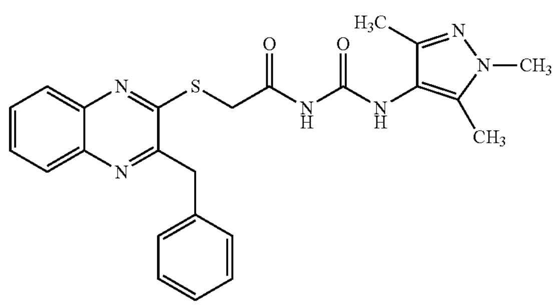 [SMILES: Cc1nn(C)c(C)c1NC(=O)NC(=O)CSc1nc2ccccc2nc1Cc1ccccc1] | 461.5 | 4.9 | 10.98 (br. s., 1H), 9.13 (s, 1H), 7.99 (d, J = 7.9 Hz, 1H), 7.82-7.67 (m, 3H), 7.33-7.20 (m, 5H), 4.32 (s, 2H), 4.23 (s, 2H), 3.58 (s, 3H), 1.97 (s, 3H), 1.88 (s, 3H) |
| 3ad | 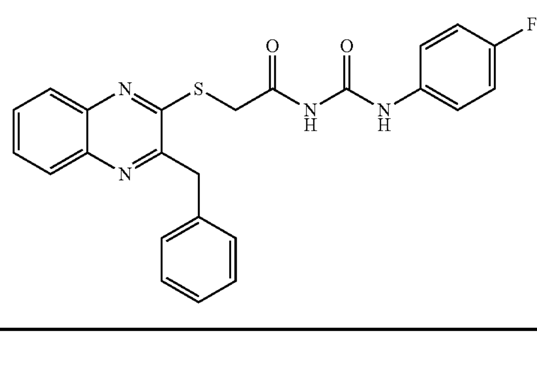 | 447.4 | 6.2 | 11.12 (br. s., 1H), 10.26 (s, 1H), 7.99 (d, J = 7.9 Hz, 1H), 7.83-7.66 (m, 3H), 7.56-7.46 (m, 2H), 7.33-7.08 (m, 7H), 4.32 (s, 2H), 4.26 (s, 2H) |

Compound 2h: 2-(4-Benzothiazol-2-yl-piperidin-1-yl)-N-(3,5-dimethyl-1-phenyl-1H-pyrazol-4-yl)-acetamide

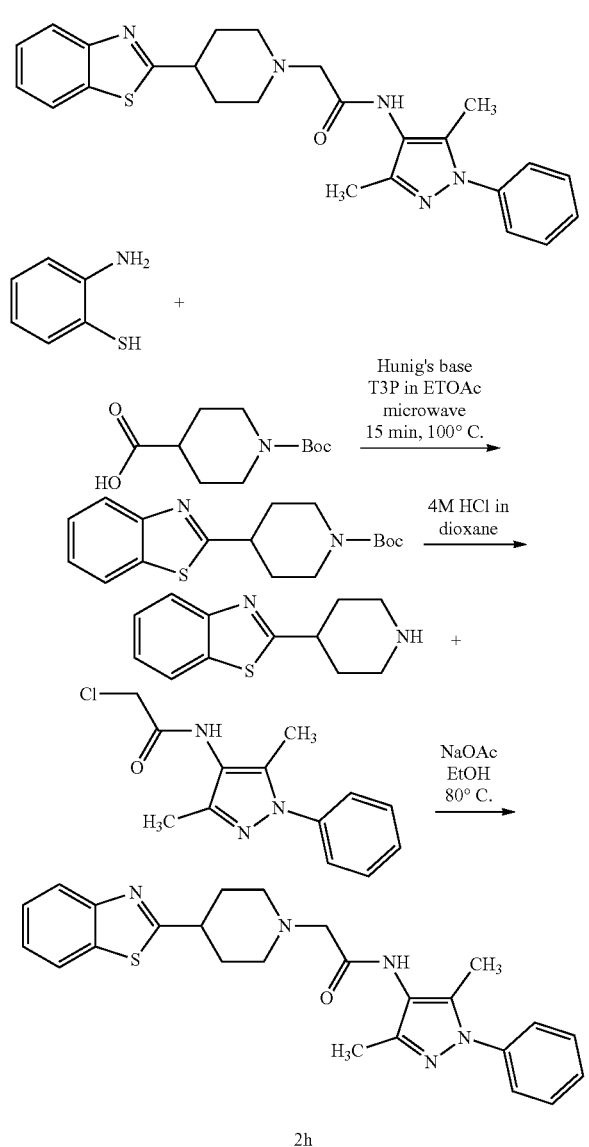

2h

Step 1: 4-Benzothiazol-2-yl-piperidine-1-carboxylic acid t-butyl ester

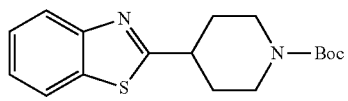 [SMILES: CC(C)(C)OC(=O)N1CCC(c2nc3ccccc3s2)CC1]

2-Aminothiophenol (100 mg, 0.80 mmol), N-Boc-piperidine-4-carboxylic acid (183 mg, 0.80 mmol), and Hunig's base (209 µL, 1.2 mmol) were combined in a 50+% solution of propylphosphoric anhydride (T3P) in EtOAc (471 µL, 0.80 mmol) in a microwave vial. The vial was capped and heated in the microwave for 15 minutes at 100° C. The cooled reaction was partitioned between water and EtOAc. The layers were separated, and the aqueous layer extracted twice more with EtOAc. The combined organic extracts were washed with brine, dried over Na$_2$SO$_4$, filtered and concentrated in vacuum. The residue was purified by flash chromatography (4g silica, 0-30% EtOAc/Hexane) to obtain the title compound as a pale yellow oil (220 mg, 87% yield). LCMS (ESI) m/z 319.4 (M+1)$^+$ retention time 5.92 min. $^1$H NMR (300 MHz, DMSO) δ=8.05 (d, J=7.8 Hz, 1H), 7.93 (d, J=8.0 Hz, 1H), 7.50-7.36 (m, 2H), 3.9-3.92 (m, 2H), 3.42 (m, 1H), 2.92 (m, 2H), 2.08 (dd, J=2.3, 12.9 Hz, 2H), 1.63 (dq, J=4.4, 12.2 Hz, 2H), 1.46-1.33 (m, 9H).

Step 2: 2-Piperidin-4-yl-benzothiazole

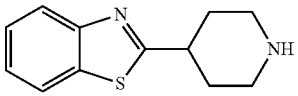 [SMILES: c1ccc2sc(C3CCNCC3)nc2c1]

To a solution of 4-benzothiazol-2-yl-piperidine-1-carboxylic acid tert-butyl ester (215 mg, 0.68 mmol) in dioxane (1.7 mL) was added 4M HCL in dioxane (1.7 mL, 6.8 mmol). The mixture was heated at 45° C. overnight. The reaction was cooled, then poured into aqueous NaHCO3 solution and extracted with EtOAc (3x). The combined organic extracts were washed with brine, dried over Na$_2$SO$_4$, filtered and concentrated to obtain the title compound as an orange solid. LCMS (ESI) m/z 219.3 (M+1)$^+$ retention time 2.7 min. $^1$H NMR (300 MHz, DMSO) δ=8.04 (d, J=7.9 Hz, 1H), 7.92 (d, J=7.9 Hz, 1H), 7.50-7.35 (m, 2H), 3.18-3.08 (m, 1H), 3.06-2.94 (m, 2H), 2.59 (dt, J=2.6, 12.0 Hz, 2H), 1.99 (d, J=12.3 Hz, 2H), 1.63 (dq, J=4.0, 12.1 Hz, 2H).

Step 3: 2-(4-Benzothiazol-2-yl-piperidin-1-yl)-N-(3,5-dimethyl-1-phenyl-1H-pyrazol-4-yl)-acetamide A mixture of 2-piperidin-4-yl-benzothiazole (25 mg, 0.11 mmol), 2-chloro-(3,4-dimethyl-1-phenyl-1H-pyrazol-4-yl)-acetamide (30 mg, 0.11 mmol, from Enamine), and Hunig's base (50 µL, 0.29 mmo) in DCM (570 µL) was stirred over the weekend at ambient temperature. The reaction was purified directly by flash chromatography (4 g, silica, 50-100% EtOAc/hexane) to afford the title compound as a white powder (36 mg, 71% yield). LCMS (ESI) m/z 446.5 (M+1)$^+$ retention time 3.8 min. $^1$H NMR (300 MHz, DMSO) δ=9.09 (s, 1H), 8.05 (d, J=7.7 Hz, 1H), 7.93 (d, J=8.2 Hz, 1H), 7.52-7.36 (m, 7H), 3.20-3.09 (m, 3H), 3.01 (d, J=11.1 Hz, 2H), 2.42-2.27 (m, 2H), 2.14 (s, 3H), 2.09 (m, 2H), 2.06 (s, 3H), 2.05 -1.95 (m, 2H).

Compound 2l: 2-[1-(1,3,5-Trimethyl-1H-pyrazol-4-ylmethyl)-piperidin-4-yl]-benzothiazole

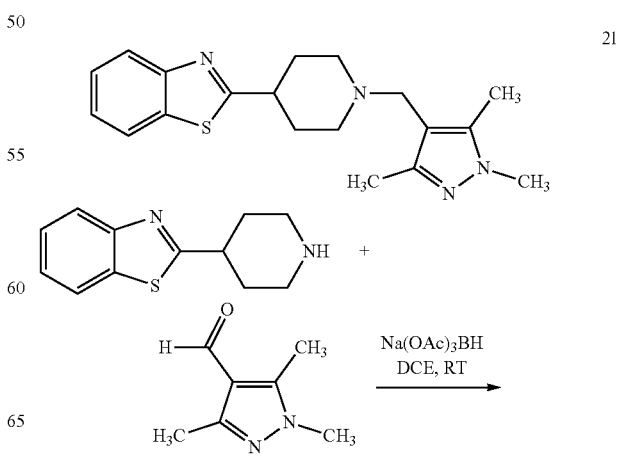

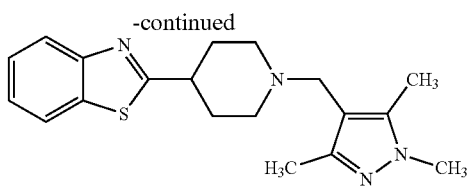

Sodium triacetoxyborohydride (17.5 mg, 0.082 mmol) was added to a solution of piperidin-4-yl-benzothiazole (15 mg, 0.069 mmol, Compound 2h, Step 2) and 1,3,5-trimethyl-1H-pyrazole-4-carbaldehyde (9.5 mg, 0.069 mmol, Bionet) in DCE (340 μL) at room temperature. After three hours, the reaction was purified directly by flash chromatography (4 g silica, 0-10% MeOH/DCM). The title compound was obtained as a yellow solid (15 mg, 65% yield). LCMS (ESI) m/z 341.4 (M+1)$^+$ retention time 3.2 min. $^1$H NMR (300 MHz, CD$_3$OD) δ=7.97-7.89 (m, 2H), 7.52-7.37 (m, 2H), 3.71 (s, 3H), 3.63 (s, 2H), 3.28-3.17 (m, 3H), 2.53 (dt, J=2.3, 11.7 Hz, 2H), 2.28 (s, 3H), 2.24 (m, 2H), 2.22 (s, 3H), 2.09-1.97 (m, 2H).

Compound 2m: 2-[1-(3,5-Dimethyl-1-phenyl-1H-pyrazol-4-ylmethyl)-piperidin-4-yl]-1-benzothiazole

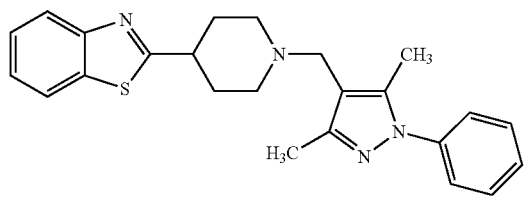

In a similar manner as 2l, the title compound was prepared using 3,5-dimethyl-1-phenyl-1H-pyrazole-4-carbaldehyde (Acros) instead of 1,3,5-trimethyl-1H-pyrazole-4-carbaldehyde. The title compound was obtained as a yellow solid (19 mg, 69% yield). LCMS (ESI) m/z 403.5 (M+1)$^+$ retention time 3.9 min. $^1$H NMR (300 MHz, CD$_3$OD) δ=7.98-7.90 (m, 2H), 7.57-7.37 (m, 7H), 3.66 (s, 2H), 3.28-3.20 (m, 3H), 2.57-2.46 (m, 2H), 2.32 (s, 3H), 2.30 (s, 3H), 2.30-2.24 (m, 2H), 2.10-1.96 (m, 2H).

Compound 2i: (4-Benzothiazol-2-yl-piperidin-1-yl)-(3,5-dimethyl-1H-pyrazol-4-yl)-methanone

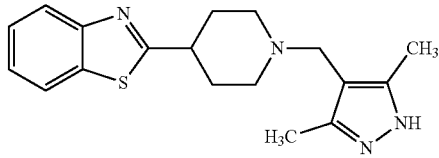

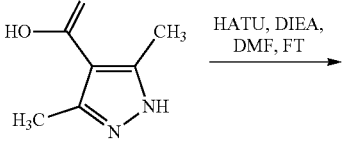

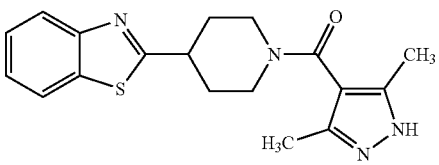

A mixture of 3,5-dimethyl-1H-pyrazole-4-carboxylic acid (9.6 mg, 0.069 mmol, Maybridge), piperidin-4-yl-benzothiazole (15 mg, 0.069 mmol, Compound 2h, Step 2), Hunig's base (24 μL, 0.137 mmol) and HATU (39 mg, 0.103 mmol) was stirred overnight at room temperature in DMF (343 μL). The reaction was purified directly by prep HPLC to give a pale yellow solid after freeze drying from dioxane (11.5 mg, 50% yield). LCMS (ESI) m/z 341.4 (M+1)$^+$ retention time 3.8 min. $^1$H NMR (300MHz, CD$_3$OD) δ=7.95 (m, 2H), 7.50 (m, 1H), 7.44-7.38 (m, 1H), 3.55-3.41 (m, 1H), 3.31-3.01 (m, 2H), 2.50 (m, 2H), 2.30 (s, 6H), 2.26-2.12 (m, 2H), 1.95-1.78 (m, 2H).

In a similar manner to 2i, the following compounds were prepared:

| Cpd. | Structure | LCMS (ESI) m/z (M + 1)$^+$ | LCMS retention time (min) | $^1$H NMR (300 MHz, d$_6$-DMSO) δ |
|---|---|---|---|---|
| 2j | 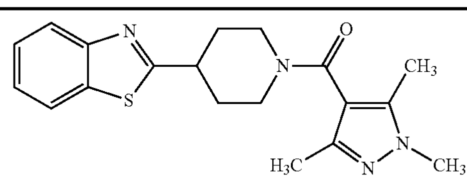 | 355.5 | 4.3 | 8.05 (d, J = 7.8 Hz, 1H), 7.94 (d, J = 8.0 Hz, 1H), 7.50-7.36 (m, 2H), 3.63 (s, 3H), 3.50-3.37 (m, 1H), 3.09 (m, 2H), 2.17 (s, 3H), 2.50 (m, 2H), 2.11 (m, 2H), 2.06 (s, 3H), 1.74-1.59 (m, 2H) |
| 2k | 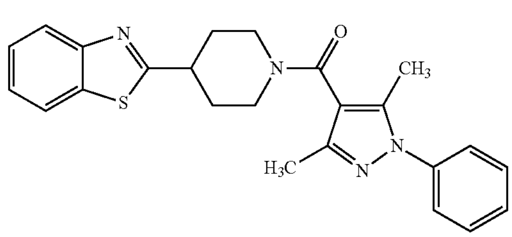 [SMILES: Cc1nn(-c2ccccc2)c(C)c1C(=O)N1CCC(c2nc3ccccc3s2)CC1] | 417.5 | 5.1 | 8.05 (d, J = 8.0 Hz, 1H), 7.95 (d, J = 8.0 Hz, 1H), 7.55-7.37 (m, 8H), 3.52-3.41 (m, 1H), 3.15 (m, 2H), 2.50 (m, 2H), 2.26 (s, 3H), 2.21-2.10 (m, 5H), 1.79-1.65 (m, 2H) |

Example 2: Identification of Host-Oriented Inhibitors Targeting Viral PPxY-host Nedd4 Interactions In one aspect, subversion of host Nedd4 E3 ubiquitin ligase by viral PPxY-type L-domains plays a role in efficient budding (virus-cell separation) of numerous RNA viruses including filoviruses, arenaviruses, and rhabdoviruses. In certain embodiments, small molecule inhibitors that block this virus-host interaction can reduce virus-cell separation and virus spread by concomitantly increasing the number of virions tethered to the plasma membrane.

Such candidate small molecule compounds were identified by using an in silico screening strategy to probe the reported interaction structure between the viral PPxY motif and the host WW-domain of Nedd4 (FIG. 1). This approach allowed for the identification of 1 as initial hit. Structural analogs of 1 based on the dissected fragments of 1 (FIG. 1) were evaluated, allowing for the the identification of more potent compounds 2-5 (FIG. 1).

Example 3: Anti-Budding Activity of Compound 1

Compound 1 was tested for its ability to block PPxY-dependent budding of MARV VP40 (mVP40) VLPs in a dose-dependent manner. Briefly, HEK293T cells were transfected with pCAGGS vector alone (FIG. 2A, lane 1) or an mVP40 expression plasmid in the absence (DMSO alone, lane 2) or presence of the indicated concentrations of 1 (lanes 3-6).

Figure 2A:
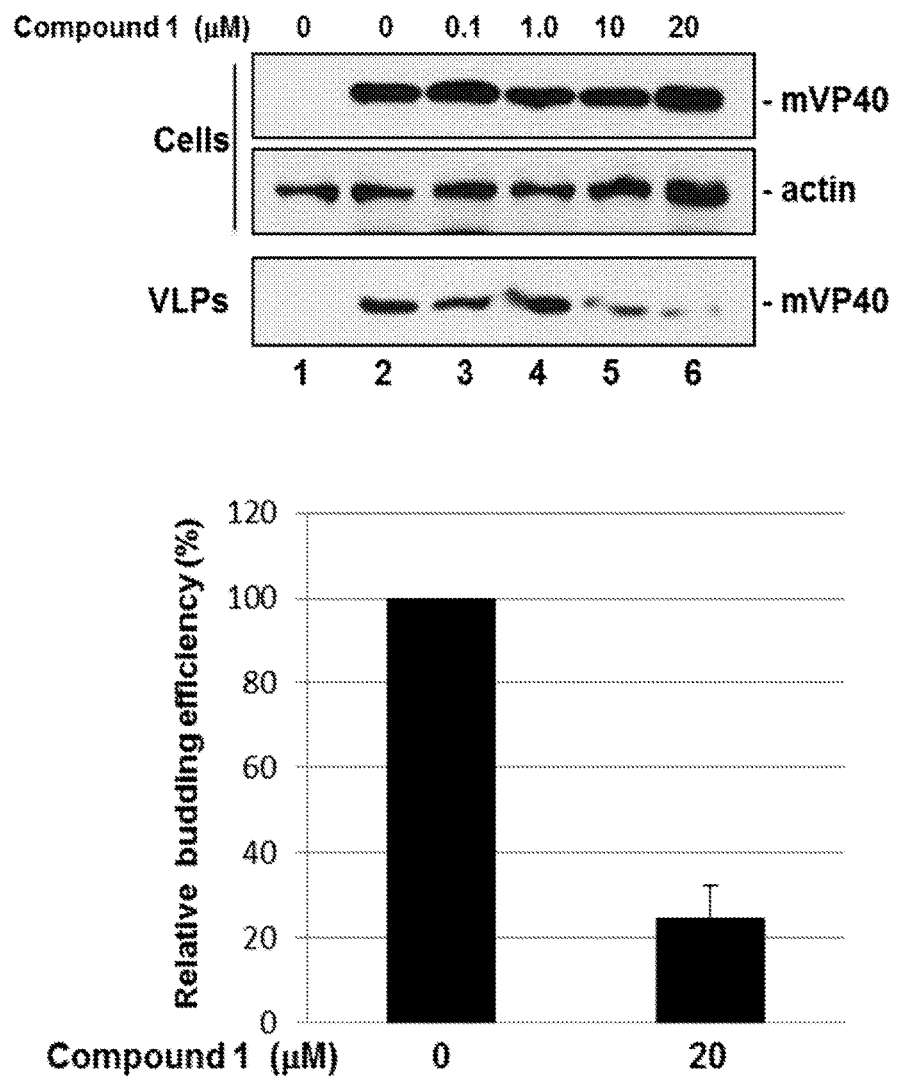

Compound 1 produced a dose-dependent inhibition of mVP40 VLP formation with an approximate 5-fold decrease in VLP egress at a concentration of 20 µM compared to controls (FIG. 2A; VLPs, lanes 2 and 6; bar graph). Compound 1 had no effect on expression levels of mVP40 or actin in cells at all drug concentrations tested (FIG. 2A; Cells, lanes 1-6).

Figure 2B:
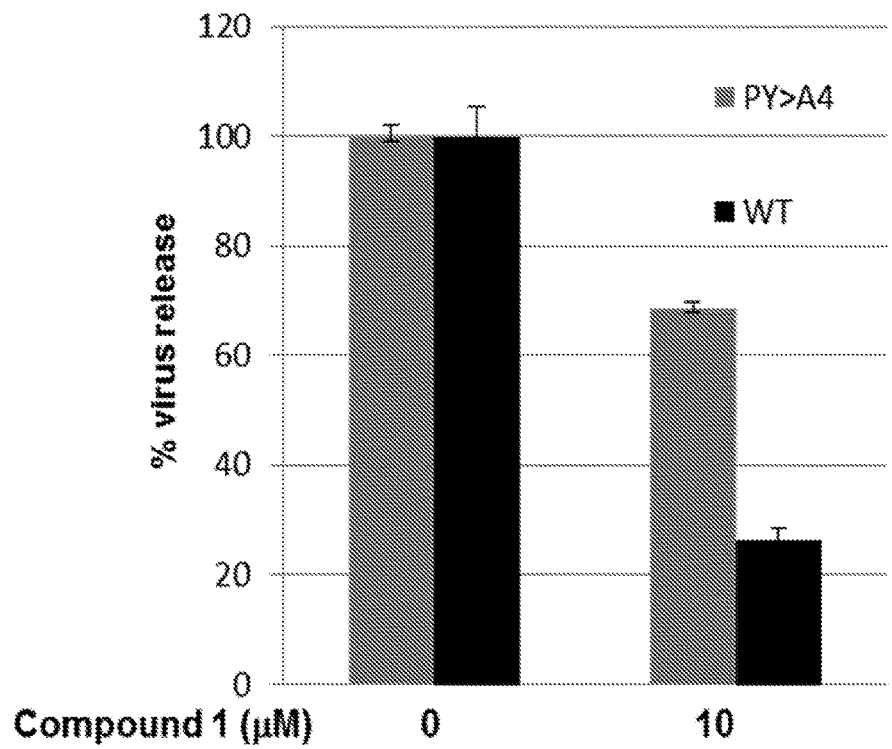
Figure 2B:
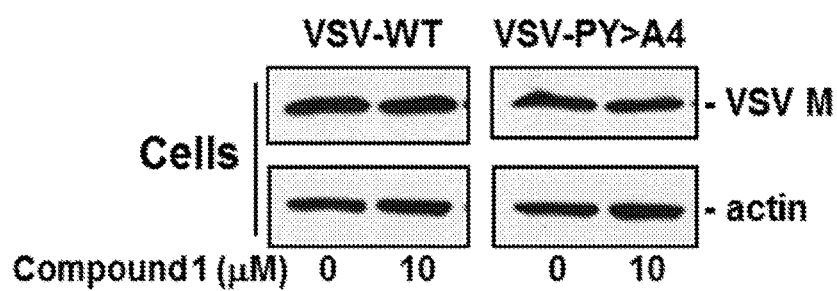

Studies were the perfroemd to determine whether 1 could inhibit budding of a PPxY-dependent virus from cell culture. Efficient egress of VSV is dependent on a functional PPxY L-domain within its M protein (Harty et al., 2001, J. Virol. 75:10623-10629; Craven et al., 1999, J. Virol. 73:3359-3365; Harty et al., 1999, J. Virol. 73:2921-2929; Irie et al., 2005, J. Virol. 79:12617-12622). Briefly, HEK293T cells were infected with VSV-WT or a PPxY mutant virus (VSV-PY>A4) in which the PPxY motif was changed to four alanines, in the absence (DMSO alone) or presence of 10 µM 1. Cell extracts and virus containing supernatants were harvested at 8 hours post-infection and analyzed for levels of M protein by Western blotting and viral titers by plaque assay, respectively (FIG. 2B). Relative release efficiency of VSV-WT and VSV-PY>A4 in the absence of 1 was set at 100% (FIG. 2B). In the presence of 10 µM 1, budding of mutant VSV-PY>A4 was reduced by <2-fold, whereas budding of VSV-WT was reduced by approximately 5-fold (FIG. 2B). Compound 1 had no effect on expression levels of actin or VSV M at a concentration of 10 µM as determined by Western blotting of infected cell extracts (FIG. 2B).

Example 4: Anti-Budding Activity of Compounds 2 and 3

Figure 3A:
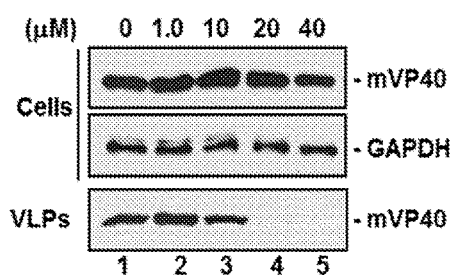
FIGS. 3A-3E illustrate the effect of 2 and 3 on budding of mVP40 and eVP40 VLPs. HEK293T cells transfected with mVP40 (FIGS. 3A-3B) were treated with DMSO alone (lane 1), or with the indicated concentrations of 2 (FIG. 3A, lanes 2-5), or 3 (FIG. 3B, lanes 2-4). Cells and VLPs were harvested at 24 hours post-transfection, and mVP40 was detected by Western blot. A Western blot control for cellular GAPDH in cells is illustrated HEK293T cells transfected with eVP40 (FIGS. 3C-3D) were treated with DMSO alone (lane 1), or with the indicated concentrations of 2 (FIG. 3C, lanes 2-5), or 3 (FIG. 3D, lanes 2-6). Cells and VLPs were harvested at 24 hours post-transfection, and eVP40 was detected by Western blot. A Western blot control for cellular GAPDH in cells is illustrated. HEK293T cells transfected with mVP40 (FIG. 3E) were treated with DMSO alone (lane 1), or with the indicated concentrations of 6 (FIG. 3E, lanes 2-6) as a negative control. Cells and VLPs were harvested at 24 hours post-transfection, and mVP40 was detected by Western blot.
Figure 3B:
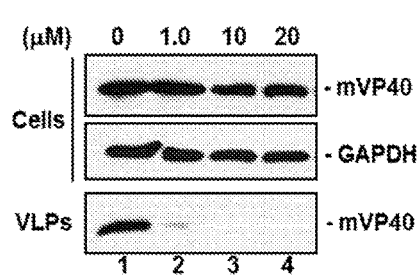
Figure 3C:
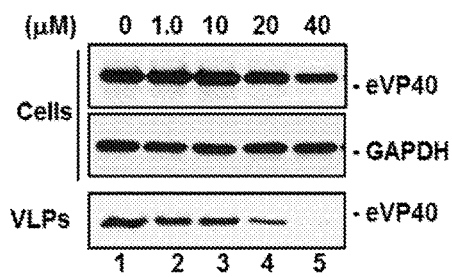
Figure 3D:
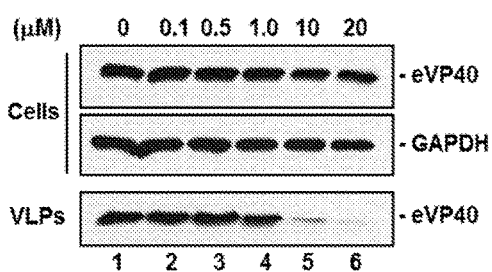

Using the structure of 1 as the starting point, SAR analog testing was performed to identify structurally related and progressively more potent small molecule inhibitors of budding. 2 and 3 were identified and tested for their ability to inhibit egress of both MARV and EBOV VP40 VLPs in a dose-dependent manner (FIGS. 3A-3E). Briefly, HEK293T cells were transfected with plasmids expressing either mVP40 or eVP40 in the absence (DMSO alone) or presence of the indicated concentrations of 2 (FIGS. 3A & 3C) or 3 (FIGS. 3B & 3D). Both cell extracts and VLPs were harvested at 24 hours post-transfection, and levels of mVP40 and eVP40 were assessed by Western blotting.

Compound 2 inhibited egress of mVP40 VLPs by 33- and 100-fold at concentrations of 20 µM and 40 µM, respectively (FIG. 3A; VLPs, lanes 4+5) without any detrimental effect on the levels of mVP40 and host GAPDH in cell extracts (FIG. 3A; Cells, lanes 1-5). Compound 2 inhibited egress of eVP40 VLPs by 2.5- and 40-fold at concentrations of 20 µM and 40 µM, respectively (FIG. 3C; VLPs, lanes 4+5) without any detrimental effect on the levels of eVP40 and host GAPDH in cell extracts (FIG. 3C; Cells, lanes 1-5).

Figure 3E:
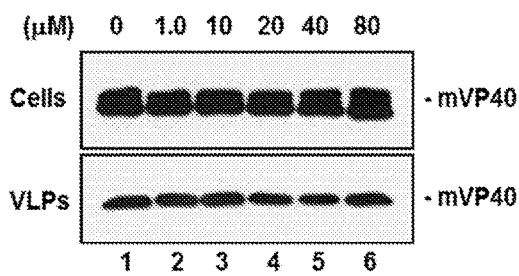

Relative to 2, compound 3 was far more potent at inhibiting budding of both mVP40 and eVP40 VLPs. Indeed, 3 inhibited egress of mVP40 VLPs by 10-, 100-, and 100-fold at concentrations of 1.0 µM, 10 µM, and 20 µM, respectively (FIG. 3B; VLPs, lanes 2-4), and inhibited egress of eVP40 VLPs by <2-, 4.5-, and 20-fold at concentrations of 1.0 µM, 10 µM, and 20 µM, respectively (FIG. 3D; VLPs, lanes 4-6). Compound 3 had no effect on expression levels of mVP40, eVP40, or GAPDH in cell extracts at any concentration tested (FIGS. 3B & 3D; Cells). Negative control 6 served to validate the specificity and anti-budding activity of 2 and 3, since 6 showed no effect on either cell or VLP expression levels of mVP40 at any concentration tested (FIG. 3E, lanes 1-6).

Example 5: Anti-Budding Activity of Compounds 4 and 5

SAR studies allowed for the identification of 4 and 5, which were tested for their ability to inhibit PPxY-dependent budding of both VLPs and live virus from cell culture, as well as to competitively block the interaction between mVP40 and host Nedd4 in live mammalian cells using a BiMC approach. Briefly, HEK293T cells were transfected with plasmids expressing either mVP40 or eVP40 in the absence (DMSO alone) or presence of the indicated concentrations of 4 (FIGS. 4A-4B). Both cell extracts and VLPs were harvested at 24 hours post-transfection, and levels of mVP40 and eVP40 were assessed by Western blotting and quantified. Compound 4 inhibited egress of mVP40 VLPs by 30- and 100-fold at concentrations of 0.5 µM and 1.0 µM, respectively (FIG. 4A; VLPs, lanes 3+4; bar graph). Compound 4 inhibited egress of eVP40 VLPs by 3- and 10-fold at concentrations of 0.5 µM and 1.0 µM, respectively (FIG. 4B; VLPs, lanes 2+3; bar graph). Compound 4 had no effect on expression levels of mVP40, GAPDH, or HSP70 in cell extracts at all concentrations tested (FIGS. 4A-4B; Cells).

A BiMC assay was used to determine whether 4 could specifically block the protein-protein interaction between mVP40 and host Nedd4 in a dose-dependent manner (FIG. 4C). Briefly, the mechanistic basis of the BiMC assay involves the splitting of YFP into N-(NYFP) and C-terminal (CYFP) halves that are then joined to two proteins of interest (mVP40 and Nedd4) (Lu et al., 2013, J. Virol. 87:7777-7780; Liu et al., 2011, J. Infect. Dis. 204 Suppl 3:S817-824; Kerppola, 2006, Nature Protocols 1:1278-1286). If mVP40 and Nedd4 interact when co-expressed in mammalian cells, then the N- and C-terminal halves of YFP will come together to reconstitute a functional YFP yielding a fluorescent signal. NYFP-Nedd4 and CYFP-mVP40 were co-expressed in human HEK293T cells for 4-5 hours and then cells were treated with DMSO alone, or the indicated concentrations of 4 or 6 (as a negative control) (FIG. 4C). Twenty four hours after transfection, cells were examined for YFP fluorescence (FIG. 4C). Total cell counts based on NucBlue staining indicated that equivalent numbers of cells were present in all BiMC samples. YFP positive cells constituted approximately 20% of total cells in the presence of vehicle alone, indicating that this assay is capable of detecting mVP40 interactions with host Nedd4 (FIG. 4C). Importantly, YFP positive cells decreased to 6.0% and 3.0% in the presence of 0.5 µM and 1.0 µM concentrations of 4, respectively, indicating that 4 inhibits interactions between mVP40 and host Nedd4 (FIG. 4C). No such inhibition was observed in cells treated with 10 µM or 20 µM concentrations of 6, confirming the specificity of the inhibitory activity observed for 4 (FIG. 4C).

Figure 5A:
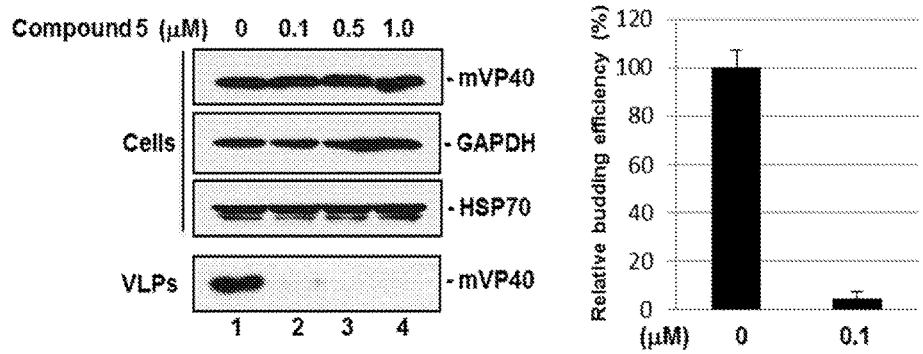
FIGS. 5A-5C illustrate the finding that compound 5 inhibits budding of mVP40 and eVP40 VLPs and blocks mVP40-Nedd4 protein-protein interaction.
Figure 5B:
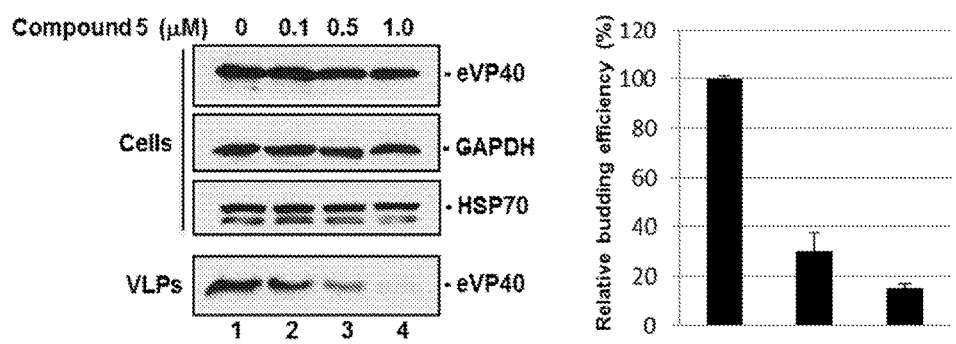
Figure 5C:
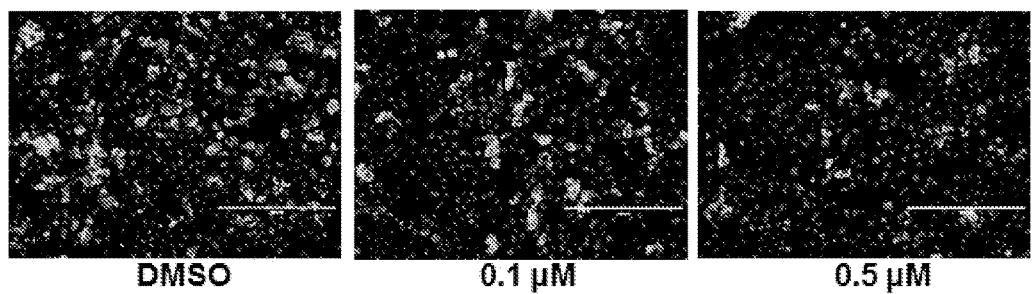

Similar analyses were carried out with 5 (FIGS. 5A-5C). Compound 5 inhibited egress of mVP40 VLPs by 25-, 100-, and 100-fold at concentrations of 0.1 µM, 0.5 µM, and 1.0 µM respectively (FIG. 5A; VLPs, lanes 2-4; bar graph). Compound 5 inhibited egress of eVP40 VLPs by <2-, 3.5-, and 7-fold at concentrations of 0.1 µM, 0.5 µM, and 1.0 µM respectively (FIG. 5B; VLPs, lanes 2-4; bar graph). Compound 5 had no effect on expression levels of mVP40, eVP40, GAPDH, or HSP70 in cell extracts at all concentrations tested (FIGS. 5A+5B; Cells). A BiMC assay was used to determine whether 5 could specifically block the mVP40-Nedd4 interaction in a dose-dependent manner (FIG. 5C). Total cell counts based on NucBlue staining indicated that equivalent numbers of cells were present in all BiMC samples. Indeed, YFP positive cells decreased in a dose-dependent manner in the presence of 0.1 µM and 0.5 µM concentrations of 5 compared to those observed in the presence of vehicle alone (FIG. 5C).

Example 6: Compounds 4 and 5 inhibit VLP budding of PPxY-containing LFV Z Protein The Z protein of LFV contains both a PPxY and a PTAP motif. The PPxY L-domain motif plays a role in efficient egress of LFV Z VLPs (FIG. 6A). For example, deletion of the PPxY motif resulted in a 4-fold decrease in VLP production compared to that of WT LFV Z (FIG. 6A). Thus, it was tested whether 4 and 5 could inhibit budding of LFV Z VLPs. Briefly, HEK293T cells were transfected with plasmids expressing LFV Z in the absence (DMSO alone) or presence of the indicated concentrations of 4 (FIG. 6B) or 5 (FIG. 6C). Both cell extracts and VLPs were harvested at 24 hours post-transfection, and levels of LFV Z were assessed by Western blotting.

Compound 4 inhibited egress of LFV Z VLPs by >5-fold at a concentration of 0.5 µM and by >10-fold at a concentration of 1.0 µM (FIG. 6B; VLPs). Similarly, 5 inhibited egress of LFV Z VLPs by approximately 3-, 5-, and >10-fold at concentrations of 0.1 µM, 0.5 µM, and 1.0 µM, respectively (FIG. 6C; VLPs). Compounds 4 and 5 had no effect on expression levels of LFV Z or actin in cell extracts at all concentrations tested (FIGS. 6B-6C; Cells).

Figure 7B:
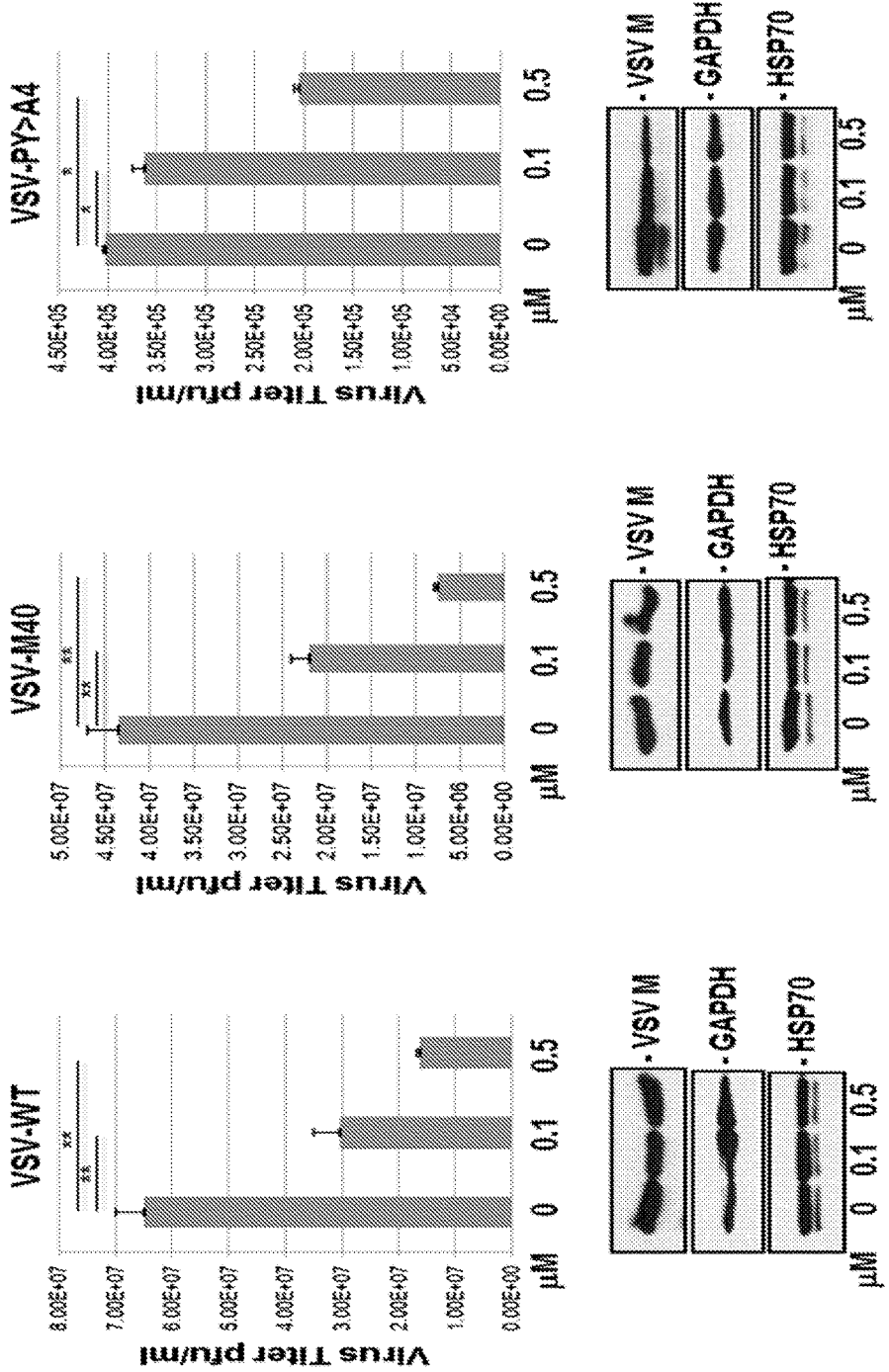

Example 7: Effect of Compounds 4 and 5 on Budding of Live VSV and VSV Recombinants The potential anti-budding activity of 4 and 5 against live viruses that depend on a functional PPxY L-domain for efficient egress was evaluated. Toward this end, HEK293T cells were infected for 8 hours at an MOI of 0.1 with either VSV-WT (containing a single PPxY L-domain), recombinant VSV-M40 (containing overlapping EBOV PTAP and PPxY L-domains), or VSV-PY>A4 (a PPxY mutant and budding defective virus) in the absence (DMSO alone) or presence of the indicated concentration of 4 (FIG. 7A) or 5 (FIG. 7B).

Compound 4 inhibited egress of VSV-WT by >2-fold at 0.1 µM and by approximately 20-fold at 0.5 µM without affecting viral or host protein synthesis (FIG. 7A, left panel). Indeed, titers of VSV-WT averaging $3.3 \times 10^7$ pfu/ml at 8 hours post-infection were significantly reduced to an average of $1.8 \times 10^6$ pfu/ml in the presence of 0.5 µM concentration of 4 (FIG. 7A, left panel). Not surprisingly, 4 inhibited egress of VSV-M40 to a lesser degree by approximately 2-fold at 0.1 µM and by 3-fold at 0.5 µM without affecting viral or host protein synthesis (FIG. 7A, middle panel). As expected, 4 exhibited no significant inhibition of VSV-PY>A4 budding at all concentrations tested (FIG. 7A, right panel). Compound 5 inhibited egress of VSV-WT by >2-fold at 0.1 µM and by 4-fold at 0.5 µM without affecting viral or host protein synthesis (FIG. 7B, left panel). Compound 5 inhibited egress of VSV-M40 by 2-fold at 0.1 µM and by 6-fold at 0.5 µM without affecting viral or host protein synthesis (FIG. 7B, middle panel). Lastly, budding of VSV-PY>A4 was reduced by <2-fold in the presence of 0.1 µM and 0.5 µM concentrations of 5 (FIG. 7B, right panel).

Example 8: Effect of Compounds of the Invention on Budding of PPxY-Containing RABV Efficient budding of RABV is also dependent on a single PPxY L-domain within its M protein, and the potential anti-budding activity of 4 and 5 against live RABV in cell culture was evaluated. Briefly, HEK293T cells were infected with RABV SPBN at an MOI of 0.1 in the absence (DMSO alone) or presence of the indicated concentration of 4 or 5, and virus-containing supernatants were harvested at 24, 36, and 72 hours p.i. and titered in duplicate by plaque assay on BSR cells (FIGS. 8A-8B).

Compound 4 reduced RABV titers at 36 hours post-infection in a dose-dependent manner by approximately 5- and 10-fold at 0.5 µM and 1.0 µM, respectively (FIG. 8A). Compound 4 reduced RABV titers at 72 hours post-infection in a dose-dependent manner by approximately 10- and 50-fold at 0.5 µM and 1.0 µM, respectively (FIG. 8A). A similar dose-dependent reduction in RABV titers of approximately 5- and 30-fold was observed in the presence of 5 at 36 hours post-infection at 0.5 µM and 1.0 µM, respectively (FIG. 8B). Compound 5 reduced RABV titers at 72 hours post-infection by approximately 40- and 80-fold at 0.5 and 1.0 µM, respectively (FIG. 8B). Inhibition of RABV budding by 4 and 5 was observed as early as 24 hours post-infection. Equivalent amounts of RABV M were detected by Western blot from cell extracts receiving vehicle alone, or the indicated concentrations of 4 and 5. Without wishing to be limited by any theory, these inhibitors do not appear to adversely affect viral protein synthesis at the concentrations tested (FIG. 8C).

Example 9: Identification of Inhibitors of Virus Budding

Using the known structure of the Nedd4 WW-domain/PPxY interaction as a guide, an in silico strategy was used to screen 4.8 million drug-like compounds in a ZINC database to identify potential lead compounds that would inhibit binding of Nedd4 to the viral PPxY L-domain. This strategy led to the initial identification of compound 1, which was shown to specifically block PPxY-mediated budding of Marburg VP40 VLPs. Analogs of 1 exhibited more potent activity in blocking PPxY-mediated VLP egress and in specifically blocking the PPxY-Nedd4 interaction as determined using the BiMC assay.

Example 10: SAR Studies

To understand how the structure of 1 affected its activity, the molecule was dissected into two fragments 2 and 3 (FIG. 10), and derivatives thereof were prepared and evaluated.

Compound 2b showed good activity at 10 µM in the M VP40 budding assay. Compound 2e was active in the M VP40 budding assay at 10 µM but also inhibited viral protein synthesis at slightly higher potencies. Compound 2 was considerably more potent than 1, with nearly full inhibition of egress of Marburg (M) VP40 VLPs at 20 µM and of Ebola (E) VP40 VLPs at 40 µM. Without wishing to be limited by any theory, budding of E-VP40 is dependent on both PTAP and PPxY L-domains, whereas budding of M-VP40 is dependent solely on a PPxY L-domain, and that may help explain why PPxY inhibitors inhibit egress of M-VP40 better than E-VP40.

Figure 10:
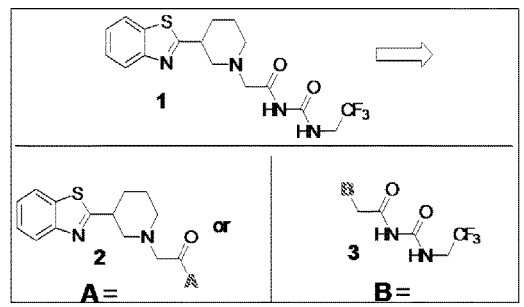
FIG. 10 is a set of tables that illustrate analogs of 1 (2, 2b-2e; 3, 3b-3e), analogs of 2 (4, 2g), and analogs of 3 (3f-3g, 3i-3l, 5).
Figure 10:
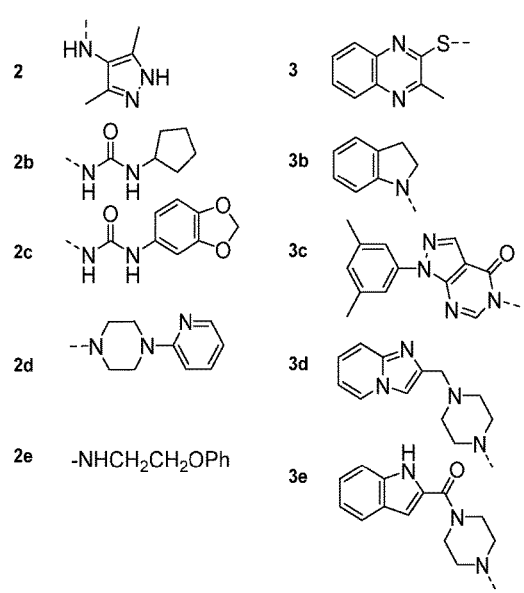
Figure 10:
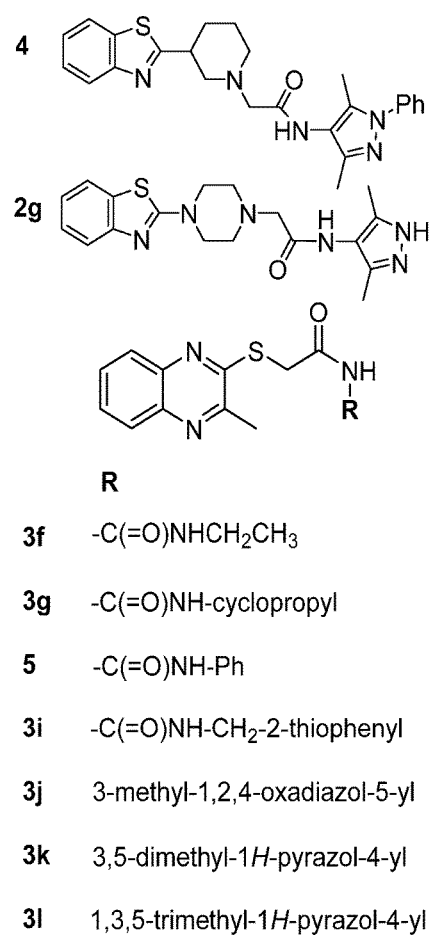

Compound 2 also showed target engagement in the M-BiMC and E-BiMC assays and also significantly inhibited budding of live wild type VSV at these concentrations. Based on the results of compounds in FIG. 10, additional analogs of 2 were analyzed (FIG. 10). Analog 2g is a pseudo regiochemical isomer of 2 (1,4-piperazine versus 1,3-piperidine). These changes led to an inactive compound. However replacing the pyrazole hydrogen of 2 with a phenyl group (4) improved the potency into the sub-micromolar region.

Compounds 3b-3e were not active or weakly active at our highest dose (40 µM). However compound 3, in which the left hand fragment of 1 is replaced by a 3-methyl-quinoxaline-2-thiol group, was very effective in inhibiting MVP40 VLP budding, showing a dose response from 10 to 0.5 µM with significant potency at the lowest dose. Additional analogs of 3 are shown in FIG. 10. A hybrid compound (31) that combined the 3-methyl-quinoxaline-2-thiol fragment of 3 with the N-(3,5-dimethyl-1H-pyrazol-4-yl)-acetamide fragment of 2b had low activity. Analogs of 31 (such as 3k) also had low activity. However analogs more closely related in structure to 3 (such as 5, 3i, 3f, 3g) were shown in preliminary characterizations to be as or more potent than 3 in the MVP40 budding assay. Compound 5 demonstrated anti-budding activity on MVP40 into the low nM region ($IC_{50}$<100 nM, FIG. 10).

Further examination of FIGS. 10-11 reveals a nascent SAR arising with two lead series represented by 2 and 3 and interdependence of the assays. Greater potency in inhibition of budding relates to greater potency in both the BiMC and live virus assays.

Figure 12A:
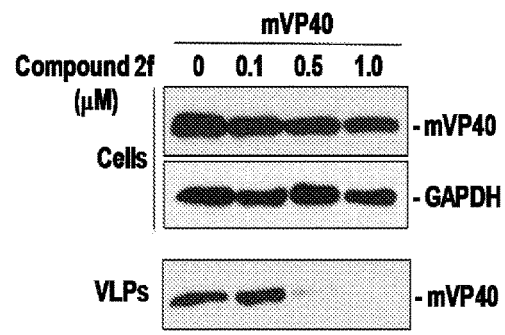
FIGS. 12A-12C illustrate the finding that compound 4 inhibits PPxY-dependent budding and protein interactions.
Figure 12B:
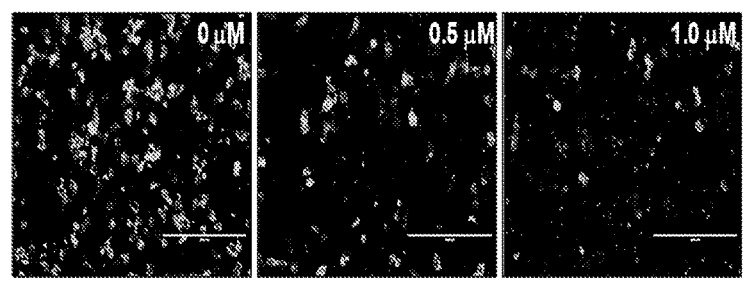

Compound 4 blocked PPxY-dependent egress of both Marburg VP40 VLPs and live infectious vesicular stomatitis virus (VSV) in cell culture in a dose-dependent manner (FIGS. 12A-12C) in low micromolar concentrations. In addition, compound 4 was shown to inhibit the viral PPxY-host WW-domain interaction between Marburg VP40 and host Nedd4 proteins in a BiMC assay in a dose-dependent manner (FIG. 12B).

In certain embodiments, the compounds of the invention interfere with the viral PPxY-host WW domain interaction and are useful in broad-spectrum antiviral therapy. In other embodiments, the compounds of the invention have one or more of the following characteristics: in vitro potency as indicated by BiMIC MV40 $IC_{50}$<1 µM, MVP40<1 µM, EVP40 $IC_{50}$<5 µM and BiMC EVP40 $IC_{50}$<5 µM; little or no cytotoxicity; ADME characteristics approaching the following values: plasma protein binding (<95%), microsomal stability (human, and mouse $t_{1/2}$>30 min), Cyp inhibition (<20% inhibition of 3A4 at 10 µM); and good stability in mouse PK under iv administration: low to moderate CL, moderate Vd, $t_{1/2}$>1 hr. In yet other embodiments, certain surrogate monitors of ADME drug properties, such as lipophilicity (cLogP, <4.5) and topological polar surface area (tPSA, 60-120 Å$^2$), correlate with good clearance properties and avoidance of off-target toxicities associated both with high molecular weight and lipophilicity.

Example 11: SAR Studies

Figure 13:
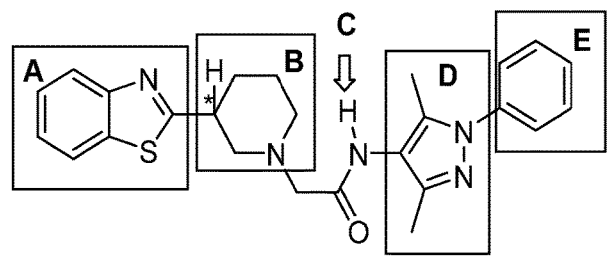
FIG. 13 is a scheme illustrating design of analogs of 4.
Figure 14:
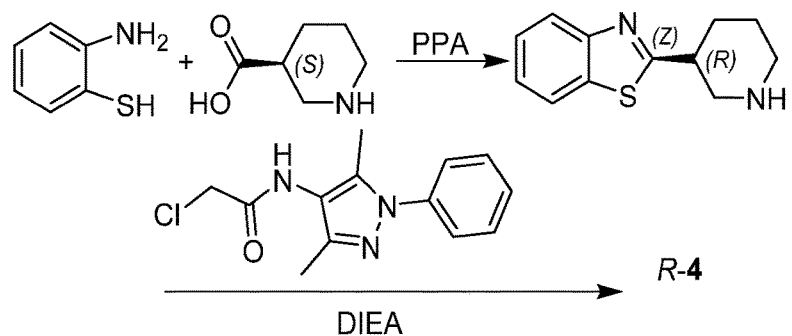
FIG. 14 is a scheme illustrating synthesis of enantiomers of 4.

Analogs of 4 and 3 are prepared, as described herein.
Compound 4:
Compound 4 has a chiral center (designated by * in FIG. 13). Both enantiomers are synthesized (FIG. 14; R-4 from S-nipecotic acid is shown, S-4 could be obtained similarly from R-nipecotic acid) to examine enantioselectivity. Structurally related analogs of 4 are also prepared and characterized. Analogs of 4 may be prepared using methodology summarized in FIG. 14.

Substructure A (FIG. 13): To test electronic and steric substituent effects, aryl substituted analogs are prepared. In addition, benzothiazole scaffold changes are targeted to afford benzoxazole (replace S with O) or benzimidazole (replace S with NH or NMe) systems by short synthetic sequences.

Substructure B (FIG. 13): Analogs with distint rings (such as pyrrolidine or 1,4-piperidine) are prepared. The chiral H atom is also replaced with lower alkyl groups.

Substructure C (FIG. 13): A N-methyl analog is prepared.
Substructure D (FIG. 13): Analogs with distinct 3- and 5-substituted pyrazoles and other ring systems (e.g., pyrrole, imidazole, isoxazole) are prepared.

Figure 15:
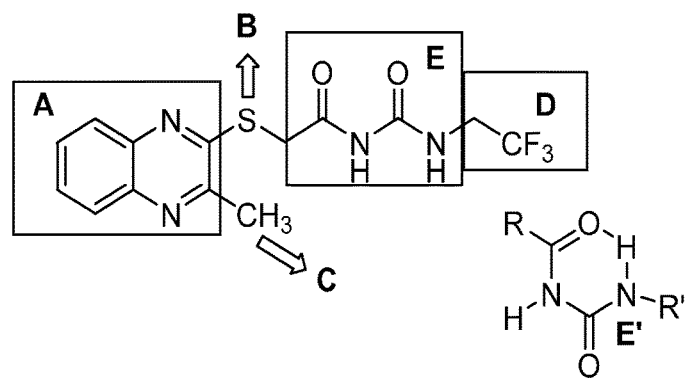
FIG. 15 is a scheme illustrating design of analogs of 3.
Figure 16:
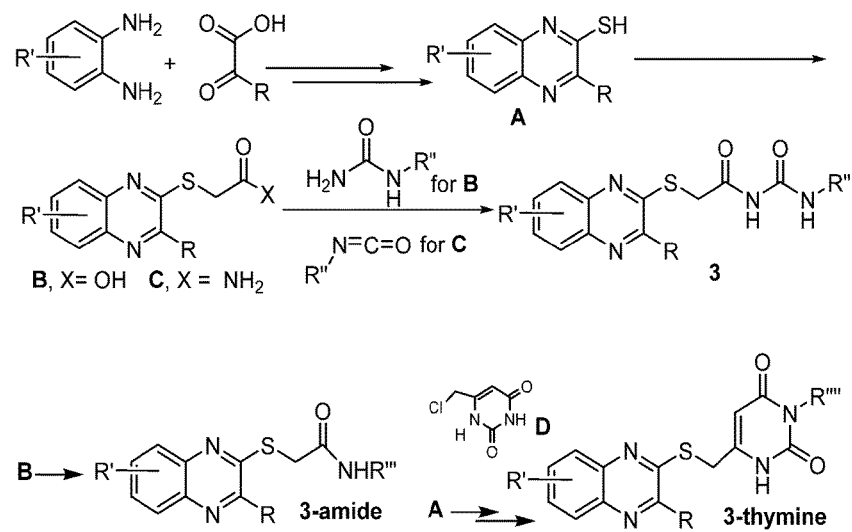
FIG. 16 is a scheme illustrating synthesis of analogs of 3.

Substructure E (FIG. 13): Analogs having lower alkyl, benzyl or substituted phenyl groups at this position are synthesized.
Compound 3:
Analogs of compound 3 are prepared (FIG. 15).
Substructure A (FIG. 15): Substituted quinoxaline analogs of 3 are prepared, using for example commercially available substituted 1,2-diaminobenzene derivatives (FIG. 16). The thiol 4 can readily be converted to acid 5 or primary amide 6 and these could be reacted with substituted ureas or isocyanates respectively to give analogs of 3. Distinct scaffolds other than quinoxaline, such as naphthyl, quinazoline, and quinoline scaffolds, are also prepared.

Substructure B (FIG. 15): Oxygen, carbon or nitrogen derivatives are prepared.

Substructure C (FIG. 15): Derivatives wherein the methyl group is replaced with H, Ph, CF$_3$, or Bn are prepared.

Substructure D (FIG. 15): Analogs of 3 are synthesized from ureas/isocyanates and intermediates 5 or 6 (FIG. 16).

Substructure E (FIG. 15): N-methylated analogs are prepared. Libraries of 3-amide derivatives from 5 are also prepared (see box in FIG. 16). In certain embodiments, cyclic systems such as thymine derivatives (3-thymine in FIG. 16) may replace C(=O)—NH—C(=O)—NH. Synthesis of such system is exemplified in FIG. 16.

Example 12: BiMC and VLP Budding Assays

Figure 12C:
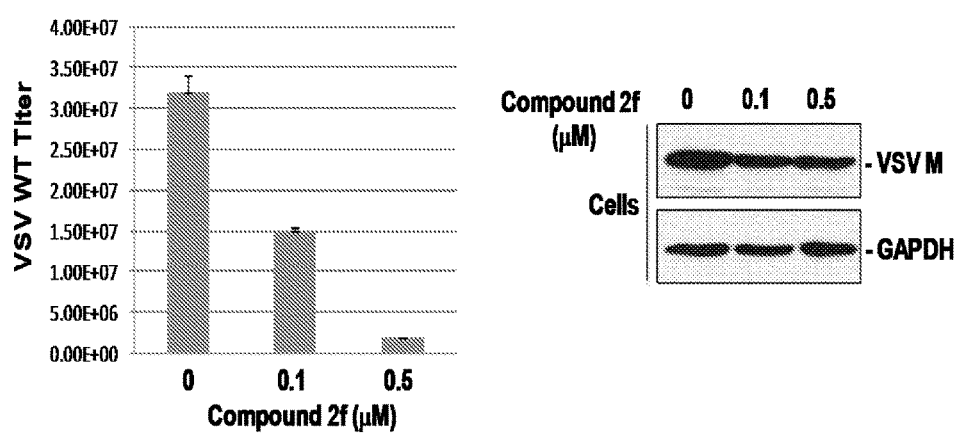

BiMC and VLP budding assays may be used to test analogues for their efficacy in specifically inhibiting the PPxY-Nedd4 interaction and subsequent egress of Filovirus particles. The VLP budding assay recapitulates live virus budding to determine the antiviral potency of analogs identified in Aim 1 (FIGS. 12A-12C). Egress of VLPs consisting of mVP40-WT or PPxY mutants of mVP40 as controls (e.g. mVP40-AAAA or mVP40-ΔPY) is quantified in the presence of each analog in a dose-dependent manner, and those that robustly block PPxY-dependent VLP egress are identified. Without wishing to be limited by any theory, inhibitors that block the PPxY-Nedd4 interaction more potently than compound 4 in BiMC assays also more potently inhibit VLP budding.

A BiMC approach is implemented to detect and visualize mVP40-Nedd4 interactions in live mammalian cells (FIGS. 12A-12C). BiMC is used to evaluate the relative ability of 4 analogs to disrupt mVP40-Nedd4 interactions. NYFP-Nedd4 and appropriate CYFP-WT or PPxY mutants of mVP40 are co-expressed in HEK293T cells and the potency of inhibitors blocking fluorescent complementation of mVP40-Nedd4 complexes is visualized using an inverted Leica Sp5-II confocal microscope. Quantitative analysis of complementation is determined by scoring individual cells and the rate, localization, intensity, and kinetics of fluorescence accumulation to determine drug potency. A PPxY L-domain mutant of mVP40 that does not interact with Nedd4 is utilized as a negative control, and MTT cell viability assays is performed in triplicate for all analogs tested.

Example 13: Egress Blockage of Live Virus in Cell Culture

Compounds of the invention are evaluated for their ability to block egress of live virus in cell culture. To determine whether the compounds of the invention inhibit live virus budding, inhibitors of VP40-Nedd4 interactions and VLP egress are evaluated for their ability to reduce live virus production.

In certain embodiments, the compounds are tested for their ability to block budding of live VSV-WT or VSV-PPxY mutants (FIGS. 12A-12C).

In other embodiments, the compounds of the invention are evaluated for their ability to block PPxY-dependent budding of live WT or PPxY mutants of rabies virus.

In yet other embodiments, VSV recombinants that possess WT PPxY or PPxY mutant L-domains and flanking sequences derived from Marburg virus VP40 and Lassa fever Z proteins are generated. VSV recombinants expressing heterologous L-domains from filoviruses or arenaviruses serve as valuable BSL-2 tools and allow for the accurate assessment of the efficacy of Nedd4 inhibitors on live virus egress. Standard PCR and cloning techniques and reverse-genetics approach are used to replace sequences in the full-length cDNA of VSV encoding the L-domain and flanking residues of VSV M protein with those from mVP40 and Lassa Z protein.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed:
1. A compound of formula (II):

wherein:
ring a is fused with ring b to form bicyclic core ab,
wherein ring a is selected from the group consisting of benzene and, pyridine
wherein a is optionally substituted with one or more substituents independently selected from the group consisting of $C_1$-$C_4$ alkyl optionally substituted with one or more fluoro atoms, $C_3$-$C_6$ cycloalkyl optionally substituted with one or more fluoro atoms, nitro, cyano, halogen, hydroxy, $C_1$-$C_4$ alkoxy optionally substituted with one or more fluoro atoms, $C_1$-$C_4$ thioalkoxy optionally substituted with one or more fluoro atoms, —SO$_2$($C_1$-$C_4$ alkyl), —C(=O)OR, —NRR, and —C(=O)NRR;
Q is S, S(=O), S(=O)$_2$, O or NR;
each occurrence of R is independently H or $C_1$-$C_4$ alkyl;
$R^1$ is selected from the group consisting of H, $C_1$-$C_4$ alkyl optionally substituted with one or more fluoro atoms, $C_3$-$C_6$ cycloalkyl optionally substituted with one or more fluoro atoms, aryl, substituted aryl, heteroaryl, substituted heteroaryl, arylalkyl, substituted arylalkyl, heteroarylalkyl, substituted heteroarylalkyl, heteroalkyl, substituted heteroalkyl, —C(=O)OR, and —C(=O)NRR;
$R^2$ is selected from the group consisting of —C(=O)N(R)C(=O)NR$^3$R$^4$ and —C(=O)N(R)C(=O)OR$^3$;
$R^3$ is selected from the group consisting of H, $C_1$-$C_4$ alkyl optionally substituted with one or more fluoro atoms, $C_3$-$C_6$ cycloalkyl optionally substituted with one or more fluoro atoms, aryl, substituted aryl, heteroaryl, substituted heteroaryl, arylalkyl, substituted arylalkyl, heteroarylalkyl, substituted heteroarylalkyl, heteroalkyl, substituted heteroalkyl, —C(=O)OR and —C(=O)NRR;
$R^4$ is H or $C_1$-$C_4$ alkyl, or $R^3$ and $R^4$ are taken together with the N atom to which both groups are bound to form a four- to seven-membered optionally substituted heterocyclic or heteroaromatic ring;
$R^5$ is selected from the group consisting of H and $C_1$-$C_4$ alkyl optionally substituted with at least one substituent selected from the group consisting of halo, hydroxy, $C_1$-$C_4$ alkoxy, $C_1$-$C_4$ thioalkoxy, —SO$_2$($C_1$-$C_4$ alkyl), —C(=O)OR, —NRR and —C(=O)NRR;
wherein the compound is not selected from the group consisting of 2-((3-methylquinoxalin-2-yl)thio)-N-((2,2,2-trifluoroethyl)carbamoyl) acetamide (3); 2-((3-methylquinoxalin-2-yl)thio)-N-(phenylcarbamoyl)acetamide (5); 2-((3-methylquinoxalin-2-yl)thio)-N-((thiophen-2-ylmethyl)carbamoyl)acetamide (3i); N-[(cyclopentylamino)carbonyl]-2-[(3-methyl-2-quinoxalinyl)thio]-acetamide; N-[(ethylamino)carbonyl]-2-[(3-methyl-2-quinoxalinyl)thio]-propanamide; N-[(methylamino)carbonyl]-2-[(3-methyl-2-quinoxalinyl) thio]-propanamide; N-[aminocarbonyl]-2-[(3-methyl-2-quinoxalinyl)thio]-3-methyl-butanamide;

N-[(methylamino)carbonyl]-2-(2-quinoxalinylthio)-propanamide; N-[(ethylamino)carbonyl]-2-(2-quinoxalinylthio)-propanamide; N-[[(1-methylethyl)amino]carbonyl]-2-(2-quinoxalinylthio)-propanamide; N-[[(phenylmethyl)amino]carbonyl]-2-(2-quinoxalinyloxy)-acetamide; N-[[(1-methylethyl)amino]carbonyl]-2-(2-quinoxalinyloxy)-acetamide; and ethyl (2-((3-methylquinoxalin-2-yl)thio)acetyl)carbamate (3y).

2. The compound of claim 1, which is at least one selected from the group consisting of:

N-(ethylcarbamoyl)-2-((3-methylquinoxalin-2-yl)thio)acetamide (3f)

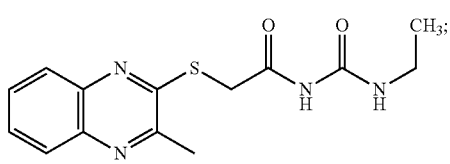 [SMILES: CCNC(=O)NC(=O)CSc1nc2ccccc2nc1C]

N-(cyclopropylcarbamoyl)-2-((3-methylquinoxalin-2-yl)thio)acetamide (3g)

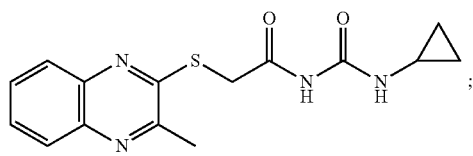 [SMILES: Cc1nc2ccccc2nc1SCC(=O)NC(=O)NC1CC1]

N-(benzylcarbamoyl)-2-((3-methylquinoxalin-2-yl)thio)acetamide (3o)

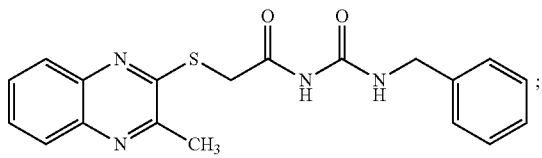 [SMILES: Cc1nc2ccccc2nc1SCC(=O)NC(=O)NCc1ccccc1]

2-((3-methylquinoxalin-2-yl)thio)-N-(pyridin-2-ylcarbamoyl)acetamide (3p)

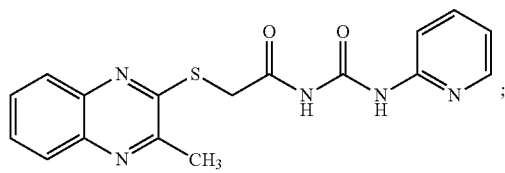

2-((3-methylquinoxalin-2-yl)thio)-N-(pyridin-3-ylcarbamoyl)acetamide (3q)

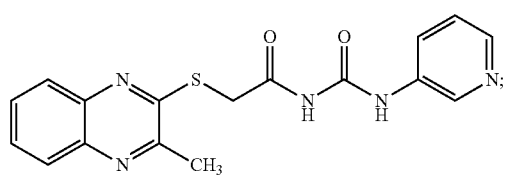 [SMILES: Cc1nc2ccccc2nc1SCC(=O)NC(=O)Nc1cccnc1]

N-((1H-pyrazol-3-yl)carbamoyl)-2-((3-methylquinoxalin-2-yl)thio)acetamide (3r)

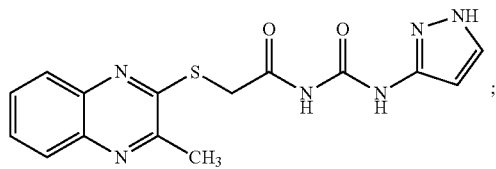 [SMILES: Cc1nc2ccccc2nc1SCC(=O)NC(=O)Nc1cc[nH]n1]

N-(3,5-dimethyl-1H-pyrazol-4-yl)carbamoyl)-2-((3-methylquinoxalin-2-yl)thio)acetamide (3s)

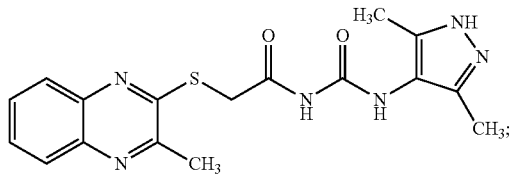 [SMILES: Cc1nc2ccccc2nc1SCC(=O)NC(=O)Nc1c(C)n[nH]c1C]

2-((3-methylquinoxalin-2-yl)thio)-N-((1,3,5-trimethyl-1H-pyrazol-4-yl)carbamoyl)acetamide (3t)

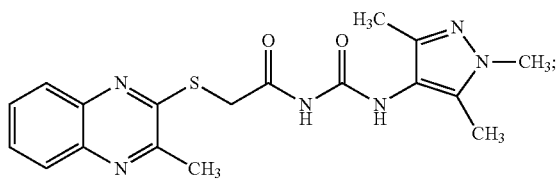 [SMILES: Cc1nc2ccccc2nc1SCC(=O)NC(=O)Nc1c(C)nn(C)c1C]

N-((2-fluorophenyl)carbamoyl)-2-((3-methylquinoxalin-2-yl)thio)acetamide (3u)

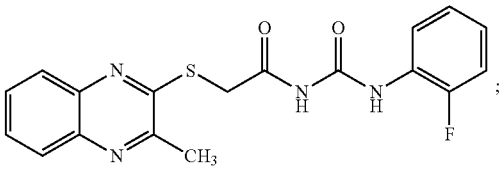

N-((3-fluorophenyl)carbamoyl)-2-((3-methylquinoxalin-2-yl)thio)acetamide (3v)

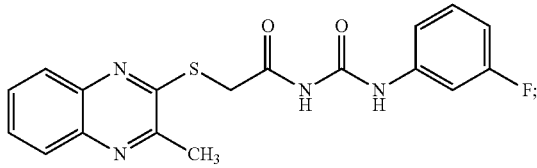 [SMILES: Cc1nc2ccccc2nc1SCC(=O)NC(=O)Nc1cccc(F)c1]

N-((4-fluorophenyl)carbamoyl)-2-((3-methylquinoxalin-2-yl)thio)acetamide (3w)

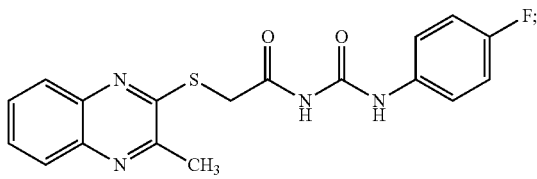 [SMILES: Cc1nc2ccccc2nc1SCC(=O)NC(=O)Nc1ccc(F)cc1]

1-[2-(3-methyl-quinoxalin-2-yloxy)-acetyl]-3-phenyl-urea (3x)

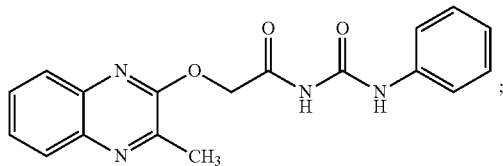 [SMILES: Cc1nc2ccccc2nc1OCC(=O)NC(=O)Nc1ccccc1]

1-Methyl-3-[2-(3-methyl-quinoxalin-2-ylsulfanyl)-acetyl]-1-phenyl-urea (3aa)

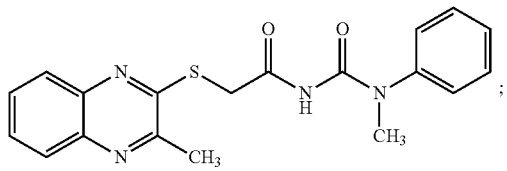 [SMILES: Cc1nc2ccccc2nc1SCC(=O)NC(=O)N(C)c1ccccc1]

1-[2-(3-Benzyl-quinoxalin-2-ylsulfanyl)-acetyl]-3-(3,5-dimethyl-1H-pyrazol-4-yl)-urea (3ab)

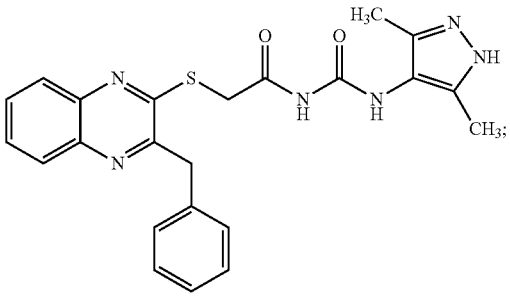 [SMILES: Cc1n[nH]c(C)c1NC(=O)NC(=O)CSc1nc2ccccc2nc1Cc1ccccc1]

2-((3-benzylquinoxalin-2-yl)thio)-N41,3,5-trimethyl-1H-pyrazol-4-yl)carbamoyl)acetamide (3ac)

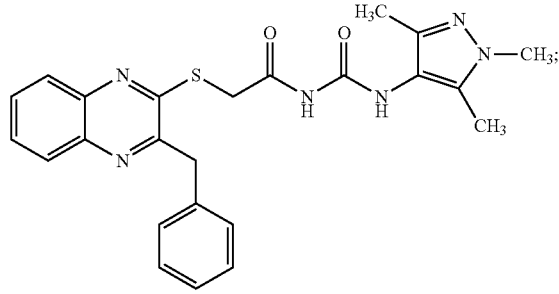 [SMILES: Cc1nn(C)c(C)c1NC(=O)NC(=O)CSc1nc2ccccc2nc1Cc1ccccc1]

and, 2-((3-benzylquinoxalin-2-yl)thio)-N-((4-fluorophenyl)carbamoyl)acetamide (3ad)

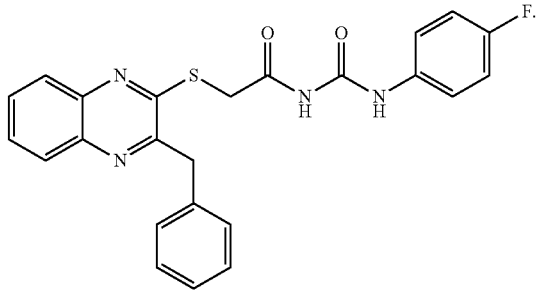 [SMILES: O=C(CSc1nc2ccccc2nc1Cc1ccccc1)NC(=O)Nc1ccc(F)cc1]

3. A pharmaceutical composition comprising at least one pharmaceutically acceptable carrier and a compound of formula (II):

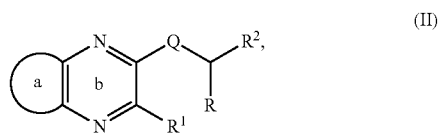

wherein
ring a is fused with ring b to form bicyclic core ab, wherein ring a is selected from the group consisting of benzene and pyridine,
wherein a is optionally substituted with one or more substituents independently selected from the group consisting of $C_1$-$C_4$ alkyl optionally substituted with one or more fluoro atoms, $C_3$-$C_6$ cycloalkyl optionally substituted with one or more fluoro atoms, nitro, cyano, halogen, hydroxy, $C_1$-$C_4$ alkoxy optionally substituted with one or more fluoro atoms, $C_1$-$C_4$ thioalkoxy optionally substituted with one or more fluoro atoms, —SO$_2$($C_1$-$C_4$ alkyl), —C(=O)OR, —NRR, and —C(=O)NRR;
Q is S, S(=O), S(=O)$_2$, O or NR;
each occurrence of R is independently H or $C_1$-$C_4$ alkyl;
$R^1$ is selected from the group consisting of H, $C_1$-$C_4$ alkyl optionally substituted with one or more fluoro atoms, $C_3$-$C_6$ cycloalkyl optionally substituted with one or more fluoro atoms, aryl, substituted aryl, heteroaryl, substituted heteroaryl, arylalkyl, substituted arylalkyl, heteroarylalkyl, substituted heteroarylalkyl, heteroalkyl, substituted heteroalkyl, —C(=O)OR, and —C(=O)NRR;
$R^2$ is selected from the group consisting of —C(=O)N(R)C(=O)NR$^3$R$^4$ and —C(=O)N(R)C(=O)OR$^3$ ;
$R^3$ is selected from the group consisting of H, $C_1$-$C_4$ alkyl optionally substituted with one or more fluoro atoms, $C_3$-$C_6$ cycloalkyl optionally substituted with one or more fluoro atoms, aryl, substituted aryl, heteroaryl, substituted heteroaryl, arylalkyl, substituted arylalkyl, heteroarylalkyl, substituted heteroarylalkyl, heteroalkyl, substituted heteroalkyl, —C(=O)OR and —C(=O)NRR;
$R^4$ is H or $C_1$-$C_4$ alkyl, or $R^3$ and $R^4$ are taken together with the N atom to which both groups are bound to form a four- to seven-membered optionally substituted heterocyclic or heteroaromatic ring; and,
$R^5$ is selected from the group consisting of H and $C_1$-$C_4$ alkyl optionally substituted with at least one substituent selected from the group consisting of halo, hydroxy, $C_1$-$C_4$ alkoxy, $C_1$-$C_4$ thioalkoxy, —SO$_2$($C_1$-$C_4$ alkyl), —C(=O)OR, —NRR and —C(=O)NRR.

4. The pharmaceutical composition of claim 3, further comprising at least one additional antiviral agent.

5. The pharmaceutical composition of claim 4, wherein the compound and the at least one additional agent are coformulated in the composition.

6. The pharmaceutical composition of claim 3, wherein the at least one compound is selected from the group consisting of:
2-((3-methylquinoxalin-2-yl)thio)-N-((2,2,2-trifluoroethyl)carbamoyl) acetamide (3);
N-(ethylcarbamoyl)-2-((3-methylquinoxalin-2-yl)thio) acetamide (3f);

N-(cyclopropylcarbamoyl)-2-((3-methylquinoxalin-2-yl) thio)acetamide (3g);
2-((3-methylquinoxalin-2-yl)thio)-N-(phenylcarbamoyl) acetamide (5);
2-((3-methylquinoxalin-2-yl)thio)-N-((thiophen-2-ylmethyl)carbamoyl)acetamide (3i);
6-(3-Methyl-quinoxalin-2-ylsulfanylmethyl)-1H-pyrimidine-2,4-dione (3n);
N-(benzylcarbamoyl)-2-((3-methylquinoxalin-2-yl)thio) acetamide (3o);
2-((3-methylquinoxalin-2-yl)thio)-N-(pyridin-2-ylcarbamoyl)acetamide (3p);
2-((3-methylquinoxalin-2-yl)thio)-N-(pyridin-3-ylcarbamoyl)acetamide (3q);
N-((1H-pyrazol-3-yl)carbamoyl)-2-((3-methylquinoxalin-2-yl)thio)acetamide (3r);
N4(3,5-dimethyl-1H-pyrazol-4-yl)carbamoyl)-2-((3-methylquinoxalin-2-yl)thio)acetamide (3s);
243-methylquinoxalin-2-yl)thio)-N-((1,3,5-trimethyl-1H-pyrazol-4-yl)carbamoyl)acetamide (3t);
N4(2-fluorophenyl)carbamoyl)-2-((3-methylquinoxalin-2-yl)thio)acetamide (3u);
N4(3-fluorophenyl)carbamoyl)-2-((3-methylquinoxalin-2-yl)thio)acetamide (3v);
N4(4-fluorophenyl)carbamoyl)-2-((3-methylquinoxalin-2-yl)thio)acetamide (3w);
1-[2-(3-Methyl-quinoxalin-2-yloxy)-acetyl]-3-phenylurea (3x);
ethyl (2-((3-methylquinoxalin-2-yl)thio)acetyl)carbamate (3y);
1-Methyl-3-[2-(3-methyl-quinoxalin-2-ylsulfanyl)-acetyl]-1-phenyl-urea (3aa);
1-[2-(3-Benzyl-quinoxalin-2-ylsulfanyl)-acetyl]-3-(3,5-dimethyl-1H-pyrazol-4-yl)-urea (3ab);
243-benzylquinoxalin-2-yl)thio)-N41,3,5-trimethyl-1H-pyrazol-4-yl)carbamoyl)acetamide (3ac); and,
2-((3-benzylquinoxalin-2-yl)thio)-N-((4-fluorophenyl) carbamoyl)acetamide (3ad).

7. A kit comprising
a compound of formula (II)

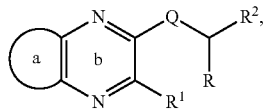

wherein:
ring a is fused with ring b to form bicyclic core ab, wherein ring a is selected from the group consisting of benzene and pyridine wherein a is optionally substituted with one or more substituents independently selected from the group consisting of $C_1$-$C_4$ alkyl optionally substituted with one or more fluoro atoms, $C_3$-$C_6$ cycloalkyl optionally substituted with one or more fluoro atoms, nitro, cyano, halogen, hydroxy, $C_1$-$C_4$ alkoxy optionally substituted with one or more fluoro atoms, $C_1$-$C_4$ thioalkoxy optionally substituted with one or more fluoro atoms, —$SO_2(C_1$-$C_4$ alkyl), —C(=O)OR, —NRR, and —C(=O)NRR;

Q is S, S(=O), S(=O)$_2$, O or NR;

each occurrence of R is independently H or $C_1$-$C_4$ alkyl;

$R^1$ is selected from the group consisting of H, $C_1$-$C_4$ alkyl optionally substituted with one or more fluoro atoms, $C_3$-$C_6$ cycloalkyl optionally substituted with one or more fluoro atoms, aryl, substituted aryl, heteroaryl, substituted heteroaryl, arylalkyl, substituted arylalkyl, heteroarylalkyl, substituted heteroarylalkyl, heteroalkyl, substituted heteroalkyl, —C(=O)OR, and —C(=O)NRR;

$R^2$ is selected from the group consisting of —C(=O)N(R)C(=O)NR$^3$R$^4$ and —C(=O)N(R)C(=O)OR$^3$ ;

$R^3$ is selected from the group consisting of H, $C_1$-$C_4$ alkyl optionally substituted with one or more fluoro atoms, $C_3$-$C_6$ cycloalkyl optionally substituted with one or more fluoro atoms, aryl, substituted aryl, heteroaryl, substituted heteroaryl, arylalkyl, substituted arylalkyl, heteroarylalkyl, substituted heteroarylalkyl, heteroalkyl, substituted heteroalkyl, —C(=O)OR and —C(=O)NRR;

$R^4$ is H or $C_1$-$C_4$ alkyl, or $R^3$ and $R^4$ are taken together with the N atom to which both groups are bound to form a four- to seven-membered optionally substituted heterocyclic or heteroaromatic ring;

$R^5$ is selected from the group consisting of H and $C_1$-$C_4$ alkyl optionally substituted with at least one substituent selected from the group consisting of halo, hydroxy, $C_1$-$C_4$ alkoxy, $C_1$-$C_4$ thioalkoxy, —$SO_2(C_1$-$C_4$ alkyl), —C(=O)OR, —NRR and —C(=O)NRR;

wherein the kit further comprises instructional material comprising instructions for using the at least one compound to treat or prevent a viral infection in a subject.

8. The kit of claim 7, wherein the viral infection is caused by at least one virus selected from the group consisting of a filovirus, arenavirus, rhabdovirus, paramyxovirus, and retrovirus.

* * * * *

UNITED STATES PATENT AND TRADEMARK OFFICE
CERTIFICATE OF CORRECTION

PATENT NO. : 10,160,756 B2
APPLICATION NO. : 15/128471
DATED : December 25, 2018
INVENTOR(S) : Ronald N. Harty et al.

Page 1 of 1

It is certified that error appears in the above-identified patent and that said Letters Patent is hereby corrected as shown below:

In the Specification

In Column 1, after the title, STATEMENT REGARDING FEDERALLY SPONSORED RESEARCH OR DEVELOPMENT, please replace the paragraph at Lines 19-23 with the following paragraph:
--This invention was made with government support under grant numbers AI102104, AI057168, AI113952, AI125005, and AI115759 awarded by the National Institutes of Health. The government has certain rights in the invention.--

Signed and Sealed this
Second Day of April, 2019

Andrei Iancu
*Director of the United States Patent and Trademark Office*